(12) United States Patent
Park et al.

(10) Patent No.: US 10,548,560 B2
(45) Date of Patent: *Feb. 4, 2020

(54) X-RAY APPARATUS AND X-RAY DETECTOR

(71) Applicant: SAMSUNG ELECTRONICS CO., LTD., Suwon-si (KR)

(72) Inventors: Hye-suk Park, Yongin-si (KR); Woo-sup Han, Yongin-si (KR); Sang-uk Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/293,183

(22) Filed: Mar. 5, 2019

(65) Prior Publication Data

US 2019/0192107 A1 Jun. 27, 2019

Related U.S. Application Data

(63) Continuation of application No. 14/951,806, filed on Nov. 25, 2015, now Pat. No. 10,258,307.

(30) Foreign Application Priority Data

Nov. 26, 2014 (KR) .................. 10-2014-0166623

(51) Int. Cl.
*A61B 6/00* (2006.01)
(52) U.S. Cl.
CPC ............ *A61B 6/587* (2013.01); *A61B 6/4266* (2013.01); *A61B 6/4452* (2013.01); *A61B 6/547* (2013.01); *A61B 6/4458* (2013.01); *A61B 6/4464* (2013.01); *A61B 6/4476* (2013.01); *A61B 6/4494* (2013.01)

(58) Field of Classification Search
None
See application file for complete search history.

(56) References Cited

U.S. PATENT DOCUMENTS

| | | |
|---|---|---|
| 6,859,521 B2 | 2/2005 | Spahn |
| 7,324,628 B2 | 1/2008 | Liu et al. |
| 7,817,040 B2 | 10/2010 | Homanfar et al. |
| 8,243,883 B2 | 8/2012 | Omernick et al. |

(Continued)

FOREIGN PATENT DOCUMENTS

| | | |
|---|---|---|
| CN | 101039624 A | 9/2007 |
| CN | 102293657 A | 12/2011 |

(Continued)

OTHER PUBLICATIONS

Communication dated Nov. 28, 2017 issued by the European Patent Office in counterpart Application No. 15863859.3.

(Continued)

*Primary Examiner* — Hoon K Song
(74) *Attorney, Agent, or Firm* — Sughrue Mion, PLLC

(57) ABSTRACT

An X-ray apparatus includes an X-ray radiator configured to radiate X-rays to an object and a controller configured to acquire orientation information indicating an orientation of the X-ray radiator and motion information indicating a movement of an X-ray detector configured to detect the X-rays radiated by the X-ray radiator and select the X-ray detector based on the orientation information and the motion information.

17 Claims, 32 Drawing Sheets

(56) References Cited

U.S. PATENT DOCUMENTS

| | | | |
|---|---|---|---|
| 8,690,426 B2 | 4/2014 | Liu et al. | |
| 8,941,070 B2 | 1/2015 | Petrick et al. | |
| 9,526,465 B2 | 12/2016 | Nenoki et al. | |
| 10,258,307 B2 * | 4/2019 | Park | A61B 6/547 |
| 2002/0080921 A1 | 6/2002 | Smith et al. | |
| 2003/0161439 A1 | 8/2003 | Eriksson et al. | |
| 2006/0109958 A1 | 5/2006 | Ertel et al. | |
| 2007/0165783 A1 | 7/2007 | Abu Tabanjeh | |
| 2011/0075817 A1 | 3/2011 | Takahashi et al. | |
| 2011/0274251 A1 | 11/2011 | Omernick | |
| 2012/0195407 A1 | 8/2012 | Nenoki et al. | |
| 2014/0133625 A1 | 5/2014 | Lee | |
| 2015/0049862 A1 | 2/2015 | Ancar | |

FOREIGN PATENT DOCUMENTS

| | | |
|---|---|---|
| CN | 102389318 A | 3/2012 |
| CN | 102613981 A | 8/2012 |
| EP | 2 390 682 A2 | 11/2011 |
| JP | 2003310591 A | 11/2003 |
| JP | 201057707 A | 3/2010 |
| JP | 2010119848 A | 6/2010 |
| JP | 2014-166556 A | 9/2014 |
| JP | 2014-198271 A | 10/2014 |
| KR | 101389525 B1 | 4/2014 |
| WO | 2013-162762 A1 | 10/2013 |
| WO | 2014-005937 A1 | 1/2014 |
| WO | 2014/055488 A2 | 4/2014 |
| WO | 2014-080686 A1 | 5/2014 |
| WO | 2014/081686 A1 | 5/2014 |

OTHER PUBLICATIONS

Communication dated Feb. 29, 2016, issued by the International Searching Authority in counterpart International Application No. PCT/KR2015/012717 (PCT/ISA/220, 210, 237).

Communication dated Aug. 13, 2019, issued by the European Patent Office in counterpart European Application No. 15863859.3.

Communication dated Oct. 16, 2019 issued by the State Intellectual Property Office of P.R. China in counterpart Chinese Application No. 201580062680.2.

* cited by examiner

X-RAY APPARATUS AND X-RAY DETECTOR

CROSS-REFERENCE TO RELATED PATENT APPLICATION

This application is a continuation of U.S. patent application Ser. No. 14/951,806, filed Nov. 25, 2015, which claims priority to Korean Patent Application No. 10-2014-0166623, filed on Nov. 26, 2014, in the Korean Intellectual Property Office, the disclosures of which are incorporated herein in their entireties by reference.

BACKGROUND

1. Field

The exemplary embodiments relate to X-ray apparatuses and X-ray detectors, and more particularly, to an X-ray apparatus that selects an X-ray detector that is to be used in X-ray imaging, based on orientation information of an X-ray radiator and orientation information of the X-ray detector, and an X-ray detector.

In addition, more particularly, the exemplary embodiments relate to an X-ray apparatus that selects an X-ray detector that is to be used in X-ray imaging, based on radiation information of an X-ray radiator included in the X-ray apparatus and motion information of the X-ray detector, and displays the selected X-ray detector, and an X-ray detector.

2. Description of the Related Art

In general, X-rays are electromagnetic waves having a wavelength of 0.01 to 100 Å and can pass through an object. Thus, X-rays may be commonly used in a wide range of applications, such as medical equipment that capture images of the inside of a living body and non-destructive testing equipment for industrial use.

X-ray imaging apparatuses using X-rays allow X-rays emitted by an X-ray source to pass through an object, and detect a difference between the intensities of the passed X-rays from an X-ray detector to thereby acquire an X-ray image of the object. X-ray imaging apparatuses are able to easily identify the internal structure of an object based on an X-ray image of the object and to diagnose a disease of the object. X-ray apparatuses are able to easily identify the internal structure of an object by using the principle that the transmission coefficient of X-rays varies depending on the density of the object and the atomic number of an atom of the object. As the wavelength of an X-ray becomes shorter, the transmission coefficient of X-rays increases, and a picture of the image obtained by the X-rays on a screen becomes clearer.

SUMMARY

According to an aspect of an exemplary embodiment, an X-ray apparatus includes an X-ray radiator configured to radiate X-rays to an object; and a controller configured to acquire orientation information indicating an orientation of the X-ray radiator and motion information indicating a movement of an X-ray detector configured to detect the X-rays radiated by the X-ray radiator and select the X-ray detector based on the orientation information and the motion information.

The X-ray apparatus may further include a communicator configured to transmit a control signal generated by the controller to the selected X-ray detector, the control signal being configured to control the selected X-ray detector.

The communicator may be configured to receive a signal related to the motion information from the X-ray detector, and the controller may be configured to determine the motion information based on the signal, the motion information comprising one selected from motion time information corresponding to a time period during which the X-ray detector moves, and motion direction information indicating a direction in which the X-ray detector moves.

The controller may be configured to acquire motion information indicating respective movements of a plurality of X-ray detectors, and select the X-ray detector from among the plurality of X-ray detectors based on the orientation information of the X-ray radiator and the motion information indicating respective movements of the plurality of X-ray detectors.

The controller may be configured to select the X-ray detector from among the plurality of X-ray detectors, based on motion time information corresponding to time periods during which the corresponding plurality of X-ray detectors move.

The controller may be configured to select an X-ray detector that has moved most recently from among the plurality of X-ray detectors based on the motion time information.

The controller may be configured to select the X-ray detector from among the plurality of X-ray detectors, based on motion direction information indicating respective movement directions of the plurality of X-ray detectors.

The controller may be configured to generate identification information identifying the X-ray detector selected based on the orientation information and the motion information.

The identification information identifying the X-ray detector may be generated based on motion direction information indicating a movement direction of the selected X-ray detector.

The identification information identifying the X-ray detector may include at least one selected from information indicating that the X-ray detector is combined with a stand type receptor, information indicating that the X-ray detector is combined with a table type receptor, and information indicating that the X-ray detector is not combined with any receptors.

When the motion direction information indicates that the movement direction of the X-ray detector is a first direction having a first trajectory, the controller may be configured to generate the information indicating that the X-ray detector is combined with the table type receptor.

When the motion direction information indicates that the movement direction of the X-ray detector is a second direction having a second trajectory, the controller may be configured to generate the information indicating that the X-ray detector is combined with the stand type receptor.

When the motion direction information indicates that the movement direction of the X-ray detector is neither a vertical direction nor a horizontal direction of a certain trajectory, the main controller may be configured to generate the information indicating that the X-ray detector is not combined with any receptors.

The X-ray apparatus may further include an outputter configured to display an icon representing the identification information.

The transmitted control signal may be configured to prepare the X-ray detector to receive the radiated X-rays.

The transmitted control signal may be generated based on user input.

The X-ray apparatus may further include: an outputter configured to display information representing a plurality of X-ray detectors that are selectable by a user; and an inputter configured to receive user input for selecting the X-ray detector from among the displayed information, wherein the controller is configured to select the X-ray detector according to the user input.

The controller may be configured to control the outputter to arrange the information representing the displayed plurality of X-ray detectors according to an arrangement criterion and output the arranged information.

According to an aspect of another exemplary embodiment, an X-ray detector includes: a sensor to sense a movement of the X-ray detector; a communicator configured to transmit motion information indicating the movement of the X-ray detector to an X-ray apparatus; and a detector controller configured to control the communicator to transmit the motion information to the X-ray apparatus and receive a control signal generated based on the motion information from the X-ray apparatus, and configured to control an operation of the X-ray detector based on the received control signal.

The detector controller may be configured to acquire the motion information based on a direction of the movement of the X-ray detector.

The detector controller may be configured to acquire the motion information based on a time period during which the movement of the X-ray detector occurs.

The detector controller may be configured to control the communicator to transmit the motion information to the X-ray apparatus at a predetermined time before receiving the control signal from the X-ray apparatus.

The control signal may be further generated based on orientation information of an X-ray radiator of the X-ray apparatus.

The detector controller may be configured to generate identification information identifying the X-ray detector based on the received control signal, and the X-ray detector may further include an outputter configured to output the generated identification information.

The detector controller may be configured to control the X-ray detector to prepare to receive radiated X-rays from the X-ray apparatus, based on the received control signal.

According to an aspect of another exemplary embodiment, an X-ray imaging device includes an X-ray radiator configured to emit X-rays toward an object; and a controller configured to obtain first information indicating spatial information of a first X-ray detector, second information indicating spatial information of a second X-ray detector, and third information indicating spatial information of the X-ray radiator, and select one of the first X-ray detector and the second X-ray detector as a target for the emitted X-rays based on the first information, the second information, and the third information.

The spatial information of the first X-ray detector may include a distance between the first X-ray detector and the X-ray radiator, the spatial information of the second X-ray detector may include a distance between the second X-ray detector and the X-ray radiator, and the spatial information of the X-ray radiator may include orientation information indicating an angle between an emission surface of the X-ray radiator and receiving surfaces of the first and second X-ray detectors, respectively.

According to an aspect of another exemplary embodiment, an X-ray imaging device includes an X-ray radiator configured to emit X-rays toward an object; and a controller configured to receive spatial information of a plurality of X-ray detectors, automatically select one of the X-ray detectors among the plurality of X-rays as a target for the emitted X-rays based on the spatial information, and activate the automatically selected X-ray detector to prepare the automatically selected X-ray detector to receive the emitted X-rays.

The controller may be configured to activate the automatically selected X-ray detector by transmitting a signal to the automatically selected X-ray detector, the signal being configured to control the automatically selected X-ray detector to switch from a first power mode to a second power mode, the first power mode using less power than the second power mode.

The X-ray imaging device may further include a display configured to display information, the controller may automatically select two or more of the X-ray detectors among the plurality of X-ray detectors and activate the automatically selected two or more X-ray detectors, and the display may be configured to display information selectable by a user to manually select one of the activated X-ray detectors.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
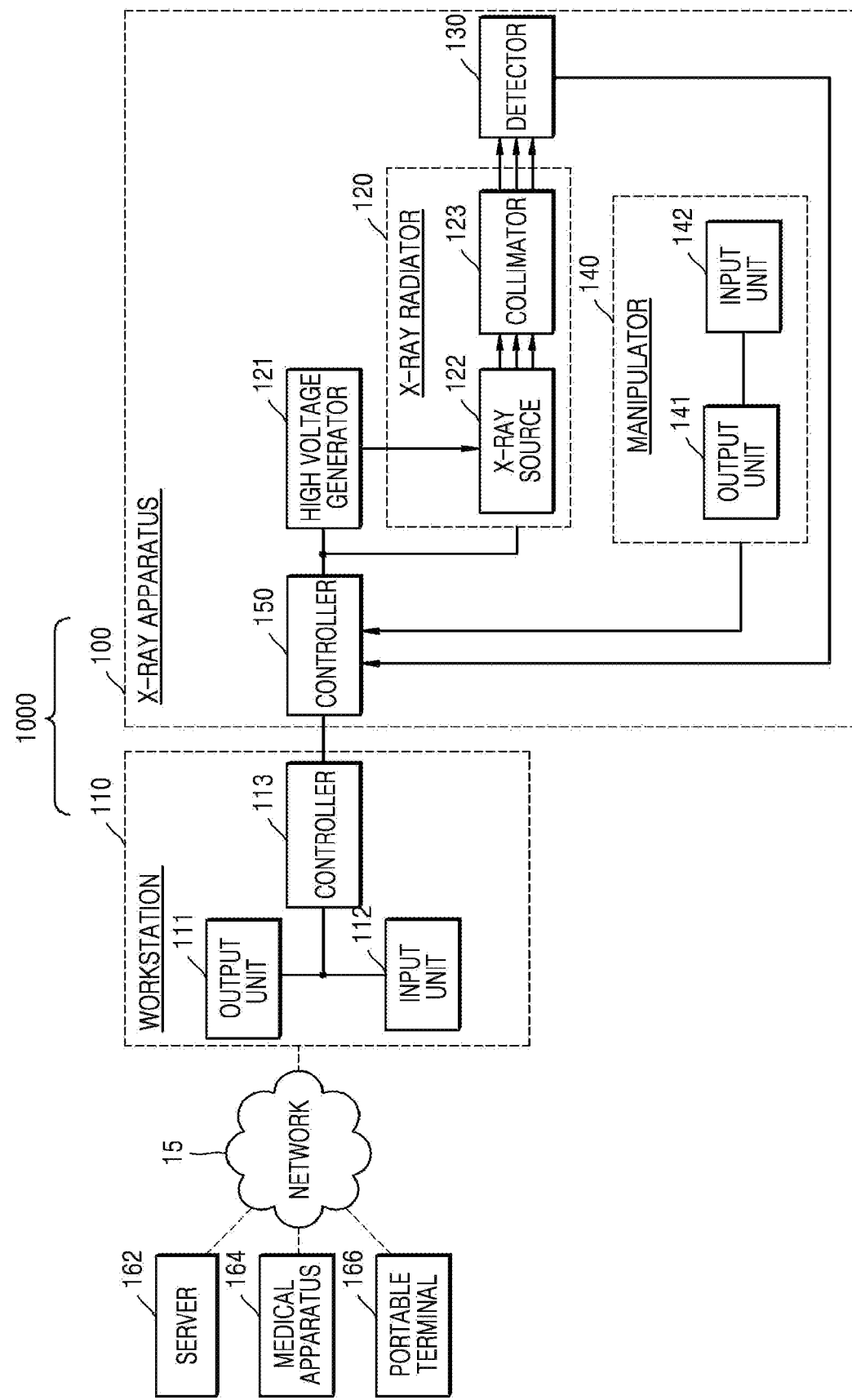
FIG. 1 is a block diagram of an X-ray system.

The attached drawings for illustrating exemplary embodiments of the present disclosure are referred to in order to gain a sufficient understanding of the exemplary embodiments, the merits thereof, and the objectives accomplished by the implementation of the exemplary embodiments. The exemplary embodiments may, however, be embodied in many different forms and should not be construed as being limited to the exemplary embodiments set forth herein; rather, these exemplary embodiments are provided such that this disclosure will be thorough and complete, and will fully convey the concept of the exemplary embodiments to one of ordinary skill in the art.

Hereinafter, the terms used in the specification will be briefly described, and then the exemplary embodiments will be described in detail.

The terms used in this specification are those general terms currently widely used in the art in consideration of functions regarding the exemplary embodiments, but the terms may vary according to the intention of those of ordinary skill in the art, precedents, or new technology in the art. Also, specified terms may be selected by the applicant, and in this case, the detailed meaning thereof will be described in the detailed description of the exemplary embodiments. Thus, the terms used in the specification should be understood not as simple names but based on the meaning of the terms and the overall description of the exemplary embodiments.

Throughout the specification, the term "image" may denote multi-dimensional data composed of discrete image elements (for example, pixels in a two-dimensional image and voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

Furthermore, in the exemplary embodiments, the term "object" may refer to a human, an animal, or a part of a human or animal. For example, the object may include an organ (for example, the liver, the heart, the womb, the brain, breasts, or the abdomen), blood vessels, or a combination thereof. The object may be a phantom. The term "phantom" denotes a material having a volume, a density, and an effective atomic number that are approximately the same as those of a living organism. For example, the phantom may be a spherical phantom having similar properties to those of the human body.

Throughout the specification, the term "user" may refer to, but is not limited to referring to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest imaging, simple abdomen imaging, simple skeleton imaging, simple nasal sinuses imaging, simple neck soft tissue imaging, and breast imaging.

FIG. 1 is a block diagram of an X-ray system 1000. Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 generates a high voltage for generating X-rays, and applies the high voltage to an X-ray source 122.

The X-ray radiator 120 includes the X-ray source 122 receiving the high voltage from the high voltage generator 121 to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode including a cathode and an anode. An inside of the X-ray tube is set as a high vacuum state of about 10 mmHg, and a filament of the anode is heated to a high temperature to generate thermal electrons.

The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiator 120 and has been transmitted through an object. The detector 130 may be a digital detector. The detector 130 may be implemented by using a thin film transistor (TFT) or a charge coupled device (CCD), although is not limited thereto and may be implemented using many different types of detectors. Although the detector 130 is included in the X-ray apparatus 100 in FIG. 1, the detector 130 may be an X-ray detector that is a separate device capable of being connected to or separated from the X-ray apparatus 100. An X-ray detector according to some exemplary embodiments may be a separate device capable of being connected to or separated from an X-ray apparatus.

The X-ray apparatus 100 may further include a manipulator 140 for providing a user with an interface for manipulating the X-ray apparatus 100. The manipulator 140 may include an output unit 141 (e.g., outputter) and an input unit 142 (e.g., inputter). The input unit 142 may receive from a user a command for manipulating the X-ray apparatus 100 and various types of information related to X-ray imaging. The controller 150 may control or manipulate the X-ray apparatus 100 according to the information received by the input unit 142. The output unit 141 may output sound representing information related to an imaging operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111 (e.g., outputter), an input unit 112 (e.g., inputter), and a controller 113. The output unit 111 and the input unit 112 provide a user with an interface for manipulating the workstation 110 and the X-ray apparatus 200. The controller 113 may control the workstation 110 and the X-ray apparatus 200.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is shown as being separate from the controller 150 of the X-ray apparatus 100 in FIG. 1, FIG. 1 is only an exemplary configuration. As another example, the controllers 113 and 150 may be integrated into a single controller, and the single controller may be included in only one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray radiation apparatus 100 include the output units 111 and 141, respectively, and the input units 112 and 142, respectively, in FIG. 1, exemplary embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed twice or according to some other criteria. The switch may include a switch provided such that a prepare command instructing a pre-heating operation for X-ray radiation to be performed may be input, and a switch provided such that a radiation command for X-ray radiation may be input.

In other words, when the user pushes the switch, a prepare command for performing a pre-heating operation for X-ray radiation may be input through the switch, and then, when the user pushes the switch once more, the radiation command for performing substantial X-ray radiation may be input through the switch. When the user manipulates the switch as described above, the controllers 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also prepares to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the high voltage generator 121 receives the prepare signal from the controllers 113 and 150, the high voltage generator 121 transmits the prepare signal for preparing to detect the X-ray to the detector 130. In this case, the detector 130 prepares to detect the X-ray in response to the prepare signal, and when the preparing for the detection is finished, the detector 130 transmits a ready signal to the high voltage generator 121. The high voltage generator 121 also transmits the ready signal received from the detector 130 to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141 so that the output units 111 and 141 output a predetermined sound and the object may recognize the radiation of the X-ray. The output units 111 and 141 may also output a sound representing information related to imaging in addition to the X-ray radiation. In FIG. 1, the output unit 141 is exemplarily shown as being included in the manipulator 140; however, the exemplary embodiments are not limited thereto, and the output unit 141 or a portion of the output unit 141 may be located elsewhere. For example, the output unit 141 may be located on a wall of an examination room in which the X-ray imaging of the object is performed.

The controllers 113 and 150 control locations of the X-ray radiator 120 and the detector 130, imaging timing, and imaging conditions, according to imaging conditions set by the user.

In more detail, the controllers 113 and 150 control the high voltage generator 121 and the detector 130 according to the command input via the input units 112 and 142 so as to control radiation timing of the X-ray, an intensity of the X-ray, and a region radiated by the X-ray. In addition, the control units 113 and 150 adjust the location of the detector 130 according to a predetermined imaging condition, and controls operation timing of the detector 130.

Furthermore, the controllers 113 and 150 generate a medical image of the object by using image data received via the detector 130. In detail, the controllers 113 and 150 may receive the image data from the detector 130, and then generate the medical image of the object by removing noise from the image data and adjusting a dynamic range and interleaving of the image data.

The output units 111 and 141 may output the medical image generated by the controllers 113 and 150. The output units 111 and 141 may output information to be used by the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and various other types of output devices well known to one of ordinary skill in the art.

The X-ray system 1000 shown in FIG. 1 may further include a communicator that may be connected to a server 162, a medical apparatus 164, and a portable terminal 166 via a network 15.

The communicator may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Also, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

According to an exemplary embodiment, the local area communication module refers to a module for performing local area communication with an apparatus located within a predetermined distance. Examples of local area communication technology may include, but are not limited to, a wireless local area network (LAN), Wi-Fi, Bluetooth, Zig-Bee, Wi-Fi Direct (WFD), ultra wideband (UWD), infrared data association (IrDA), Bluetooth low energy (BLE), and near field communication (NFC).

According to an exemplary embodiment, the wired communication module refers to a module for communicating by using an electric signal or an optical signal. Examples of wired communication technology may include wired communication techniques using a pair cable, a coaxial cable, an optical fiber cable, an HDMI cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signalling (LVDS), asynchronous serial communication, such as a universal asynchronous receiver transmitter (UART), a low latency network protocol, such as error synchronous serial communication or a controller area network (CAN), or any of other various types of communication methods that are well known to one of ordinary skill in the art.

Figure 2:
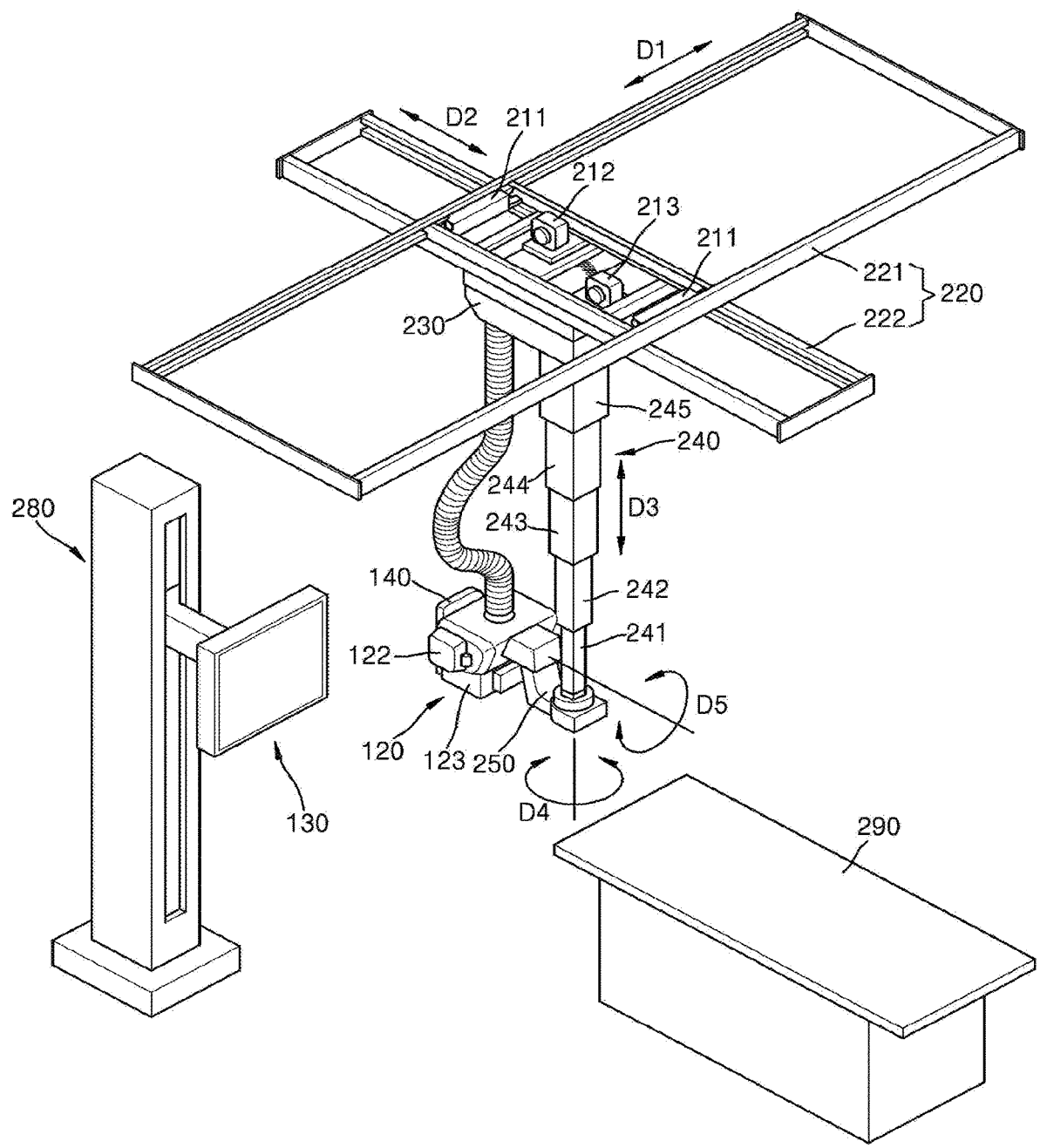
FIG. 2 is a perspective view of a fixed type X-ray apparatus.

FIG. 2 is a perspective view of a fixed type X-ray apparatus 200. The fixed type X-ray apparatus 200 may be another exemplary embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the fixed type X-ray apparatus 200 includes a manipulator 140 providing a user with an interface for manipulating the X-ray apparatus 200, an X-ray radiator 120 radiating an X-ray to an object, a detector 130 detecting an X-ray that has passed through the object, first, second, and third motors 211, 212, and 213 providing a driving power to transport the X-ray radiator 120, a guide rail 220, a moving carriage 230, and a post frame 240. The guide rail 220, the moving carriage 230, and the post frame 240 are formed to transport the X-ray radiator 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90° or another angle.

The first guide rail 221 is provided on the ceiling of an examination room in which the X-ray apparatus 200 is disposed.

The second guide rail 222 is located under the first guide rail 221, and is mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90° (or another angle), and may be parallel to the ceiling of the examination room.

The moving carriage 230 is disposed under the second guide rail 222 so as to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable (e.g., telescoping), and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table type receptor 290 or a stand type receptor 280.

A rotating joint 250 is disposed between the X-ray radiator 120 and the post frame 240. The rotating joint 250 allows the X-ray radiator 120 to be coupled to the post frame 240, and supports a load applied to the X-ray radiator 120.

The X-ray radiator 120 connected to the rotating joint 250 may rotate on a plane that is perpendicular to the third direction D3. In this case, a rotating direction of the X-ray radiator 120 may be defined as a fourth direction D4.

Also, the X-ray radiator 120 may be configured to be rotatable on a plane perpendicular to the ceiling of the examination room. Therefore, the X-ray radiator 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiator 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a power transfer unit (not shown) so as to linearly move the X-ray radiator 120 in the first, second, and third directions D1, D2, and D3. The driving power transfer unit may be a combination of a belt and a pulley, a combination of a chain and a sprocket, or a shaft, which are generally used.

In another example, motors (not shown) may be disposed between the rotating joint 250 and the post frame 240 and between the rotating joint 250 and the X-ray radiator 120 in order to rotate the X-ray radiator 120 in the fourth and fifth directions D4 and D5.

The manipulator 140 may be disposed on a side surface of the X-ray radiator 120.

FIG. 2 shows the fixed type X-ray apparatus 200 connected to the ceiling of the examination room, but the configuration of the fixed type X-ray apparatus 200 shown in FIG. 2 is merely an example for convenience of comprehension. That is, X-ray apparatuses according to exemplary embodiments may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

Figure 3:
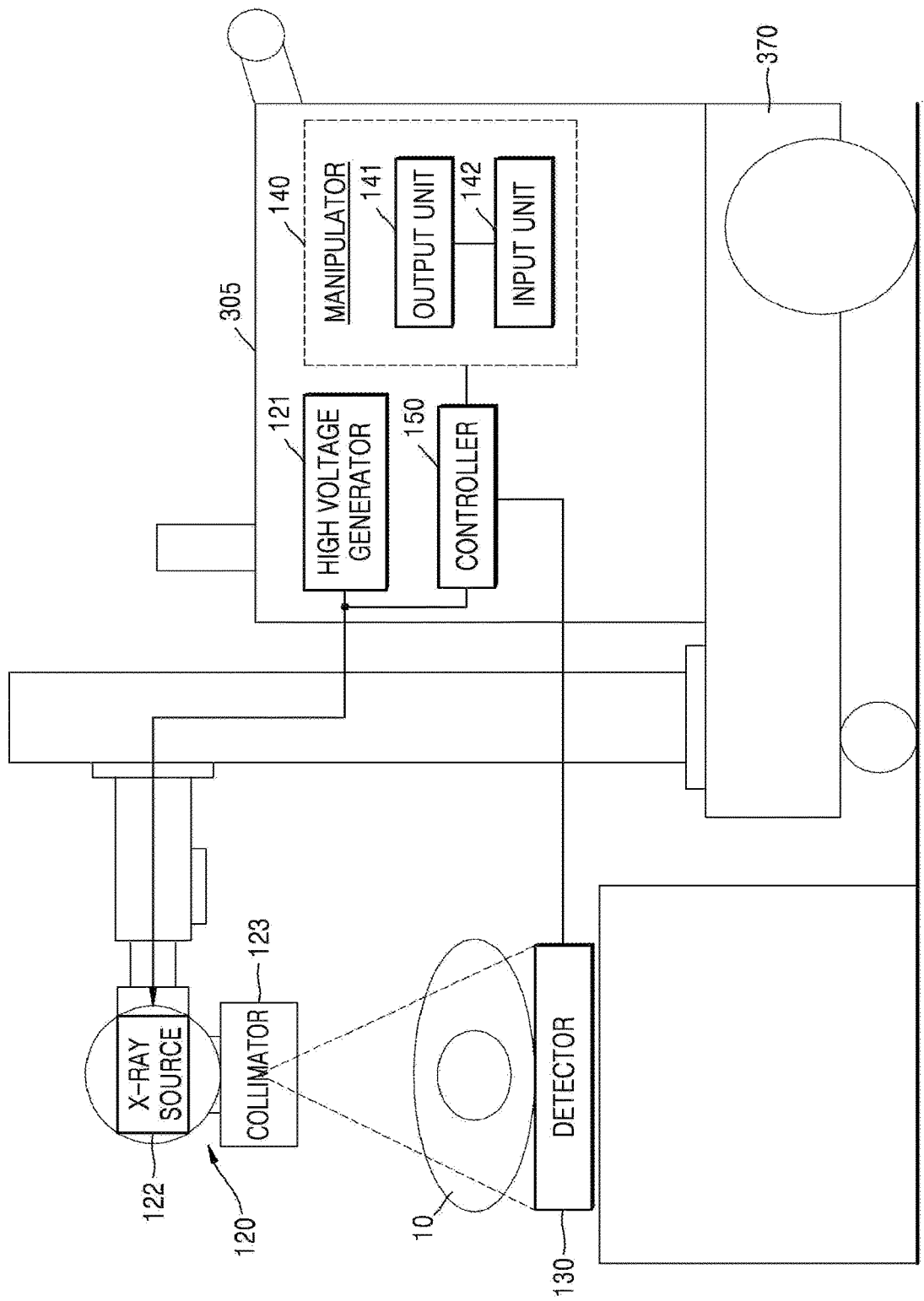
FIG. 3 is a diagram showing a configuration of a mobile X-ray apparatus capable of performing an X-ray imaging operation regardless of a place where the imaging operation is performed.

FIG. 3 is a diagram showing a configuration of a mobile X-ray apparatus 300 capable of performing an X-ray imaging operation regardless of a place where the imaging operation is performed. The mobile X-ray apparatus 300 may be another exemplary embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the mobile X-ray apparatus 300 includes a transport unit 370 including a wheel for transporting the mobile X-ray apparatus 300, a main unit 305, an X-ray radiator 120, and a detector 130 detecting an X-ray that is radiated from the X-ray radiator 120 toward an object and transmitted through the object. The main unit 305 includes a manipulator 140 providing a user with an interface for manipulating the mobile X-ray apparatus 300, a high voltage generator 121 generating a high voltage applied to an X-ray source 122, and a controller 150 controlling overall operations of the mobile X-ray apparatus 300. The X-ray radiator 120 includes the X-ray source 122 generating the X-ray, and a collimator 123 guiding a path along which the generated X-ray is emitted from the X-ray source 122 and adjusting an irradiation region radiated by the X-ray.

The detector 130 in FIG. 3 may not be combined with any receptor, and the detector 130 may be a portable detector which can exist anywhere.

In FIG. 3, the manipulator 140 is exemplarily shown as being included in the main unit 305; however, exemplary embodiments are not limited thereto. For example, as illustrated in FIG. 2, the manipulator 140 of the mobile X-ray apparatus 300 may be disposed on a side surface of the X-ray radiator 120.

The controller 150 controls locations of the X-ray radiator 120 and the detector 130, imaging timing, and imaging conditions according to imaging conditions set by the user.

In addition, the controller 150 generates a medical image of the object by using image data received from the detector 130. In detail, the controller 150 may generate the medical image of the object by removing noise from the image data received from the detector 130 and adjusting a dynamic range and interleaving of the image data.

The main unit 305 of the mobile X-ray apparatus 300 shown in FIG. 3 may further include an output unit (e.g., outputter) outputting the medical image generated by the controller 150. The output unit may output information that is to be used by the user to manipulate the mobile X-ray apparatus 300, for example, a UI, user information, or object information.

Figure 4:
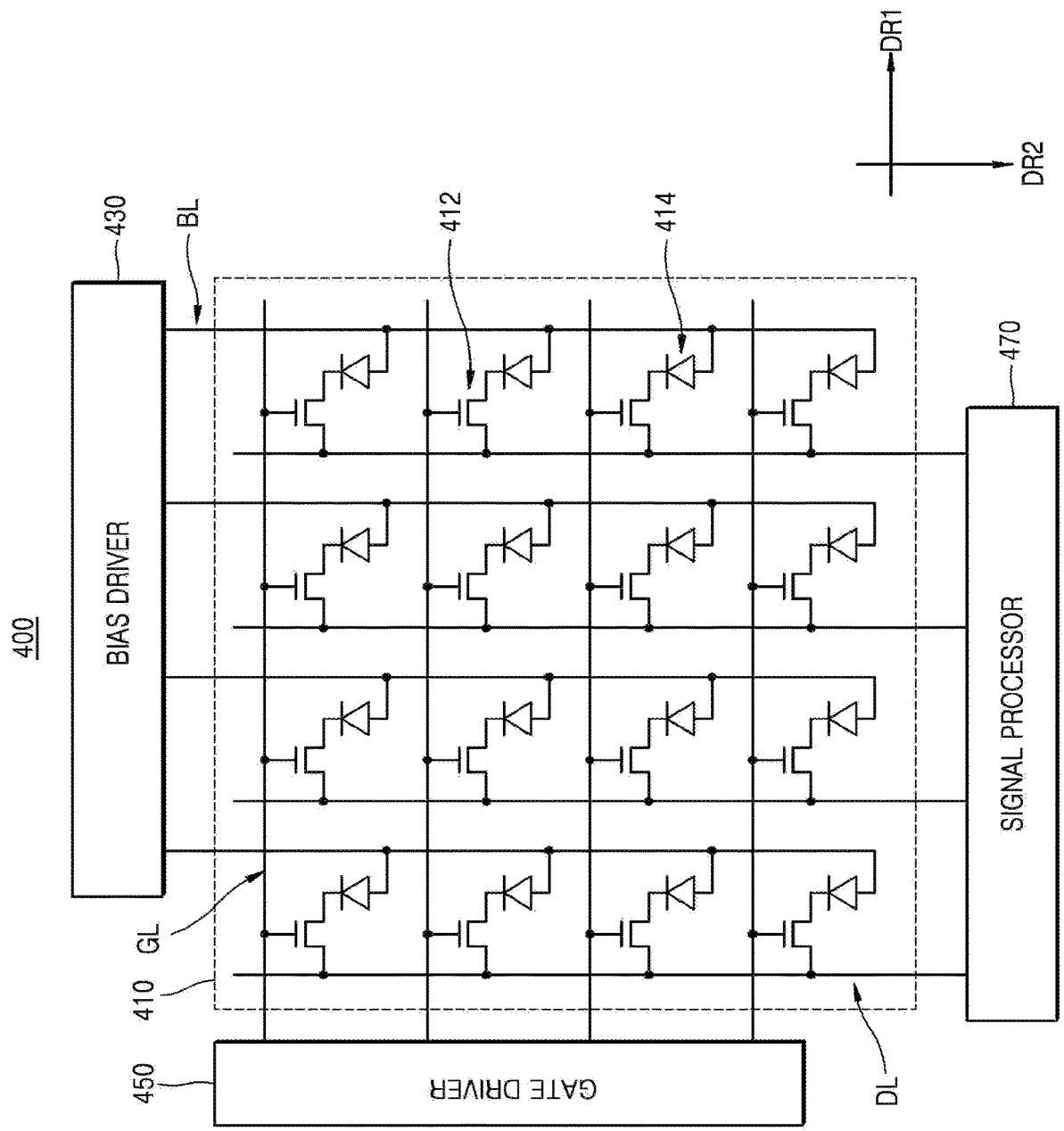
FIG. 4 is a diagram showing a detailed configuration of a detector.

FIG. 4 is a block diagram illustrating a structure of the CT system 400. The detector 400 may be an exemplary embodiment of the detector 130 of FIGS. 1-3. The detector 400 may be an indirect type detector.

Referring to FIG. 4, the detector 400 may include a scintillator (not shown), a photodetecting substrate 410, a bias driver 430, a gate driver 450, and a signal processor 470.

The scintillator receives the X-ray radiated from the X-ray source 122 and converts the X-ray into light.

The photodetecting substrate 410 receives the light from the scintillator and converts the light into an electrical signal. The photodetecting substrate 410 may include gate lines GL, data lines DL, TFTs 412, photodiodes 414, and bias lines BL.

The gate lines GL may be formed in the first direction DR1, and the data lines DL may be formed in the second direction DR2 that crosses the first direction DR1. The first direction DR1 and the second direction DR2 may intersect perpendicularly to each other. FIG. 4 shows four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 arrangement) are shown as an example, although more or less than sixteen TFTs may be used according to other exemplary embodiments.

The photodiodes 414 may be arranged as a matrix in the first and second directions DR1 and DR2 so as to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 so as to be electrically connected to the photodiodes 414. On the other hand, the bias lines BL may be formed to be substantially parallel with the first direction DR1 so as to be electrically connected to the photodiodes 414. Many different configurations of the bias lines BL are possible. FIG. 4 shows four bias lines BL formed along the second direction DR2 as an example.

The bias driver 430 is electrically connected to the bias lines BL so as to apply a driving voltage to the bias lines BL. The bias driver 430 may selectively apply a reverse bias voltage or a forward bias voltage to the photodiodes 414. A reference voltage may be applied to the N-side electrodes of the photodiodes 414. The reference voltage may be applied via the signal processor 470. The bias driver 430 may apply a voltage that is less than the reference voltage to the P-side electrodes of the photodiodes 414 so as to apply a reverse bias voltage to the photodiodes 414. On the other hand, the bias driver 430 may apply a voltage that is greater than the reference voltage to the P-side electrodes of the photodiodes 414 so as to apply a forward bias voltage to the photodiodes 414.

The gate driver 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The signal processor 470 is electrically connected to the data lines DL. When the light received by the photodetecting substrate 410 is converted into the electrical signal, the electrical signal may be read out by the signal processor 470 via the data lines DL.

An operation of the detector 400 will now be described. During the operation of the detector 400, the bias driver 430 may apply the reverse bias voltage to the photodiodes 414. While the TFTs 412 are turned off, each of the photodiodes 414 may receive the light from the scintillator and generate electron-hole pairs to accumulate electric charges.

The amount of electric charge accumulated in each of the photodiodes 414 may correspond to the intensity of the received X-ray.

Then, the gate driver 450 may sequentially apply the gate signals to the gate lines GL along the second direction DR2. When a gate signal is applied to a gate line GL and thus TFTs 412 connected to the gate line GL are turned on, photocurrents may flow into the signal processor 470 via the data lines DL due to the electric charges accumulated in the photodiodes 414 connected to the turned-on TFTs 412.

The signal processor 470 may convert the received photocurrents into image data and output the image data to the outside. The image data may be in the form of an analog signal or a digital signal corresponding to the photocurrents.

If the detector 400 shown in FIG. 4 is a wireless detector, the detector 400 may further include a battery unit (e.g., battery) and a wireless communication interface unit (e.g., wireless communication interface). For example, the wireless communication interface unit may include a transmitter and a receiver according to an exemplary embodiment.

When a plurality of X-ray detectors are compatibly used in one imaging space, although an operating environment of each of the X-ray detectors is not manually set by a user, if selection or activation of an X-ray detector that is used in X-ray imaging is automatically set based on orientation information of an X-ray radiator and orientation information of an X-ray detector, user convenience with respect to manipulation of an X-ray apparatus, especially, an operation of selecting a desired X-ray detector that is to be used for imaging from among the plurality of X-ray detectors, may increase.

For example, the orientation information of an X-ray radiator includes at least one selected from position information of the X-ray radiator and directional information thereof, and the orientation information of an X-ray detector may include at least one selected from position information of the X-ray detector and directional information thereof. It is understood that the orientation information may include other types of information as well.

Selection or activation of the X-ray detector that is used in X-ray imaging may also be automatically set, based on the orientation information of the X-ray radiator and motion information of the X-ray detector.

Based on the orientation information of the X-ray radiator and the motion information of the X-ray detector, the X-ray detector that is to be used in X-ray imaging may be identified. In this case, the X-ray detector may be identified based on identification information of the X-ray detector. For example, the identification information of the X-ray detector may include unique information of the X-ray detector that distinguishes the X-ray detector from not only other types of X-ray detectors but also from the same type of X-ray detectors as that of the X-ray detector, and information representing a mounting position of the X-ray detector.

For example, the motion information of the X-ray detector may include at least one selected from motion time information corresponding to a time section (time period) in which the X-ray detector moves, and motion direction information corresponding to a direction in which the X-ray detector moves.

When the user manually and directly selects an undesired X-ray detector from among the plurality of X-ray detectors and images an object, it is impossible to acquire an image of the object, and thus, the user again has to re-select a desired X-ray detector to re-image the object. Due to the re-imaging, the user feels inconvenience, and an accumulated amount of radiation, to which the object is exposed, increases.

Therefore, an X-ray apparatus according to an exemplary embodiment automatically selects or activates an X-ray detector that is to be used for imaging, based on orientation information of the X-ray detector and orientation information of an X-ray radiator. Accordingly, the user easily images an object even without spending much time and effort in selecting the X-ray detector to be used for imaging.

An X-ray apparatus according to another exemplary embodiment automatically selects or activates an X-ray detector that is to be used for imaging, based on orientation information of an X-ray radiator and motion information of the X-ray detector. Accordingly, the user easily images an object even without spending much time and effort in selecting the X-ray detector to be used for imaging.

An X-ray apparatus according to another exemplary embodiment generates identification information of an X-ray detector selected based on orientation information of an X-ray radiator and motion information of the X-ray detector, and displays an icon representing the identification information on a display of the X-ray apparatus and a display of the X-ray detector. Accordingly, the user easily recognizes the X-ray detector that is used for imaging, even without spending much time and effort.

Figure 5:
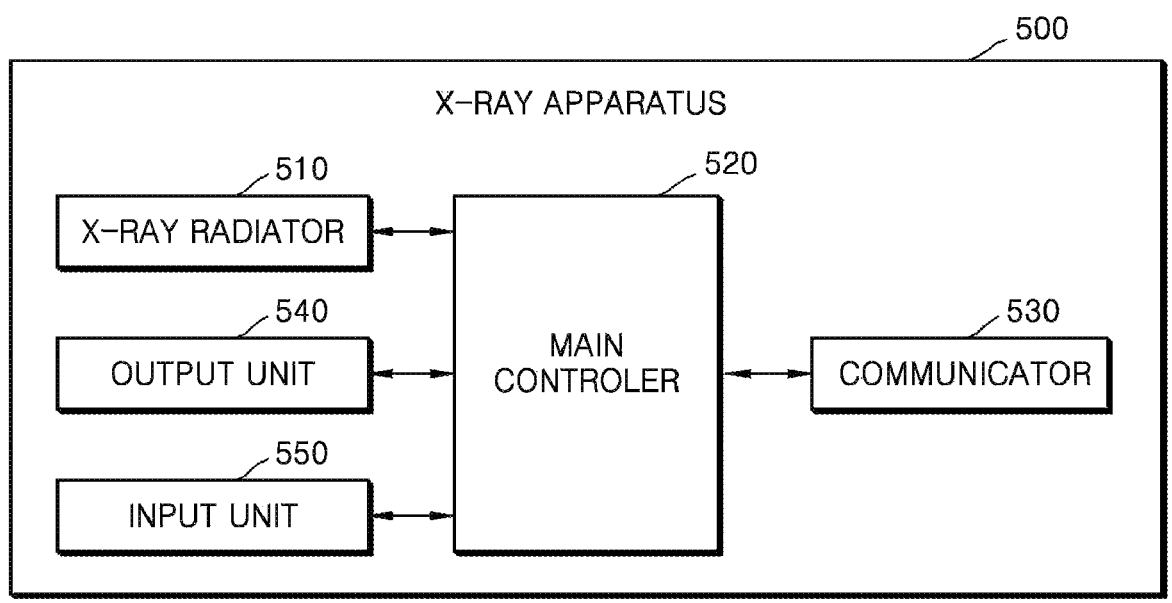
FIG. 5 is a block diagram of an X-ray apparatus according to an exemplary embodiment.

FIG. 5 is a block diagram of an X-ray apparatus 500 according to an exemplary embodiment.

The X-ray apparatus 500 may include an X-ray radiator 510, a main controller 520, a communicator 530, an output unit 540 (e.g., outputter), and an input unit 550 (e.g., inputter).

When the X-ray apparatus 500 of FIG. 5 is included in the X-ray system 1000 of FIG. 1, the X-ray apparatus 500 of FIG. 5 may correspond to the X-ray apparatus 100 of FIG. 1. In detail, the X-ray radiator 510, the main controller 520, the output unit 540, and the input unit 550 of the X-ray apparatus 500 of FIG. 5 may respectively correspond to the X-ray radiator 120, the controller 150, the output unit 141, and the input unit 142 of the X-ray apparatus 100 of FIG. 1. The communicator 530 of the X-ray apparatus 500 of FIG. 5 may communicate with an X-ray detector by wires or wirelessly and may also communicate with an external apparatus via the network 150 of FIG. 1. Thus, a repeated description thereof will be omitted.

The aforementioned components will now be described in detail.

The X-ray radiator 510 may generate X-rays and radiate the X-rays to an object.

The main controller 520 may acquire orientation information of the X-ray radiator 510 and orientation information of an X-ray detector.

For example, the orientation information of the X-ray radiator 510 may include at least one selected from position information of the X-ray radiator 510 and directional information thereof, and the orientation information of the X-ray detector may include at least one selected from position information of the X-ray detector and directional information thereof.

For example, the position information of the X-ray radiator 510 may be a position vector of the X-ray radiator 510 in a global coordinate system that is expressed as an inertial frame in which an arbitrary location within an X-ray imaging space is the origin. This feature will be described in greater detail later with reference to FIG. 10. Different pieces of position information of the X-ray radiator 510 may be acquired between when the X-ray apparatus 500 is the fixed type X-ray apparatus 200 and when the X-ray apparatus 500 is the mobile X-ray apparatus 300.

For example, in a global coordinate system that is expressed as an inertial frame in which an arbitrary location within an X-ray imaging space is the origin, when the X-ray apparatus 500 is the fixed type X-ray apparatus 200, the position information of the X-ray radiator 510 may be an absolute position vector of the X-ray radiator 510 acquired by using any of various sensors or apparatuses.

Alternatively, in a global coordinate system that is expressed as an inertial frame in which an arbitrary location within an X-ray imaging space is the origin, when the X-ray apparatus 500 is the mobile X-ray apparatus 300, the position information of the X-ray radiator 510 may be obtained by calculating a relative position vector of the X-ray radiator 510 based on an absolute position vector of the mobile X-ray apparatus acquired by using any of various sensors or apparatuses.

The directional information of the X-ray radiator 510 may also include information related to a directional orientation of the X-ray and information related to the X-ray irradiation region.

For example, the directional information of the X-ray radiator 510 may be a normal vector of one surface of the X-ray radiator 510. The directional information of the X-ray radiator 510 may also be a volume vector group corresponding to the X-ray irradiation region of the X-ray radiator 510 at various positions. This feature will be described in greater detail later with reference to FIGS. 12 and 15.

For example, the position information of the X-ray detector may be a position vector of the X-ray detector in a global coordinate system that is expressed as an inertial frame in which an arbitrary location within an X-ray imaging space is the origin. The position information of the X-ray detector may also include a volume vector group configured to include a plurality of position vectors existing within a predetermined distance from the position vector of the X-ray detector. This feature will be described in greater detail later with reference to FIGS. 9 and 16.

The directional information of the X-ray detector may also include information indicating a facing direction of the X-ray radiator 510. For example, the directional information of the X-ray detector may be a normal vector of one surface of the X-ray detector. In this case, the direction of the normal vector of the X-ray detector may be perpendicular to a plane irradiated by an X-ray. The direction of the normal vector may also be perpendicular to a plane formed by the photo-detecting substrate 410. This feature will be described in greater detail later with reference to FIG. 13.

In this case, the orientation information of the X-ray radiator 510 or the orientation information of the X-ray detector may be directly acquired by the main controller 520 of the X-ray apparatus 500 by using any of various types of sensors or apparatuses. For example, the orientation information of the X-ray radiator 510 or the orientation information of the X-ray detector may be acquired in real time by a camera or may be acquired using a wireless frequency.

In this case, since orientation information of an object within an X-ray imaging space may be acquired using any of various sensors or apparatuses according to various methods, such as common methods of using light, electromagnetic waves, sound waves, a magnetic field, and an electric field, a method of acquiring the orientation information of the X-ray radiator 510 or the orientation information of the X-ray detector is not limited to a specific method.

The orientation information of the X-ray detector may also be acquired by using reference orientation information which is initial orientation information of the X-ray detector and using information related to orientation of the X-ray detector that the communicator 530 of the X-ray apparatus 500 has received from the X-ray detector. In this case, the main controller 520 acquires the orientation information of the X-ray detector.

The reference orientation information includes at least one selected from reference position information of the X-ray detector and reference directional information thereof, and may be acquired based on initial orientation of the X-ray detector.

For example, when an X-ray detector is coupled to a stand type receptor or a table type receptor, the reference position information of the X-ray detector may be position information corresponding to a location of the stand type receptor or the table type receptor.

Also, when an X-ray detector is coupled to a stand type receptor or a table type receptor, the reference directional information of the X-ray detector may be directional information corresponding to a direction of the stand type receptor or the table type receptor.

The reference orientation information may be reset when the X-ray detector is coupled to a stand type receptor or a table type receptor.

In this connection, the X-ray apparatus 500 updates or resets the reference orientation information of the X-ray detector when the X-ray detector is coupled to a stand type receptor or a table type receptor, thereby minimizing the number of accumulated errors which occur in the calculation performed by the main controller 520 to acquire the orientation information of the X-ray detector.

For example, information related to orientation of the X-ray detector may be information that corresponds to a movement of the X-ray detector sensed by a sensor unit of the X-ray detector on the basis of the reference orientation information. In this case, a detector controller of the X-ray detector may acquire the information related to the orientation of the X-ray detector. This feature will be described in greater detail later with reference to FIG. 6.

In this case, the information related to orientation of the X-ray detector that is acquired in a detector controller of the X-ray detector may be transmitted via a communicator 630 (see FIG. 6) of the X-ray detector and may be received via the communicator 530 of the X-ray apparatus 500. The main controller 520 may select the X-ray detector based on the orientation information of the X-ray radiator 510 and the orientation information of the X-ray detector. The main controller 520 may activate the X-ray detector based on the orientation information of the X-ray radiator 510 and the orientation information of the X-ray detector.

For example, the orientation information of the X-ray radiator 510 may include at least one selected from position information of the X-ray radiator 510 and directional information thereof, and the orientation information of the X-ray detector may include at least one selected from position information of the X-ray detector and directional information thereof.

In this case, the main controller 520 may select the X-ray detector based on the position information of the X-ray radiator 510 and the position information of the X-ray detector. The main controller 520 may also select the X-ray detector based on the directional information of the X-ray radiator 510 and the directional information of the X-ray detector. The main controller 520 may also select the X-ray detector based on the position information of the X-ray radiator 510 and the directional information of the X-ray detector. The main controller 520 may also select the X-ray detector based on the directional information of the X-ray radiator 510 and the position information of the X-ray detector. This feature will be described in greater detail later with reference to FIGS. 11, 14, and 17-19. Also, many different combinations of information may be used to select the x-ray detector, and the exemplary embodiments are not limited to any particular combination. According to an exemplary embodiment, any type of spatial information, which is information describing characteristics of the X-ray radiator 510 and the X-ray detector(s) in a spatial dimension, may be used to select the X-ray detector. The spatial information may include orientation information, directional information, position information, movement information, etc.

According to another exemplary embodiment, the main controller 520 may acquire motion information of the X-ray detector, which is related to a motion of the X-ray detector.

For example, the motion information of the X-ray detector may include at least one selected from motion time information corresponding to a time section (e.g., time period) during which the X-ray detector moves, and motion direction information corresponding to a direction in which the X-ray detector moves.

For example, the motion information of the X-ray detector may be directly acquired by the main controller 520 of the X-ray apparatus 500 by using any of various sensors or apparatuses.

For example, the motion information of the X-ray detector may be acquired in real time by a camera or may be acquired using a wireless frequency.

In this case, since motion information of an object within an X-ray imaging space may be acquired using any of various sensors or apparatuses according to any of various methods, such as common methods of using light, electromagnetic waves, sound waves, a magnetic field, and an electric field, a method of acquiring the motion information of the X-ray detector is not limited to a specific method.

The motion information of the X-ray detector may be directly acquired by the main controller 520 by receiving from the X-ray detector information about a motion sensed by any of various sensors including, for example, an acceleration sensor mounted on the X-ray detector. It is understood that exemplary embodiments are not limited to using an acceleration sensor to sense motion, and may instead use other types of sensors configured to sense motion (e.g., GPS).

Alternatively, the motion information of the X-ray detector may be acquired by the detector controller included in the X-ray detector, based on the information about a motion of the X-ray detector sensed by the sensor unit included in the X-ray detector.

The motion information of the X-ray detector may be generated by a sensor controller included in the sensor unit and may be transmitted directly to the X-ray apparatus or transmitted to the X-ray apparatus via the detector controller of the X-ray detector.

The main controller 520 may control the communicator 530 to transmit to the X-ray detector a control signal generated in X-ray imaging sequence.

For example, the control signal includes at least one selected from a signal for informing selection of the X-ray detector and a signal for activating the X-ray detector.

In this case, the signal for informing selection of the X-ray detector may be generated based on the orientation information of the X-ray radiator 510 and the orientation information of the X-ray detector, in the main controller 520 of the X-ray apparatus 500.

Also, the signal for activating the X-ray detector may be generated based on the orientation information of the X-ray radiator 510 and the orientation information of the X-ray detector in the main controller 520 of the X-ray apparatus 500. Accordingly, the X-ray detector may be automatically activated based on the control signal.

For example, the control signal may be generated based on the position information of the X-ray radiator 510 and the position information of the X-ray detector. Also, the control signal may be generated based on the directional information of the X-ray radiator 510 and the directional information of the X-ray detector. Also, the control signal may be generated based on the directional information of the X-ray radiator 510 and the position information of the X-ray detector. Also, the control signal may be generated based on the position information of the X-ray radiator 510 and the directional information of the X-ray detector.

As another option, the signal for activating the X-ray detector may be generated based on a user's input.

For example, the X-ray detector and the X-ray apparatus 500 may be connected to each other by wire or wirelessly, based on the signal for informing selection of the X-ray detector. The X-ray detector may be activated based on the signal for activating the X-ray detector which is input through an input unit 560 of the X-ray apparatus.

For example, the X-ray detector may be activated in response to a radiation-prepare signal input via the radiation switch or a special input according to the user's input conducted before the radiation-prepare signal is received.

According to another exemplary embodiment, the control signal generated by the main controller 520 may be generated based on the orientation information of the X-ray radiator 510 and the motion information of the X-ray detector.

For example, the control signal may be generated based on the orientation information of the X-ray radiator 510 and motion time information corresponding to a time section in which a motion of the X-ray detector occurs.

The control signal may also be generated based on the orientation information of the X-ray radiator 510 and motion directional information corresponding to a direction in which the X-ray detector moves.

The control signal may include at least one selected from a signal for informing selection of the X-ray detector and a signal for activating the selected X-ray detector. The control signal may also include a signal for generating identification information of the selected X-ray detector.

The signal for informing selection of the X-ray detector may be generated based on the orientation information of the X-ray radiator 510 and the motion information of the X-ray detector, in the main controller 520 of the X-ray apparatus 500. In other words, based on the orientation information of the X-ray radiator 510 and the motion information of the X-ray detector, the X-ray detector that is used in X-ray imaging may be selected.

The X-ray detector that is used in X-ray imaging may be selected based on the orientation information of the X-ray radiator 510 and the motion time information corresponding to the time section during which the X-ray detector moves.

For example, an X-ray detector that has moved last from among a plurality of X-ray detectors that have a predetermined relationship with the orientation of the X-ray radiator 510 may be selected.

For example, the motion time information corresponding to the time section in which a motion of the X-ray detector occurs may include information about a first time when the motion of the X-ray detector has been sensed and information about a second time when consecutive motions are no longer sensed.

In this case, an X-ray detector with respect to which the second time when consecutive motions are no longer sensed is most recent may be selected from among a plurality of X-ray detectors.

The X-ray detector that is used in X-ray imaging may also be selected based on the orientation information of the X-ray radiator 510 and the motion directional information corresponding to a direction in which the X-ray detector moves.

For example, if it is determined that at least one selected from a starting point and an ending point of a movement trajectory corresponding to a movement of an X-ray detector is adjacent to a location of the X-ray radiator 510, the X-ray detector may be selected as the X-ray detector that is used in X-ray imaging.

Also, if it is determined that the movement trajectory of an X-ray detector is included in an X-ray irradiation region irradiated by the X-ray radiator 510, the X-ray detector may be selected as the X-ray detector that is used in X-ray imaging.

The X-ray detector and the X-ray apparatus may be connected to each other by wire or wirelessly, based on the signal for informing selection of the X-ray detector. The X-ray detector may be activated based on the signal for activating the X-ray detector which is input through an input unit 560 of the X-ray apparatus. In other words, the signal for activating the X-ray detector may be generated based on a user's input. The user's input may be input in many different ways, e.g., through a keyboard, through verbal commands, through gestures, etc.

The signal for activating the selected X-ray detector may be generated based on the orientation information of the X-ray radiator 510 and the motion information of the X-ray detector, in the main controller 520 of the X-ray apparatus 500.

For example, as described above, the signal for informing selection of the X-ray detector may include a signal for automatically activating the selected X-ray detector.

In this case, based on the control signal generated based on the orientation information of the X-ray radiator 510 and the motion information of the X-ray detector, the X-ray detector that is used in X-ray imaging may be automatically selected and activated.

The control signal may be used to generate the identification information of the selected X-ray detector. Throughout the description of the exemplary embodiments, the term "identification information" of the X-ray detector may refer to predetermined information about the X-ray detector, which distinguishes the X-ray detector from other X-ray detectors.

For example, the identification information of the X-ray detector may include unique information of the X-ray detector that distinguishes the X-ray detector from not only other types of X-ray detectors but also from the same type of X-ray detectors as that of the X-ray detector, and may further include at least one selected from specification information of the X-ray detector that distinguishes the X-ray detector from other types of X-ray detectors and mounting position information of the X-ray detector. The identification information will now be described in more detail.

For example, the control signal may be used to generate the identification information of the X-ray detector selected based on the orientation information of the X-ray radiator 510 and the motion information of the X-ray detector.

The identification information of the selected X-ray detector may be generated based on motion information of the selected X-ray detector. For example, the identification information of the selected X-ray detector may be generated based on motion directional information corresponding to a direction in which the selected X-ray detector moves.

For example, the identification information of the X-ray detector may include mounting position information of the X-ray detector. In this case, the mounting position information of the X-ray detector may include at least one selected from information indicating that the X-ray detector has been combined with a stand type receptor, information indicating that the X-ray detector has been combined with a table type receptor, and information indicating that the X-ray detector is combined with no receptors.

For example, when the direction in which the X-ray detector moves is a vertical direction of a certain trajectory, the identification information of the X-ray detector may include the information indicating that the X-ray detector has been combined with a stand type receptor.

Alternatively, when the direction in which the X-ray detector moves is a horizontal direction of a certain trajectory, the identification information of the X-ray detector may include the information indicating that the X-ray detector has been combined with a table type receptor.

Alternatively, when the direction in which the X-ray detector moves is neither a vertical direction nor a horizontal of a certain trajectory, the identification information of the X-ray detector may include the information indicating that the X-ray detector is combined with no receptors.

The output unit 540 of the X-ray apparatus 500 may display an icon of the X-ray detector that represents identification information of the X-ray detector. This feature will be described in greater detail later with reference to FIGS. 27-31.

Accordingly, an X-ray apparatus 500 generates identification information of an X-ray detector selected based on orientation information of an X-ray radiator 510 and motion information of the X-ray detector, and displays an icon representing the identification information on an output unit 540 of the X-ray apparatus 500. Accordingly, the user easily recognizes the X-ray detector that is used for imaging, even without spending much time and effort.

The main controller 520 of the X-ray apparatus 500 may directly generate the identification information of the selected X-ray detector, based on the motion information of the selected X-ray detector. For example, the identification information of the X-ray detector, including the mounting position information of the X-ray detector, may be directly generated by the main controller 520.

The main controller 520 of the X-ray apparatus 500 may receive identification information directly acquired by a detector controller included in the selected X-ray detector, from the selected X-ray detector.

The identification information of the X-ray detector may be generated by a sensor controller included in the sensor unit of the X-ray detector and may be transmitted directly to the X-ray apparatus 500 or transmitted to the X-ray apparatus 500 via the detector controller of the X-ray detector.

The main controller 520 may control an operation of the X-ray radiator 510, based on the identification information of the selected X-ray detector.

For example, the identification information of the X-ray detector may include type information and size information of the X-ray detector.

For example, types of X-ray detectors may be categorized into X-ray detectors using a direct detection method, which detects X-rays by reading out an electron-hole pair that is generated through a direct reaction with the X-rays, and X-ray detectors using an indirect detection method that detects and reads out light into which X-rays are converted via a scintillator.

For example, when an X-ray detector having a size of 17 inch×17 inch is selected instead of an X-ray detector having a size of 14 inch×17 inch, at least one of an X-ray radiation direction and an X-ray irradiation region of the X-ray radiator 510 may be adjusted in correspondence with the size of the selected X-ray detector. Moreover, the X-ray source of the X-ray radiator 510 may rotate and move in a front direction, a rear direction, a left direction, a right direction, an up direction, or a down direction or at a certain angle in order for the X-ray radiator 510 to radiate an X-ray having the same size as the size of the selected X-ray detector. In addition, a size of a collimator included in the X-ray radiator 510 may be automatically adjusted in order for the X-ray radiator 510 to radiate an X-ray having the same size as the size of the selected X-ray detector. In other words, when the X-ray detector having the size of 17 inch×17 inch is selected, the size of the collimator may be automatically adjusted such that an area of X-rays reaching the X-ray detector is equal to the size of 17 inch×17 inch, and when the X-ray detector having the size of 14 inch×17 inch is selected, the size of the collimator may be automatically adjusted such that an area of X-rays reaching the X-ray detector is equal to the size of 14 inch×17 inch.

The main controller 520 may control an operation of the X-ray radiator 510, based on the orientation information of the selected X-ray detector.

For example, a main controller 520 of an X-ray apparatus 500 according to an exemplary embodiment may control orientation of an X-ray radiator 510 so that the X-ray radiator 510 and a selected X-ray detector may face each other, based on orientation information of the selected X-ray detector.

In this case, the position of the X-ray radiator 510 may be controlled based on the position information of the selected X-ray detector, and the direction of the X-ray radiator 510 may be controlled based on the direction information of the selected X-ray detector. The direction of the X-ray radiator 510 may be controlled based on the position information of the selected X-ray detector, and the position of the X-ray radiator 510 may be controlled based on the direction information of the selected X-ray detector. The position and direction of the X-ray radiator 510 may be simultaneously or sequentially controlled based on the position information and direction information of the selected X-ray detector. This feature will be described in greater detail later with reference to FIG. 22.

The main controller 520 of the X-ray apparatus 500 according to an exemplary embodiment may determine whether the X-ray radiator 510 and the X-ray detector 600 face each other, based on orientation information of the X-ray radiator 510 and orientation information of the X-ray detector 600.

For example, the orientation information of the X-ray radiator 510 or the orientation information of the X-ray detector 600 may be directly acquired by the main controller 520 of the X-ray apparatus 500 by using any of various sensors or apparatuses.

The main controller 520 of the X-ray apparatus 500 may receive the orientation information of the X-ray detector acquired by the detector controller included in the X-ray detector, based on the orientation of the X-ray detector sensed by the sensor unit included in the X-ray detector.

For example, the orientation information of the X-ray radiator 510 may include at least one selected from position information of the X-ray radiator 510 and directional information thereof, and the orientation information of the X-ray detector may include at least one selected from position information of the X-ray detector and directional information thereof.

The orientation information of the X-ray detector may be generated by a sensor controller included in the sensor unit and may be transmitted directly to the X-ray apparatus or transmitted to the X-ray apparatus via the detector controller of the X-ray detector.

When the X-ray radiator 510 is adjacent to the X-ray detector 600, the main controller 520 of the X-ray apparatus 500 may determine that the X-ray radiator 510 and the X-ray detector 600 face each other. For example, when a difference between distances indicated by the position information of the X-ray radiator 510 and the position information of the X-ray detector 600 is within a predetermined range, the main controller 520 may determine that the X-ray radiator 510 and the X-ray detector 600 face each other. This feature will be described in greater detail later with reference to FIG. 11.

When the direction in which the X-ray radiator 510 radiates an X-ray is opposite to the direction in which the X-ray detector 600 is oriented, the main controller 520 of the X-ray apparatus 500 may determine that the X-ray radiator 510 and the X-ray detector 600 face each other. For example, when a difference between angles indicated by the direction information of the X-ray radiator 510, indicating the radiation direction of an X-ray, and the direction information of the X-ray detector 600, indicating the direction in which the X-ray detector 600 faces the X-ray radiator 510, is within a predetermined range, the main controller 520 may determine that the X-ray radiator 510 and the X-ray detector 600 face each other. This feature will be described in greater detail later with reference to FIG. 14.

When a region irradiated by the X-ray radiated by the X-ray radiator 510 is adjacent to the position of the X-ray detector 600, the main controller 520 of the X-ray apparatus 500 may determine that the X-ray radiator 510 and the X-ray detector 600 face each other. For example, when the position information of the X-ray detector 600 is included in the direction information of the X-ray radiator 510, representing the region irradiated by the X-ray, the main controller 520 may determine that the X-ray radiator 510 and the X-ray detector 600 face each other. This feature will be described in greater detail later with reference to FIGS. 17-19.

When the main controller 520 determines that the X-ray radiator 510 and the X-ray detector 600 face each other, the main controller 520 may select the X-ray detector 600. When the main controller 520 determines that the X-ray radiator 510 and the X-ray detector 600 face each other, the main controller 520 may activate the X-ray detector 600.

On the other hand, when the X-ray radiator 510 and the X-ray detector 600 do not face each other, the main controller 520 of the X-ray apparatus 500 may control orientation of the X-ray radiator 510 so that the X-ray radiator 510 and the X-ray detector 600 may face each other, based on the orientation information of the X-ray detector 600.

The main controller 520 may also control the output unit 540 of the X-ray apparatus 500 or the output unit of the X-ray detector to output information about whether the X-ray radiator 510 and the X-ray detector 600 face each other via the output unit 540 of the X-ray apparatus 500 or the output unit of the X-ray detector.

For example, the output unit 640 of the X-ray detector 600 may include an LCD, an LED, a light-emitting device, and the like, and, when the X-ray radiator 510 and the X-ray detector 600 do not face each other, the output unit 640 may flicker to instruct a user to change orientation of the X-ray detector 600 or the X-ray radiator 510. Accordingly, when a user tries to perform X-ray imaging on an object, imaging errors may be reduced and thus the amount of exposure of the object to radiation during X-ray imaging may be reduced. In addition, more accurate X-ray images may be obtained.

The output unit 640 of the X-ray detector 600 may include an LCD, an LED, a light-emitting device, and the like, and, when the X-ray radiator 510 and the X-ray detector 600 face each other, the output unit 640 may flicker to inform a user that the X-ray detector 600 is ready for X-ray imaging.

The output unit 640 of the X-ray detector 600 may inform a user that the X-ray detector 600 is selected for X-ray imaging.

The output unit 640 may include a sound output unit, and may output sound instead of flickering, to inform a user that the X-ray detector 600 is ready for X-ray imaging. The sound may be many different types, such as a spoken sound or phrase, a sound effect (e.g., chimes, bells, etc.), or another type of sound.

According to another exemplary embodiment, the main controller 520 may display an icon corresponding to the identification information of the selected X-ray detector 600 to the output unit 540 of the X-ray apparatus 500, based on the identification information of the selected X-ray detector 600.

For example, the identification information may include unique information of the X-ray detector 600 that distinguishes the X-ray detector 600 from not only other types of X-ray detectors but also from the same type of X-ray detectors as that of the X-ray detector 600. In detail, the unique information may include at least one selected from a serial number (SN) of the X-ray detector 600 and an Internet Protocol (IP) address thereof. In detail, the SN of the X-ray detector 600 is a unique identifier given during the manufacture of the X-ray detector 600. The IP address of the X-ray detector may include an IP address value that is to be used when the X-ray detector and an access point (AP) communicate with each other.

The identification information may also include specification information of the X-ray detector that distinguishes the X-ray detector from other types of X-ray detectors. In detail, the specification information may include at least one selected from the size of the X-ray detector and the type of a receptor with which the X-ray detector 600 is combinable. As described above, different sizes and shapes of X-ray detectors may be suitable for X-ray imaging according to parts of an object to be imaged. Accordingly, the size of the X-ray detector 600 may be a criterion on which a user selects an X-ray detector suitable for imaging.

The specification information of the X-ray detector is not limited to the size of the X-ray detector and the type of a receptor with which the X-ray detector is combinable. For example, the specification information of the X-ray detector may further include information about a material detected by the X-ray detector, information about a geometrical structure of the X-ray detector, and information about a method in which the X-ray detector measures a signal. In detail, the information about the material detected by the X-ray detector may include a light detection type and a direct charge-detection type, as well as other types of information indicating characteristics of the material. The information about the geometrical structure of the X-ray detector includes a one-dimensional (1D) array type and a two-dimensional (2D) area type. The information about the method in which the X-ray detector measures a signal may include an integral detection type and a coefficient detection type.

In addition to the unique information and the specification information, the identification information of the X-ray detector may further include, for example, mounting position information of the X-ray detector and identification information of a network to which the X-ray detector has been connected.

According to another exemplary embodiment, the main controller 520 may display an icon corresponding to the mounting position information of the selected X-ray radiator to the output unit 540 of the X-ray apparatus 500, based on the mounting position information of the selected X-ray detector.

For example, the mounting position information of the X-ray detector may include at least one selected from information indicating that the X-ray detector has been combined with a stand type receptor, information indicating that the X-ray detector has been combined with a table type receptor, and information indicating that the X-ray detector is combined with no receptors.

When the mounting position information of the X-ray detector includes the information indicating that the X-ray detector has been combined with a stand type receptor, an icon representing that the X-ray detector has been combined with a stand type receptor may be displayed on the output unit 540.

When the mounting position information of the X-ray detector includes the information indicating that the X-ray detector has been combined with a table type receptor, an icon representing that the X-ray detector has been combined with a table type receptor may be displayed on the output unit 540.

When the mounting position information of the X-ray detector includes the information indicating that the X-ray detector is combined with no receptors, an icon representing that the X-ray detector is a portable X-ray detector may be displayed on the output unit 540.

This feature will be described in greater detail later with reference to FIGS. 27-31.

The communicator 530 of the X-ray apparatus 500 includes a transmitter and a receiver and may be connected to the network by wire or wirelessly to communicate with the X-ray detector or the workstation.

For example, when the X-ray detector is selected by the main controller 520, the communicator 530 of the X-ray apparatus 500 may be connected to the network by wire or wirelessly to communicate with the selected X-ray detector. In other words, the X-ray apparatus 500 and the X-ray detector may be connected to each other by wire or wirelessly. When they are connected to each other wirelessly, a device for synchronizing clock signals with each other may be further included in the X-ray apparatus 500 and the X-ray detector.

In this case, the X-ray detector and the X-ray apparatus 500 transmit or receive signals that are generated during an X-ray imaging operation to each other, via a network.

For example, the main controller 520 may transmit a prepare signal to the X-ray detector so that the X-ray detector may prepare to detect the X-ray transmitted through the object. The X-ray detector prepares to detect the X-ray in response to the prepare signal, and when the preparing for the detection is finished, the X-ray detector transmits a ready signal to the main controller 520.

Also, when the high voltage generator 121 receives the prepare signal from the main controller 520, the high voltage generator 121 may transmit a prepare signal to the X-ray detector so that the X-ray detector may prepare to detect the X-ray transmitted through the object. In this case, the X-ray detector prepares to detect the X-ray in response to the prepare signal, and when the preparing for the detection is finished, the X-ray detector transmits a ready signal to the high voltage generator 121. The high voltage generator 121 also transmits the ready signal received from the X-ray detector to the main controller 520.

Also, the X-ray apparatus 500 may transmit a signal for informing selection of the X-ray detector to the X-ray detector, and the X-ray detector may be activated based on the signal received from the X-ray apparatus 500. In this case, the X-ray detector may prepare to receive X-ray irradiation during X-ray imaging.

The communicator 530 may transmit a signal for activating the X-ray detector selected to be used for imaging, to the selected X-ray detector.

Also, the communicator 530 may receive information related to the orientation of the X-ray detector from the X-ray detector.

For example, the information related to the orientation of the X-ray detector may be information that is related to a movement of the X-ray detector sensed by the sensor unit of the X-ray detector on the basis of the reference orientation information of the X-ray detector. In this case, the information related to the orientation of the X-ray detector may be acquired by a detector controller of the X-ray detector.

In addition, a user may register at least one X-ray detector in the main controller 520 of the X-ray apparatus 500 in advance before X-ray imaging is performed, and thus the main controller 520 may acquire identification (ID) information and IP information of the X-ray detector in advance. Accordingly, the X-ray apparatus 500 may communicate with the X-ray detector via a wired or wireless network.

In this case, the main controller 520 receives information related with orientation information including at least one selected from position information and direction information from the at least one X-ray detector via the communicator 530, and then transmits a control signal to a selected X-ray detector via the communicator 530. Alternatively, when the X-ray detector transmits the orientation information to the main controller 520, the X-ray detector may also transmit the ID information of the X-ray detector.

According to another exemplary embodiment, the communicator 530 may receive information related to the movement of the X-ray detector from the X-ray detector.

For example, motion information related to the movement of the X-ray detector may be acquired based on a direction in which the X-ray detector moves.

The motion information related to the movement of the X-ray detector may be acquired based on a time section in which the X-ray detector moves.

The main controller 520 may acquire the identification information of the X-ray detector, and more particularly, the mounting position information of the X-ray detector, based on the motion information of the X-ray detector.

According to another exemplary embodiment, the communicator 530 may receive identification information directly acquired by the detector controller included in the X-ray detector, from the X-ray detector.

The identification information of the X-ray detector may be generated by a sensor controller included in the sensor unit of the X-ray detector and may be transmitted directly to the X-ray apparatus 500 or transmitted to the X-ray apparatus 500 via the detector controller of the X-ray detector.

The identification information directly acquired by the X-ray detector may include mounting position information of the X-ray detector. The X-ray apparatus 500 may further include the output unit 540 and the input unit 550.

The output unit 540 may display information about a plurality of X-ray detectors that are selectable by a user.

Alternatively, the output unit 540 may output pieces of information about only a plurality of X-ray detectors located in a predetermined direction from the X-ray radiator 510.

In this case, the pieces of information about the X-ray detectors may be arranged according to a predetermined arrangement criterion and then output. The predetermined arrangement criterion may be flexible and based on numerous different types of considerations.

The input unit 550 may receive a selection signal for selecting at least one X-ray detector from among the plurality of X-ray detectors displayed on the output unit 540.

This feature will be described in greater detail later with reference to FIG. 20.

According to another exemplary embodiment, the output unit 540 may display an icon corresponding to identification information of an X-ray detector.

For example, an icon corresponding to mounting position information of the X-ray detector selected for X-ray imaging may be displayed on the output unit 540.

Accordingly, an X-ray apparatus 500 generates identification information of an X-ray detector selected based on orientation information of an X-ray radiator and motion information of the X-ray detector, and displays an icon representing the identification information on an output unit 540 of the X-ray apparatus 500. Accordingly, the user easily recognizes the X-ray detector that is used for imaging, even without spending much time and effort.

The input unit 550 may be formed as a touch pad. In detail, the input unit 550 may include a touch pad coupled with a display panel included in the output unit 540. The output unit 540 displays a user interface (UI) image on the display panel. When a user inputs a command by touching a certain point on the UI image, the touch pad may sense the input operation and recognize the command input by the user.

In detail, when the input unit 550 includes a touch pad and the user touches a certain point on the UI image, the input unit 550 senses the touched point. Then, the input unit 550 may transmit sensed information to the main controller 520. Thereafter, the main controller 520 may recognize a user's request or command corresponding to the sensed information and may perform the recognized user's request or command.

Figure 6:
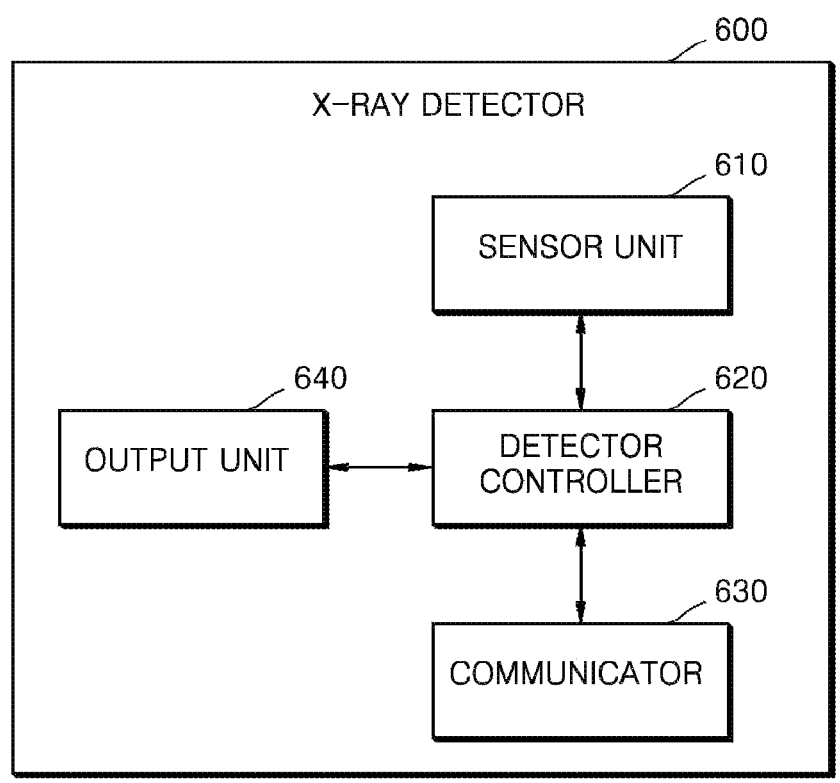
FIG. 6 is a block diagram of an X-ray detector according to an exemplary embodiment.

FIG. 6 is a block diagram of an X-ray detector 600 according to an exemplary embodiment.

The X-ray detector 600 may include a sensor unit 610 (e.g., sensor), a detector controller 620, and a communicator 630. The X-ray detector 600 may further include an output unit 640. The X-ray detector 600 may be at least one selected from a wired X-ray detector and a wireless X-ray detector.

When the X-ray detector 600 is included in the X-ray system 1000 of FIG. 1, the X-ray detector 600 may correspond to the detector 130 of FIG. 1. As described above, the X-ray detector 600 may be separated from the X-ray apparatus 100 of FIG. 1. Thus, a repeated description thereof will be omitted.

The aforementioned components will now be described in detail.

The sensor unit 610 may sense orientation of the X-ray detector 600.

For example, the sensor unit 610 may sense a movement of the X-ray detector 600, based on initial orientation information of the X-ray detector 600.

For example, the sensing unit 610 may include a gyroscope sensor, a geomagnetic sensor, an inertial measurement unit (IMU), an accelerometer, a magnetometer, or a global positioning system (GPS) sensor. Many other types of sensors may also be used as the sensing unit 610.

In this case, since the movement of the X-ray detector 600 may be sensed using any of various sensors according to any of various methods that are widely used in the art, a method of sensing the movement of the X-ray detector 600 is not limited to a specific method.

The detector controller 620 may acquire orientation information of the X-ray detector 600, based on the orientation of the X-ray detector 600 sensed in the sensor unit 610.

For example, the orientation information of the X-ray detector 600 includes at least one selected from position information of the X-ray detector 600 and directional information of the X-ray detector 600.

The detector controller 620 may acquire the orientation information of the X-ray detector 600, based on reference orientation information, which is initial orientation information of the X-ray detector 600 received from an X-ray apparatus, and information related to the orientation of the X-ray detector 600 according to the movement of the X-ray detector 600 sensed by the sensor unit 610 of the X-ray detector 600.

In this case, the information related to the orientation of the X-ray detector 600 according to the movement of the X-ray detector 600 may be acquired in the detector controller 620.

For example, the information related to the orientation of the X-ray detector 600 according to the movement of the X-ray detector 600 includes at least one selected from the information related to the position of the X-ray detector 600 according to the movement of the X-ray detector 600 and the information related to the directional of the X-ray detector 600 according to the movement of the X-ray detector 600.

Also, the information related to the orientation of the X-ray detector 600 according to the movement of the X-ray detector 600, may be information indicating at least one selected from a moving direction, a moving angle, and a moving distance of the X-ray detector 600 which have been sensed by the sensor unit 610 based on the reference orientation information which is the initial orientation information of the X-ray detector 600. In this case, the information related to the orientation of the X-ray detector 600 according to the movement of the X-ray detector 600 may be information indicating at least one selected from a moving direction, a moving angle, and a moving distance of the X-ray detector 600 which have been detected by the sensor unit 610 at certain time intervals. For example, the certain time interval may include a time interval such as one second, ten seconds, or one minute. Many other time intervals may also be used.

In this case, since the information related to the orientation of the X-ray detector 600 according to a movement of the X-ray detector 600 may be sensed using any of various sensors according to any of various methods that are widely used in the art, a method of sensing information related to the orientation of the X-ray detector 600 according to a movement of the X-ray detector 600 is not limited to a specific method.

According to another exemplary embodiment, the sensor unit 610 may sense a movement of the X-ray detector 600.

The sensor unit 610 may sense at least one selected from a movement direction of the X-ray detector 600 and a time section during which the X-ray detector 600 moves.

For example, when the sensor unit 610 is an acceleration sensor, the acceleration sensor may sense variation information of an acceleration according to a movement of the X-ray detector 600.

An acceleration sensor may measure a dynamic force, such as acceleration, a vibration, or an impact, of a moving body by processing an output signal. Acceleration sensors may be classified into an inertial acceleration sensor, a gyro-acceleration sensor, and a silicon semiconductor acceleration sensor, and a seismic intensity scale or a clinometer may also be considered as types of acceleration sensor.

For example, an acceleration sensor has three axes, and an input value of each axis may be used as an acceleration vector.

For example, the time section in which the movement of the X-ray detector 600 occurs is a time period during which the movement of the X-ray detector 600 is detected, and is obtained by measuring a time period during which variation information of acceleration is sensed by the acceleration sensor.

The movement direction of the X-ray detector 600 denotes a direction of a movement trajectory in which the X-ray detector 600 has moved during the time section in which the movement of the X-ray detector 600 occurs. Thus, at least one selected from the moving direction, the moving angle, and the moving distance of the X-ray detector 600 may be sensed by the sensor unit 610.

In this case, the detector controller 620 may acquire motion information of the X-ray detector 600, based on a movement of the X-ray detector 600 sensed by the sensor unit 610.

For example, the motion information of the X-ray detector 600 may include at least one selected from motion time information corresponding to a time section during which the X-ray detector 600 moves, and motion direction information corresponding to a movement direction of the X-ray detector 600.

The detector controller 620 may acquire motion time information of the X-ray detector 600, based on a time section during which a movement of the X-ray detector 600 sensed by the sensor unit 610 occurs.

For example, the motion time information corresponding to the time section during which the X-ray detector moves may include information about a first time at which a movement of the X-ray detector has been sensed and information about a second time at which consecutive movements are no longer sensed.

The detector controller 620 may also acquire motion directional information of the X-ray detector 600, based on a direction of the movement of the X-ray detector 600 sensed by the sensor unit 610.

The motion directional information of the X-ray detector 600 may be acquired based on at least one selected from a moving distance, a moving direction, and a moving distance of the X-ray detector 600 which have been sensed by the sensor unit 610. In other words, the motion directional information of the X-ray detector 600 may include information about the direction of a movement trajectory in which the X-ray detector 600 has moved during the time section in which the movement of the X-ray detector 600 occurs.

In this case, since the motion information of the X-ray detector 600 may be sensed using any of various sensors according to any of various methods that are widely used in the art, a method of sensing motion information of the X-ray detector 600 is not limited to a specific method.

The communicator 630 includes a transmitter and a receiver.

The communicator 630 may transmit the orientation information of the X-ray detector 600 to the X-ray apparatus via a wireless network.

For example, the orientation information of the X-ray detector 600 includes at least one selected from position information of the X-ray detector 600 and directional information of the X-ray detector 600.

According to another exemplary embodiment, the communicator 630 may transmit the motion information of the X-ray detector 600 to the X-ray apparatus.

In this case, the communicator 630 may be controlled to transmit the motion information of the X-ray detector 600 to the X-ray apparatus before receiving a control signal from the X-ray apparatus.

The communicator 630 may also transmit identification information of the X-ray detector 600 to the X-ray apparatus.

The communicator 630 may receive a control signal from the X-ray apparatus.

The detector controller 620 may control the X-ray detector 600 to be activated, according to the control signal received by the communicator 630.

For example, the control signal received by the communicator 630 includes at least one selected from a signal for informing selection of the X-ray detector 600 and a signal for activating the X-ray detector 600.

Also, when the X-ray detector 600 is activated, the X-ray detector 600 may prepare to acquire an X-ray image. For example, the X-ray detector may prepare to reset a photodetector or to receive a radiated X-ray from an X-ray radiator included in the X-ray apparatus. Activation of the X-ray detector 600 is not limited to this example.

For example, when the X-ray detector 600 is in a sleep mode, the X-ray detector 600 is changed into a normal mode when receiving a notification signal for informing selection of the X-ray detector 600 from the X-ray apparatus. In this case, the X-ray detector 600 normalizes a clock signal of the detector controller 620, and a photodetector of the X-ray detector 600 may perform a reset operation (flushing) at faster intervals than in the sleep mode.

As another example, soon after previous X-ray imaging is performed, the X-ray detector 600 maintains a normal mode. In this case, a reset cycle of the photodetector may be adjusted in accordance with a current X-ray imaging stage. Other operations for preparing for X-ray imaging may be performed.

As another example, the X-ray detector 600 may be connected to the X-ray apparatus via a wireless network based on the signal for informing selection of the X-ray detector 600 from the X-ray apparatus. In this case, the X-ray detector may be activated based on the user's input through an input unit of the X-ray apparatus.

For example, a user may input, via the input unit of the X-ray apparatus, an input for X-ray radiation. For example, in response to a radiation-prepare signal input via a radiation switch of the X-ray apparatus, the X-ray detector 600 prepares to detect X-rays, and the preparation for the detection is completed.

At this time, when the X-ray detector 600 receives a radiation command via the radiation switch, the X-ray detector 600 may receive radiated X-rays and generate X-ray image data of an object. The generated X-ray image data may be transmitted to a main controller of the X-ray apparatus via the communicator 630 of the X-ray detector 600.

In other words, the X-ray detector 600 may be activated in response to a radiation-prepare signal input via the radiation switch or a special input conducted before the radiation-prepare signal is received.

Accordingly, the user may easily image an object even without spending much time and effort in selecting an X-ray detector that is used for imaging from among a plurality of X-ray detectors.

According to another exemplary embodiment, the detector controller 620 of the X-ray detector 600 may generate identification information of the X-ray detector 600 that is to be used for imaging.

For example, the identification information of the X-ray detector 600 may include mounting position information of the X-ray detector 600. In this case, the mounting position information of the X-ray detector 600 may include at least one selected from information indicating that the X-ray detector 600 has been combined with a stand type receptor, information indicating that the X-ray detector 600 has been combined with a table type receptor, and information indicating that the X-ray detector 600 is combined with no receptors. The mounting position information may also include other types of information, such as details related to the particular mounting configuration.

In this case, the mounting motion information of the X-ray detector 600 may be generated based on motion information related to the movement sensed by the sensor unit 610 of the X-ray detector 600.

For example, when the direction in which the X-ray detector 600 moves is a vertical direction of a certain trajectory, the identification information of the X-ray detector 600 may include the information indicating that the X-ray detector 600 has been combined with a stand type receptor.

On the other hand, when the direction in which the X-ray detector 600 moves is a horizontal direction of a certain trajectory, the identification information of the X-ray detector 600 may include the information indicating that the X-ray detector 600 has been combined with a table type receptor.

On the other hand, when the direction in which the X-ray detector 600 moves is neither a vertical direction nor a horizontal of a certain trajectory, the identification information of the X-ray detector 600 may include the information indicating that the X-ray detector 600 is combined with no receptors. As described above, the X-ray detector 600 may further include the output unit 640. The detector controller 620 may control the output unit 640 to display the information indicating whether the X-ray detector 600 has been selected and/or activated, according to the control signal received by the communicator 630.

Examples of the output unit 640 of the X-ray detector 600 may include an LCD, an LED, and a light-emitting device (for example, a light-emitting device which flickers when the X-ray detector 600 is activated) which are for outputting the information indicating whether the X-ray detector 600 has been selected and/or activated.

Also, when the X-ray detector receives the signal for informing selection of the X-ray detector, the detector controller may transmit a signal to the output unit 640 so that the output unit 640 output a predetermined sound or a mark and the object or the user may recognize whether the X-ray detector 600 has been selected to be used for imaging.

Also, when the X-ray detector receives the signal for activating the X-ray detector, the detector controller may transmit a signal to the output unit 640 so that the output unit 640 outputs a predetermined sound or a mark and the object or the user may recognize whether the X-ray detector 600 has been activated.

According to another exemplary embodiment, the X-ray detector 600 may control the output unit 640 to display identification information indicating mounting position information of the X-ray detector 600, according to the control signal received by the communicator 630.

For example, the mounting position information of the X-ray detector 600 may include at least one selected from information indicating that the X-ray detector 600 has been combined with a stand type receptor, information indicating that the X-ray detector 600 has been combined with a table type receptor, and information indicating that the X-ray detector 600 is combined with no receptors.

This feature will be described in greater detail later with reference to FIGS. 27-31.

Accordingly, the X-ray detector 600 generates identification information of an X-ray detector 600 selected based on orientation information of an X-ray radiator of the X-ray apparatus and motion information of the X-ray detector 600, and displays the identification information on the output unit 640 of the X-ray detector 600. Accordingly, the user easily recognizes the X-ray detector 600 that is used for imaging, even without spending much time and effort.

Figure 7:
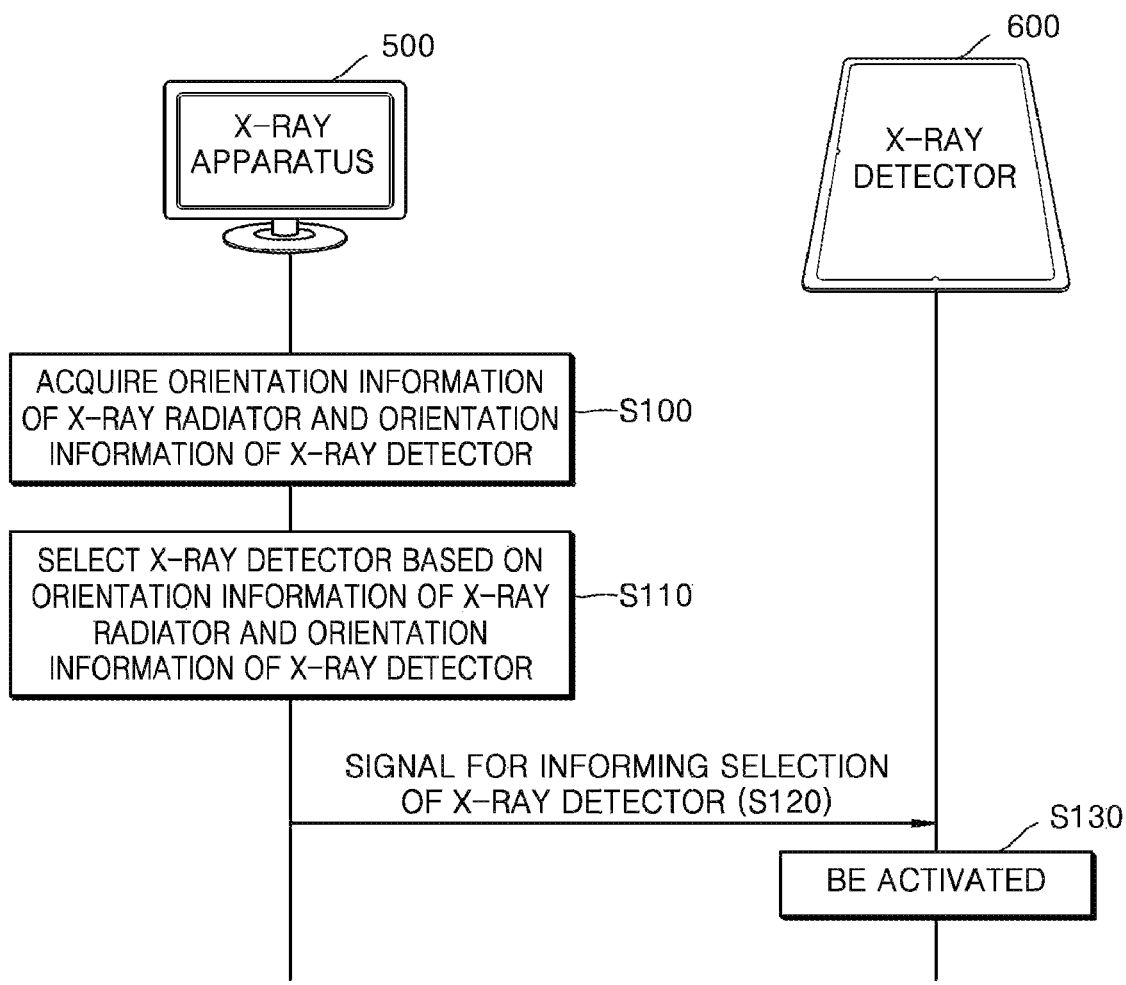
FIG. 7 is a diagram for describing respective operations of an X-ray apparatus and an X-ray detector according to an exemplary embodiment.

FIG. 7 is a diagram for describing respective operations of the X-ray apparatus 500 and the X-ray detector 600 according to an exemplary embodiment.

In operation S100, the X-ray apparatus 500 acquires orientation information of the X-ray radiator 510 and orientation information of the X-ray detector 600.

For example, the orientation information of the X-ray radiator 510 or the orientation information of the X-ray detector 600 may be directly acquired by the main controller 520 of the X-ray apparatus 500 by using any of various sensors or apparatuses.

The orientation information of the X-ray detector 600 may also be acquired by using reference orientation information which is initial orientation information of the X-ray detector 600 and using information related to orientation of the X-ray detector 600 that the communicator 530 of the X-ray apparatus 500 has received from the X-ray detector 600. In this case, the main controller 520 acquires the orientation information of the X-ray detector 600.

For example, the orientation information of the X-ray radiator 510 may include at least one selected from position information of the X-ray radiator 510 and directional information thereof, and the orientation information of the X-ray detector 600 may include at least one selected from position information of the X-ray detector 600 and directional information thereof.

In operation S110, the X-ray apparatus 500 selects the X-ray detector 600 based on the orientation information of the X-ray radiator 510 and the orientation information of the X-ray detector 600 acquired in operation S100. In operation S110, the X-ray apparatus 500 generates a signal for activating the X-ray detector 600 based on the orientation information of the X-ray radiator 510 and the orientation information of the X-ray detector 600 acquired in operation S100. Alternatively, the X-ray apparatus 500 may, based on the orientation information of the X-ray radiator 510 and the orientation information of the X-ray detector 600, determine not to select the X-ray detector 600. For example, if the orientation information of the X-ray radiator 510 and the orientation information of the X-ray detector 600 indicates that the relative orientation is not desirable (e.g., surfaces of the X-ray radiator 500 and the X-ray detector 600 are substantially misaligned), the X-ray apparatus 500 may determine not to select the X-ray detector 600. In this case, information (e.g., video or audio) may also be output indicating that the single X-ray detector 600 has not been selected.

In operation S120, the X-ray apparatus 500 transmits, to the X-ray detector 600 selected in operation 110, a signal for informing that the X-ray detector 600 has been selected. In operation S120, the X-ray apparatus 500 transmits the signal generated in operation S110 to the X-ray detector 600.

In operation S130, the X-ray detector 600 is activated based on the signal received from the X-ray apparatus 500 in operation 120.

Operations S110, S120 and S130 are exemplarily described above as operations for determining whether or not to select and activate a single X-ray detector 600. In such a single-detector scenario, many different techniques and conditions may be used to determine whether or not to select and activate the X-ray detector 600. For example, after acquiring the orientation information and motion information of the X-ray detector 600, the main controller 520 of the X-ray apparatus 500 may compare the orientation information to an orientation threshold value, or may compare the motion information to a motion threshold value, and may determine whether or not to select and activate the X-ray detector 600 based on at least one of the comparisons. The orientation threshold value may, for example, indicate an alignment deviation angle between a detecting surface of the X-ray detector 600 and a surface of the X-ray radiator (e.g., 5°, 10°, 13°, etc.), where if the alignment deviates more than the alignment deviation angle, the X-ray apparatus 500 may determine that the X-ray apparatus 500 and the X-ray detector 600 are misaligned, and thus, the X-ray detector 600 is not selected. Furthermore, the motion threshold value may be a relative speed between the X-ray apparatus 500 and the X-ray detector 600, where if the motion exceeds the motion threshold value, the X-ray detector 600 is not selected. In addition to the orientation information and motion information, other types of information, such as position information, directional information, or information indicating hardware or software characteristics of the X-ray detector 600 and/or the X-ray apparatus 500, may also be used. Of course, it is understood that exemplary embodiments are not limited a single-detector scenario, and as described in detail below, exemplary embodiments may also be used to select an X-ray detector among a plurality of X-ray detectors.

Figure 8:
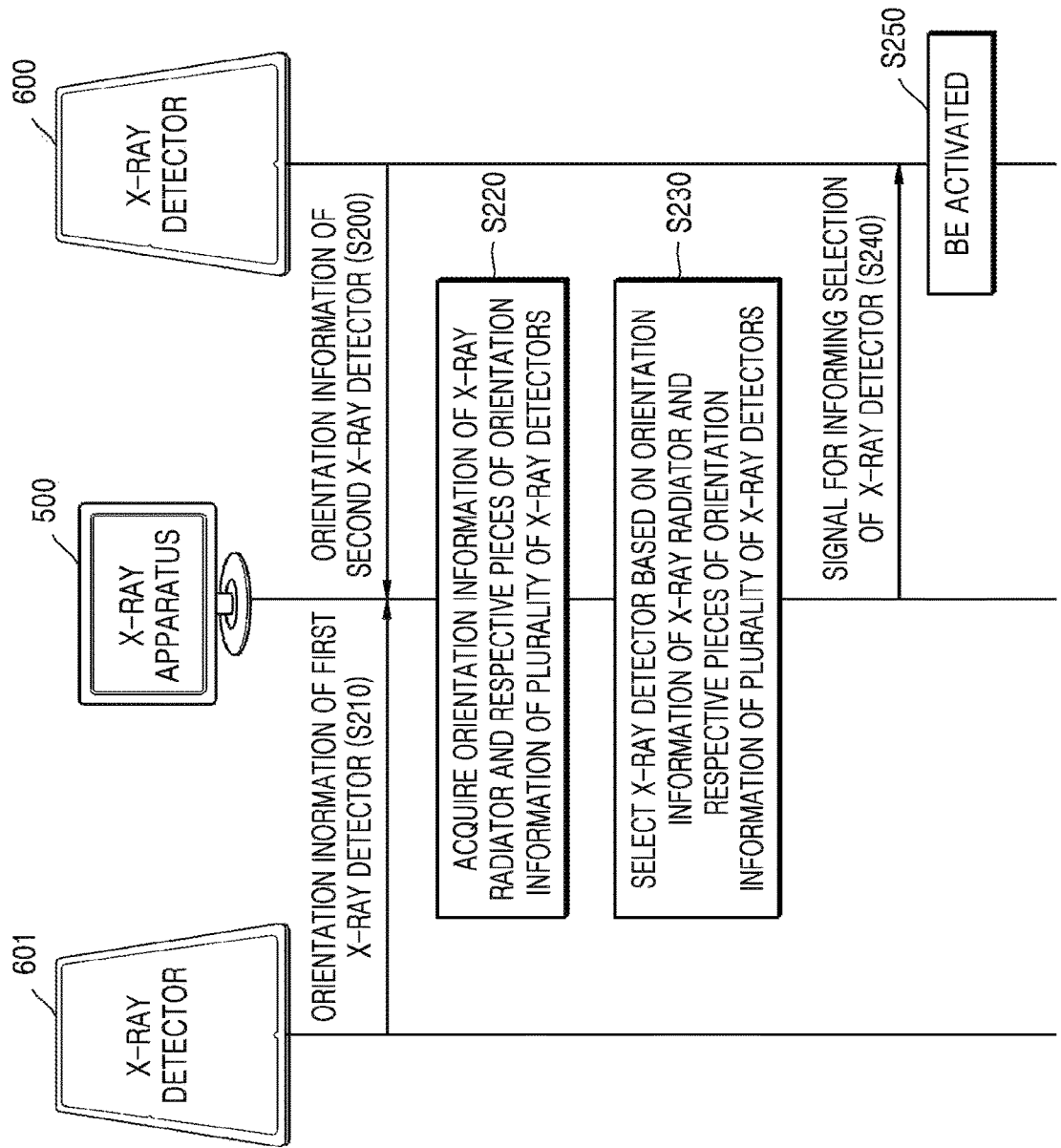
FIG. 8 is a diagram for describing respective operations of an X-ray apparatus and a plurality of X-ray detectors according to an exemplary embodiment.

FIG. 8 is a diagram for describing respective operations of the X-ray apparatus 500 and X-ray detectors 600 and 601 according to an exemplary embodiment.

Operations S230, S240 and S250 correspond to operations S110, S120, and S130 of FIG. 7, respectively, and thus detailed descriptions thereof will be omitted.

In operations S200 and S210, the X-ray apparatus 500 receives pieces of information related to the orientation of the X-ray detectors 600 and 601 from the X-ray detectors 600 and 601, respectively.

For example, the pieces of information related to the orientation of the X-ray detectors 600 and 601 may be acquired in relation to movements of the X-ray detectors 600 and 601 sensed by respective sensor units of the X-ray detectors 600 and 601, based on respective pieces of initial orientation information of the X-ray detectors 600 and 601. In this case, respective detector controllers of the X-ray detectors 600 and 601 directly acquire information related to the orientation of the X-ray detectors 600 and 601. For example, the orientation information of an X-ray detector includes at least one selected from position information of the X-ray detector and directional information of the X-ray detector.

In operation S220, the X-ray apparatus 500 acquires orientation information of the X-ray radiator 510 and respective pieces of orientation information of the plurality of X-ray detectors 600 and 601.

For example, the orientation information of the X-ray detector may also be acquired by using reference orientation information which is initial orientation information of the X-ray detector and using information related to orientation of the X-ray detectors in operation S200 and S210 that the communicator 530 of the X-ray apparatus 500 has received from the X-ray detectors. In this case, the reference orientation information includes at least one selected from reference position information of the X-ray detector and reference directional information thereof based on an initial orientation of the X-ray detector.

Figure 9:
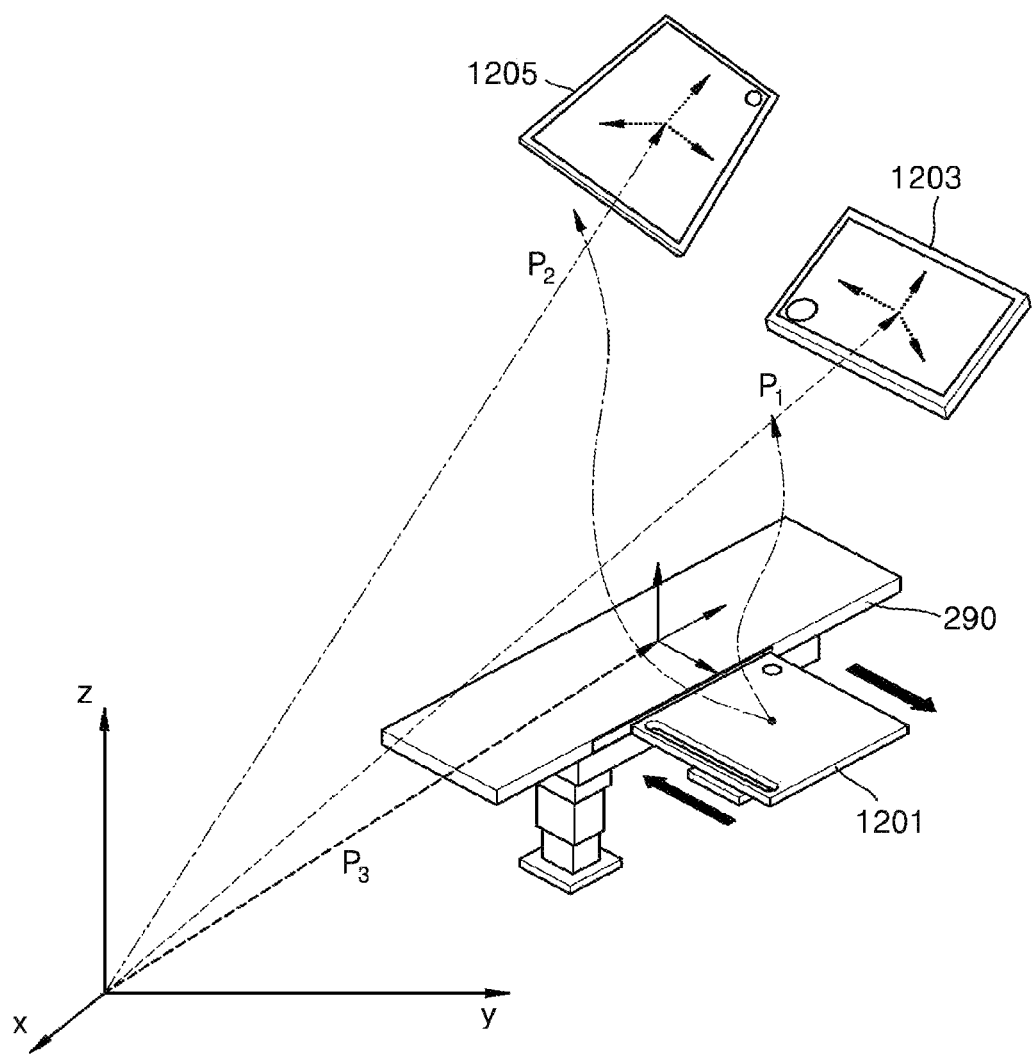
FIG. 9 illustrates an example in which the X-ray apparatus of FIG. 5 acquires position information of an X-ray detector.

FIG. 9 illustrates an example in which the X-ray apparatus 500 of FIG. 5 acquires position information of an X-ray detector.

As illustrated in FIG. 9, a plurality of X-ray detectors 1201, 1203, and 1205 may be freely dispersed within a single X-ray imaging space, and the X-ray apparatus 500 acquires respective position information of the X-ray detectors 1201, 1203, and 1205.

The X-ray detectors 1201, 1203, and 1205 may be pre-inserted into a stand type receptor or a table type receptor 290 of the X-ray apparatus 500 and thus may be used as fixed type X-ray detectors. Alternatively, the X-ray detectors 1201, 1203, and 1205 may be separated from the table type receptor 290 of the X-ray apparatus 500 and thus may be used as mobile X-ray detectors.

The X-ray detectors 1201, 1203, and 1205 may be movable to various locations within the X-ray imaging space. For example, as illustrated in FIG. 9, the X-ray detector 1201 having been coupled with the table type receptor 290 may be illustrated as the X-ray detector 1203 or 1205 that may exist at various locations, as the X-ray detector 1201 moves within the X-ray imaging space.

As illustrated in FIG. 9, respective pieces of position information of the X-ray detectors 1201, 1203, and 1205 may be position vectors of the X-ray detectors 1201, 1203, and 1205 in a global coordinate system that is expressed as an inertial frame in which an arbitrary location within an X-ray imaging space is the origin.

For example, a position vector $P_1$ of the center of the X-ray detector 1203 and a position vector $P_2$ of the center of the X-ray detector 1205 may be acquired as the respective pieces of position information of the X-ray detectors 1203 and 1205.

The position vector $P_1$ and the position vector $P_2$ may be directly acquired by the X-ray apparatus 500 by using any of various sensors or apparatuses.

In this case, since position information of an object within an X-ray imaging space may be acquired using any of various sensors or apparatuses according to any of various methods, such as common methods of using light, electromagnetic waves, sound waves, a magnetic field, and an electric field, a method of acquiring the respective position vectors of the X-ray detectors 1201, 1203, and 1205 is not limited to a specific method.

The position vector $P_1$ and the position vector $P_2$ may be acquired by using pieces of reference position information which are respective pieces of initial position information of the X-ray detectors 1203 and 1205 and using respective pieces of information that are related to orientation of the X-ray detectors 1203 and 1205 and received from the X-ray detectors 1203 and 1205.

For example, when the X-ray detectors 1201, 1203, and 1205 are coupled to the stand type receptor (not shown) or the table type receptor 290, respective pieces of reference location information of the X-ray detectors 1201, 1203, and 1205 may be position information corresponding to a location of the stand type receptor (not shown) or the table type receptor 290.

As illustrated in FIG. 9, the respective pieces of reference position information of the X-ray detectors 1201, 1203, and 1205 may be a position vector $P_3$ of the table type receptor 290 in a global coordinate system that is expressed as an inertial frame in which an arbitrary location within an X-ray imaging space is the origin.

For example, the position information of the stand type receptor or the table type receptor 290 in relation to one point of the X-ray imaging space (for example, a distal end of one corner of a bottom of the X-ray imaging space, a distal end of one corner of a ceiling of the X-ray imaging space, and a central point of the X-ray imaging space) may be predetermined. For example, the position information of the table type receptor 290 in relation to the distal end of one corner of the bottom of the X-ray imaging space may be determined as a coordinate value of (2, 2, 1). Alternatively, a coordinate value representing a position of the stand type receptor or the table type receptor 290 may be predetermined as the origin. For example, current position information of the table type receptor 290 within the X-ray imaging space may be predetermined as a coordinate value of (0, 0, 0).

In more detail, the X-ray detectors 1201, 1203, and 1205 may be inserted into the table type receptor 290 and thus the X-ray detector 1201 may be connected to the table type receptor 290. For example, a position of a magnet included in the table type receptor 290 may be detected by respective sensors (for example, a magnetometer) included in the X-ray detectors 1201, 1203, and 1205, and thus, whether the X-ray detectors 1201, 1203, and 1205 are connected to the table type receptor 290 may be determined.

When the X-ray detector 1201 is inserted into the table type receptor 290, the X-ray detector 1201 may be identified as a fixed-type X-ray detector. When the respective sensors of the X-ray detectors 1203 and 1205 are separated from the magnet included in the table type receptor 290, the X-ray detectors 1203 and 1205 may be identified as movable X-ray detectors.

By inserting the X-ray detector 1201 into the table type receptor 290, position information (for example, (1, 1, 0.5)) of the table type receptor 290 may be determined as the reference position information of the X-ray detector 1201.

For example, the detector controller may acquire the information related to position of the X-ray detector based on the position of the X-ray detector sensed by the sensor unit of the X-ray detector. Alternatively, a sensor controller may acquire the information related to position of the X-ray detector based on the position of the X-ray detector sensed by the sensor unit.

For example, the information related to the position of the X-ray detectors 1203 and 1205 received from the X-ray detectors 1203 and 1205 is the respective pieces of position variation information of the X-ray detectors 1203 and 1205 related with movements of the X-ray detectors 1203 and 1205 sensed by the respective sensor units of the X-ray detectors 1203 and 1205 based on the position information of the table type receptor 290, namely, the initial position information of each of the X-ray detectors 1203 and 1205.

In this case, since the pieces of position variation information of the X-ray detectors 1203 and 1205 according to movements of the X-ray detectors 1203 and 1205 may be sensed using any of various sensors, such as a gyroscope sensor, an IMU, an accelerometer, a GPS sensor, and a magnetometer, according to any of various methods that are widely used in the art, a method of sensing the pieces of position variation information of the X-ray detectors 1203 and 1205 according to movements of the X-ray detectors 1203 and 1205 is not limited to a specific method.

In this case, the position vectors $P_1$ and $P_2$ of the X-ray detectors 1203 and 1205 may be acquired using the position vector $P_3$ of the table type receptor 290, which is the initial position information of each of the X-ray detectors 1203 and 1205, and the respective pieces of position variation information received from the X-ray detectors 1203 and 1205.

The moving directions, the moving distances, or the moving angles of the X-ray detectors 1203 and 1205 may be calculated in order to acquire the respective pieces of position variation information based on the respective pieces of reference position information of the X-ray detectors 1203 and 1205. During this calculation, an error may be generated.

Thus, to reduce potential errors generated during calculation, the X-ray apparatus 500 may reset the reference position information of each of the X-ray detectors 1203 and 1205, which is the position information of the table type receptor 290, every time any of the X-ray detectors 1203 and 1205 is inserted into the table type receptor 290, thereby minimizing the number of accumulated errors which occur in the calculation performed to acquire the information related to the position of each of the X-ray detectors 1203 and 1205. The reference position information used in acquiring the information related to the position of the X-ray detector, is reset when the X-ray detector is coupled to a stand type receptor or a table type receptor.

Figure 10:
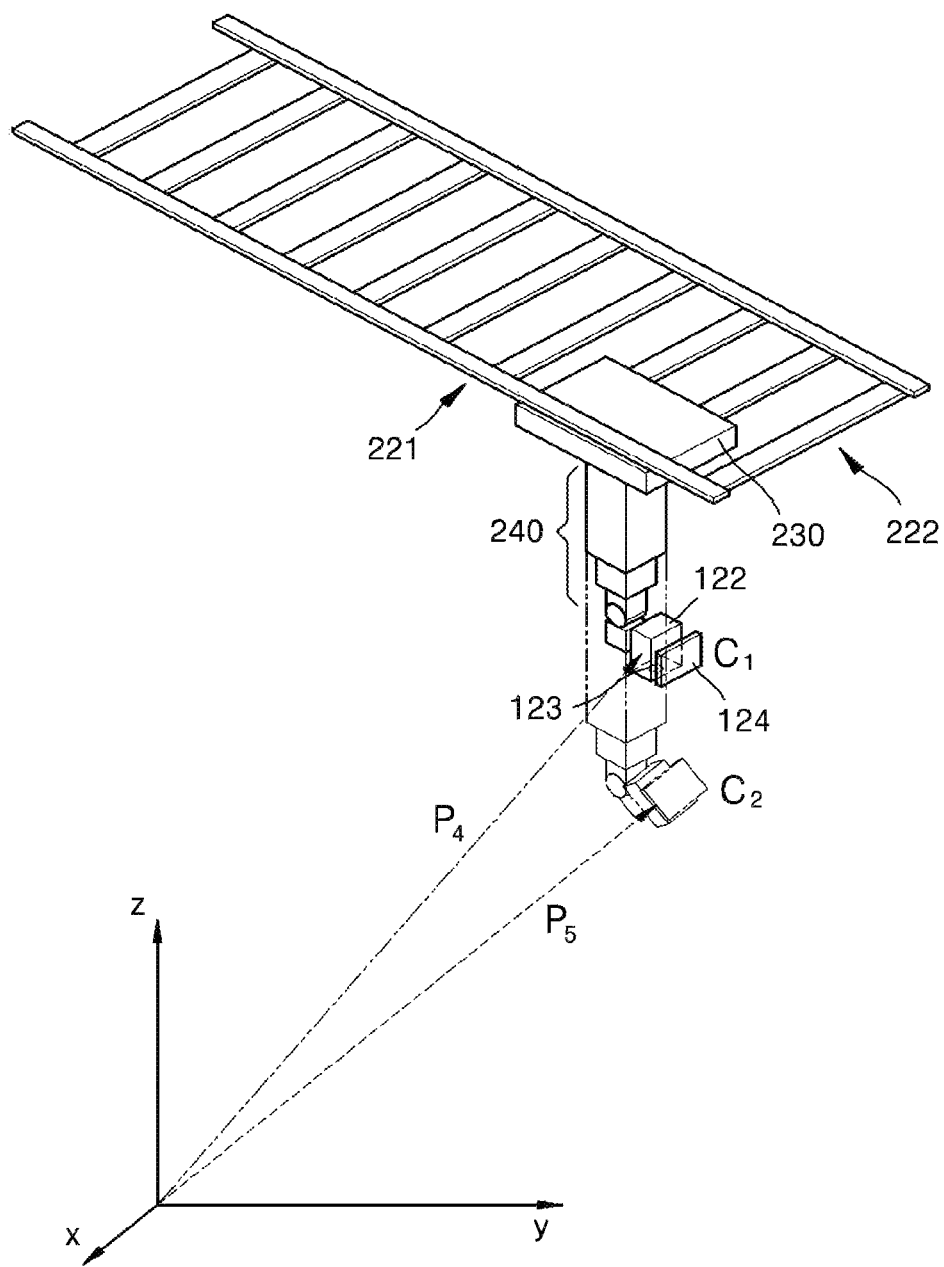
FIG. 10 illustrates an example in which the X-ray apparatus of FIG. 5 acquires position information of an X-ray radiator included therein.

FIG. 10 illustrates an example in which the X-ray apparatus 500 acquires position information of an X-ray radiator 510 included therein.

The X-ray radiator 510 may include the X-ray source 122 and/or the collimator 123.

As illustrated in FIG. 10, the X-ray source 122 in the X-ray imaging space may move to various positions $C_1$ and $C_2$ along the first and second guide rails 221 and 222 which are disposed at a certain angle. In other words, the X-ray source 122 may move in a front direction, a rear direction, a left direction, a right direction, an up direction, or a down direction or rotate at a certain angle. The X-ray source 122 may also move in an up direction or a down direction through the post frame 240 fixed to the moving carriage 230, in the X-ray imaging space. Also, the collimator 123 may move according to the moving of the X-ray source 122.

As illustrated in FIG. 10, the position information of the X-ray radiator 510 may be a position vector of the center of the X-ray radiator 510 in a global coordinate system that is expressed as an inertial frame in which an arbitrary location within an X-ray imaging space is the origin.

For example, when the X-ray radiator 510 is located at the position $C_1$, a position vector $P_4$ of the center of the X-ray radiator 510 may be acquired as the position information of the X-ray radiator 510. On the other hand, when the X-ray radiator 510 is located at the position $C_2$, a position vector $P_5$ of the center of the X-ray radiator 510 may be acquired as the position information of the X-ray radiator 510.

The position vector $P_4$ and the position vector $P_5$ may be directly acquired by the X-ray apparatus 500 by using any of various sensors or apparatuses.

In this case, since a position vector of an object within an X-ray imaging space may be acquired using any of various sensors or apparatuses according to any of various methods, such as common methods of using light, electromagnetic waves, sound waves, a magnetic field, and an electric field, a method of acquiring the position vector of the X-ray radiator 510 is not limited to a specific method.

Figure 11:
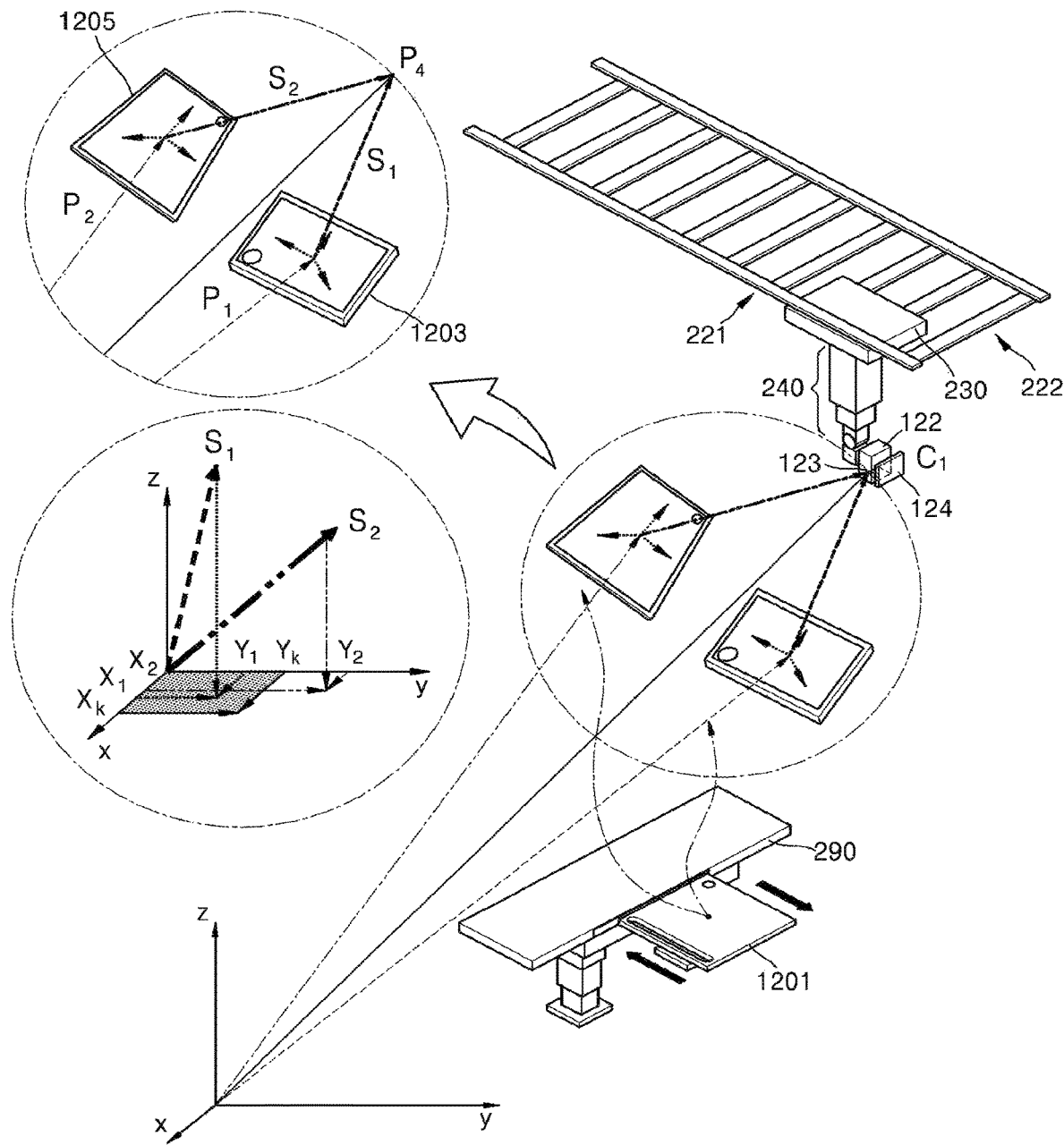
FIG. 11 illustrates an example in which the X-ray apparatus of FIG. 5 selects the X-ray detector based on position information of the X-ray radiator included therein and position information of the X-ray detector.

FIG. 11 illustrates an example in which the X-ray apparatus 500 of FIG. 5 selects the X-ray detector based on position information of the X-ray radiator 510 included therein and position information of the X-ray detector.

The X-ray apparatus 500 may select the X-ray detector when a difference between lengths of the position information of the X-ray radiator 510 and the position information of the X-ray detector is included in a predetermined range. In this case, the main controller 520 of the X-ray apparatus 500 may determine a relationship between the position information of the X-ray radiator 510 and the position information of the X-ray detector.

As illustrated in FIG. 11, the position information of the X-ray radiator 510 may be a position vector of the X-ray radiator 510 in a global coordinate system expressed as an inertial frame in which an arbitrary location within an X-ray imaging space is the origin and the position information of the X-ray detector may be a position vector of the X-ray detector in the global coordinate system. It is understood that many different types of coordinate systems may be employed in accordance with exemplary embodiments.

In this case, the X-ray apparatus 500 may select the X-ray detector based on a first position vector of the X-ray radiator 510 and second position vectors of the X-ray detectors 1203 and 1205.

As illustrated in FIG. 11, when the X-ray radiator 510 is located at the position $C_1$ within the X-ray imaging space, the first position vector of the X-ray radiator 510 may be the position vector $P_4$ of the center of the X-ray radiator 510.

The second position vectors of the X-ray detectors 1203 and 1205 may be the position vector $P_1$ of the center of the X-ray detector 1203 and the position vector $P_2$ of the center of the X-ray detector 1205, respectively.

When a relative vector which is a difference between the first position vector and each of the second position vectors is less than or equal to a predetermined value, an X-ray detector corresponding to the second position vector may be selected. Alternatively, a signal for activating the X-ray detector corresponding to the second position vector may be generated.

For example, the case where the relative vector is less than or equal to the predetermined value may include both a case where the magnitude of the relative vector is less than or equal to the predetermined value and a case where each coordinate value of the relative vector is less than or equal to the predetermined value.

As illustrated in FIG. 11, when the relative vector, which is the difference between the first position vector and the second position vector, satisfies the condition of $\{(X,Y) | 0<X<X_K, 0<Y<Y_K\}$, an X-ray detector corresponding to the second position vector may be selected. When the relative vector, which is the difference between the first position vector and the second position vector, satisfies the condition of $\{(X,Y) | 0<X<X_K, 0<Y<Y_K\}$, a signal for activating the X-ray detector corresponding to the second position vector may be generated.

As illustrated in FIG. 11, since an X-coordinate value $X_1$ and a Y-coordinate value $Y_1$ of a relative vector $S_1$, which is a difference between the first position vector $P_4$ and the second position vector $P_1$, satisfy the condition of $\{(X,Y) | 0<X<X_K, 0<Y<Y_K\}$, the X-ray detector 1203 may be selected. Alternatively, a signal for activating the X-ray detector 1203 may be generated.

On the other hand, since an X-coordinate value $X_2$ and a Y-coordinate value $Y_2$ of a relative vector $S_2$, which is a difference between the first position vector $P_4$ and the second position vector $P_2$, do not satisfy the condition of $\{(X,Y) | 0<X<X_K, 0<Y<Y_K\}$, the X-ray detector 1205 is not selected.

Figure 12:
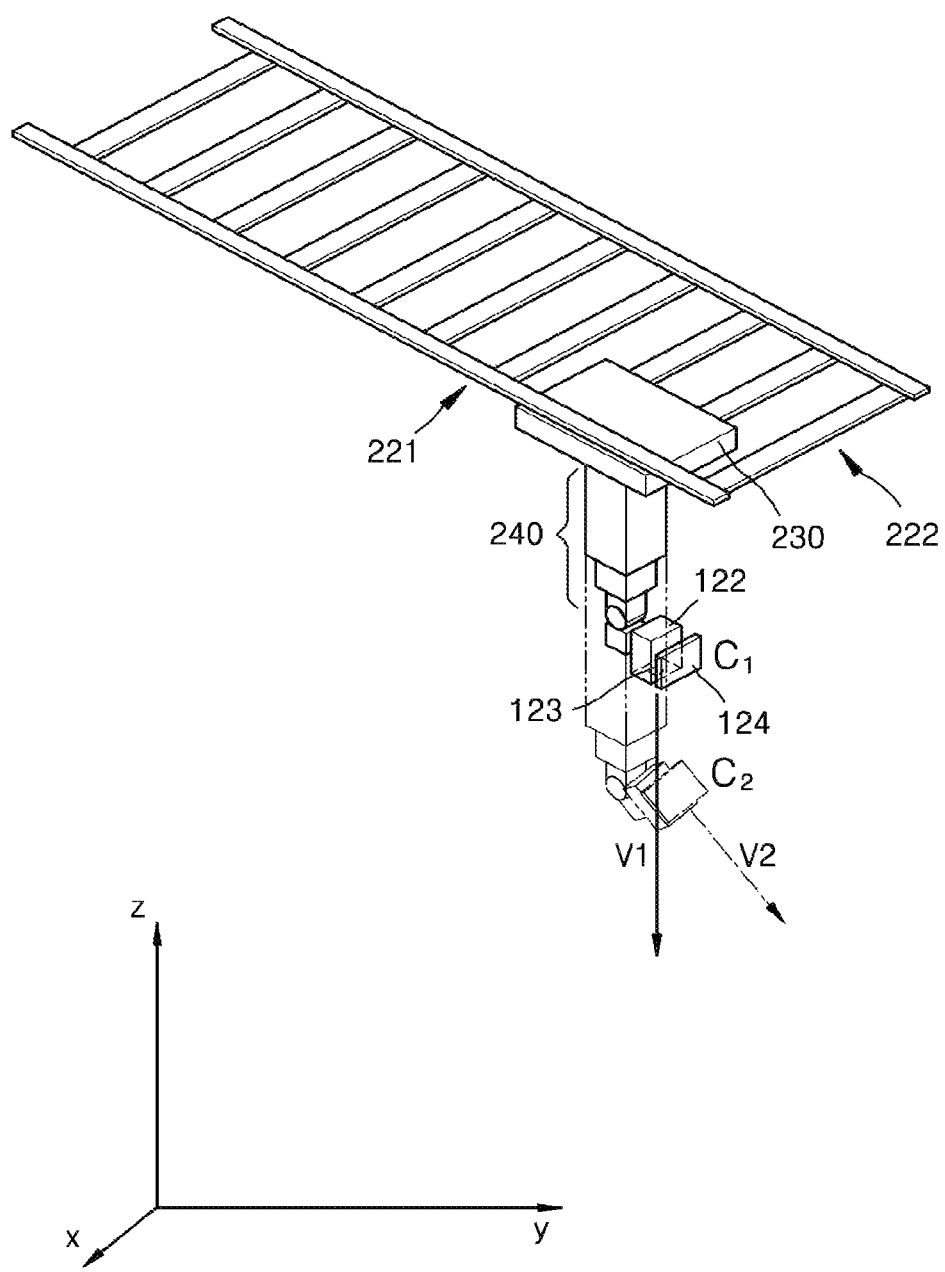
FIG. 12 illustrates an example in which the X-ray apparatus of FIG. 5 acquires directional information of the X-ray radiator included therein.

FIG. 12 illustrates an example in which the X-ray apparatus 500 of FIG. 5 acquires directional information of the X-ray radiator 510 included therein.

The directional information of the X-ray radiator 510 may be information related to a directional orientation in which an X-ray is radiated from the X-ray radiator 510.

As illustrated in FIG. 12, the directional information of the X-ray radiator 510 may be normal vectors $V_1$ and $V_2$ of one surface of the X-ray radiator 510.

For example, when the X-ray radiator 510 is located at the position $C_1$, the normal vector $V_1$ of one surface of the X-ray radiator 510 may be acquired as the directional information of the X-ray radiator 510. On the other hand, when the X-ray radiator 510 is located at the position $C_2$, the normal vector $V_2$ of the one surface of the X-ray radiator 510 may be acquired as the directional information of the X-ray radiator 510.

Figure 13:
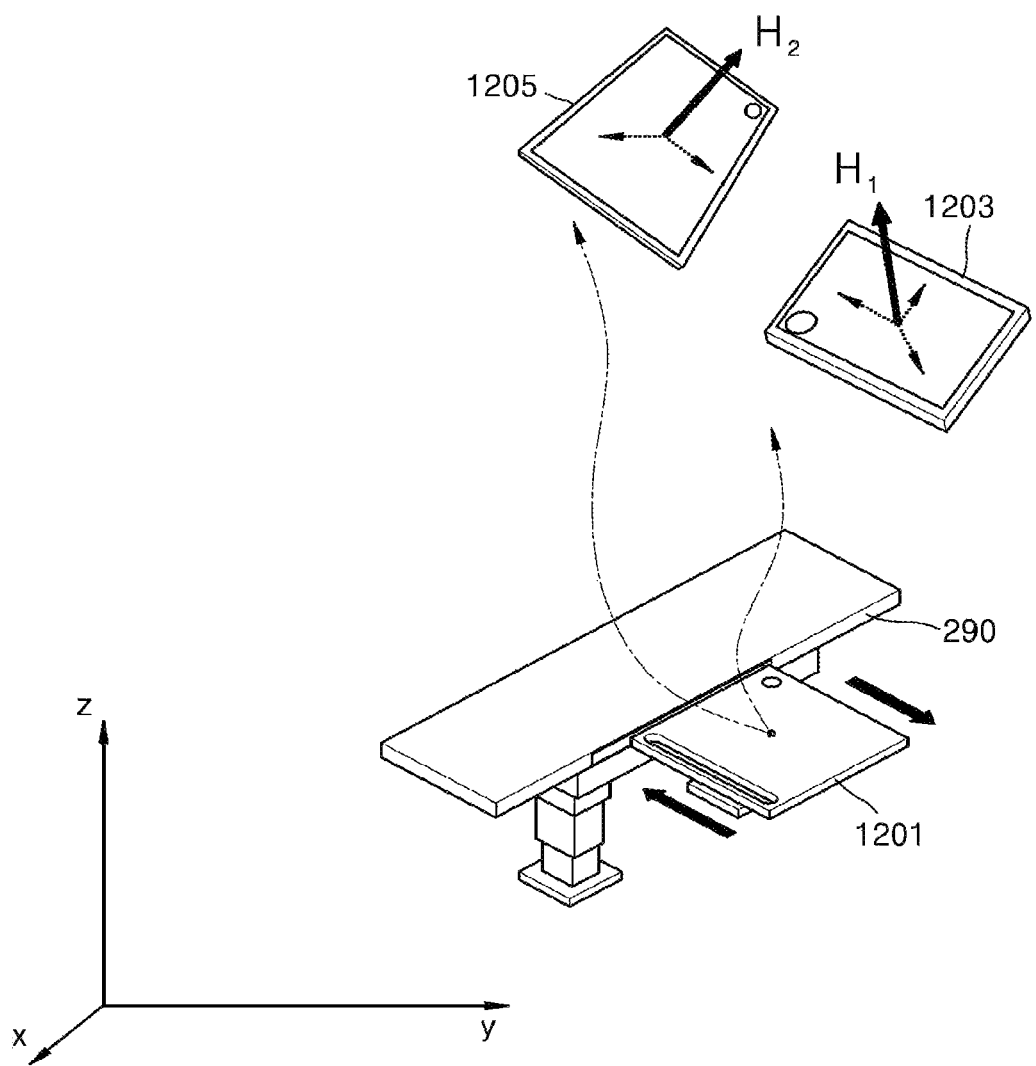
FIG. 13 illustrates an example in which the X-ray apparatus of FIG. 5 acquires directional information of an X-ray detector.

FIG. 13 illustrates an example in which the X-ray apparatus 500 of FIG. 5 acquires directional information of an X-ray detector.

The directional information of the X-ray detector may be information related to a facing direction of the X-ray radiator 510.

As illustrated in FIG. 13, the respective pieces of directional information of the X-ray detectors 1203 and 1205 may be a normal vector $H_1$ of one surface of the X-ray detector 1203 and a normal vector $H_2$ of one surface of the X-ray detector 1205. For example, a normal vector of an X-ray detector may be a direction perpendicular to a plane irradiated by an X-ray. The normal vector may also be a direction perpendicular to a plane formed by the photodetecting substrate 410.

Although the present exemplary embodiment illustrates an example using a normal vector, since the directional information of the X-ray detector may be acquired using any of various sensors provided on the X-ray detector according to any of various methods that are widely used in the art, such as a method of acquiring directional information by using a 3D angle based on the ground or the like, a method of acquiring the directional information of the X-ray detectors 1203 and 1205 is not limited to a specific method. Thus, methods of acquiring directional information may be used which do not rely on using a normal vector or any vectors at all.

Figure 14:
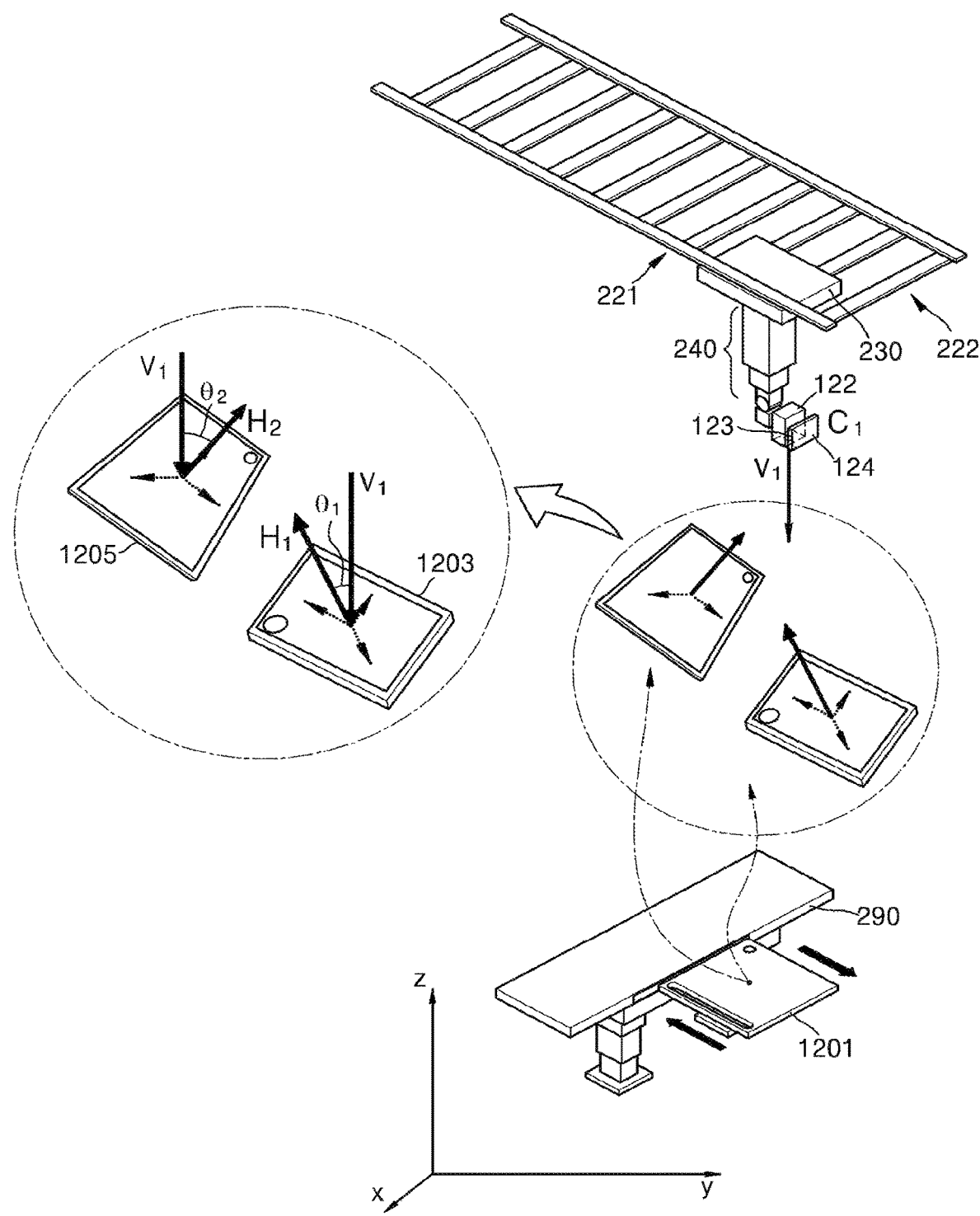
FIG. 14 illustrates an example in which the X-ray apparatus of FIG. 5 selects the X-ray detector based on directional information of the X-ray radiator included therein and directional information of the X-ray detector.

FIG. 14 illustrates an example in which the X-ray apparatus 500 of FIG. 5 selects the X-ray detector based on directional information of the X-ray radiator 510 included therein and directional information of the X-ray detector.

The X-ray apparatus 500 may select the X-ray detector when a difference between angles of the directional information of the X-ray radiator 510 indicating a directional orientation of the X-ray and the directional information of the X-ray detector indicating a facing direction of the X-ray radiator 510 is included in a predetermined range. In this case, the main controller 520 of the X-ray apparatus 500 may determine a relationship between the directional information of the X-ray radiator 510 and the directional information of the X-ray detector.

For example, as illustrated in FIG. 14, the directional information of the X-ray radiator 510 may be a first normal vector on a surface of the X-ray radiator 510, and the directional information of the X-ray detector may be a second normal vector on a surface of the X-ray detector.

For example, the first normal vector of the X-ray radiator 510 may be a direction in which an X-ray is radiated, and the second normal vector of the X-ray detector may be a direction perpendicular to a plane irradiated by an X-ray. In other words, the second normal vector may be a direction perpendicular to a plane formed by the photodetecting substrate 410.

In this case, the X-ray apparatus 500 may select the X-ray detector based on the first normal vector of the X-ray radiator 510 and second normal vectors of the X-ray detectors 1203 and 1205.

As illustrated in FIG. 14, when the X-ray radiator 510 is located at the position $C_1$ within the X-ray imaging space, the first normal vector of the X-ray radiator 510 may be the normal vector $V_1$ of one surface of the X-ray radiator 510.

The second normal vectors of the X-ray detectors 1203 and 1205 may be the normal vector $H_1$ of the one surface of the X-ray detector 1203 and the normal vector $H_2$ of the one surface of the X-ray detector 1205, respectively.

In this case, when a difference between angles of the first and second normal vectors is included in a predetermined range (e.g., less than 30 deg., or less than 15 deg., as desired), an X-ray detector corresponding to the second normal vector may be selected.

As illustrated in FIG. 14, since an angle difference $\theta_1$ between the first normal vector $V_1$ and the second normal vector $H_1$ is included in the range of less than 30 deg., the X-ray detector 1203 corresponding to the second normal vector $H_1$ may be selected. Since the angle difference $\theta_1$ between the first normal vector $V_1$ and the second normal vector $H_1$ is included in the range of less than 30 deg., the X-ray detector 1203 corresponding to the second normal vector $H_1$ may be activated. For example, the predetermined range may be between 0 deg and 30 deg., or more preferably between 0 deg and 15 deg. Exemplary embodiments are not limited to these ranges, however, and the ranges may, for example, be greater than 30 deg.

Alternatively, since an angle difference $\theta_2$ between the first normal vector $V_1$ and the second normal vector $H_2$ is not included in the range of 15 deg. or 30 deg., the X-ray detector 1205 corresponding to the second normal vector H2 may not be selected.

Figure 15:
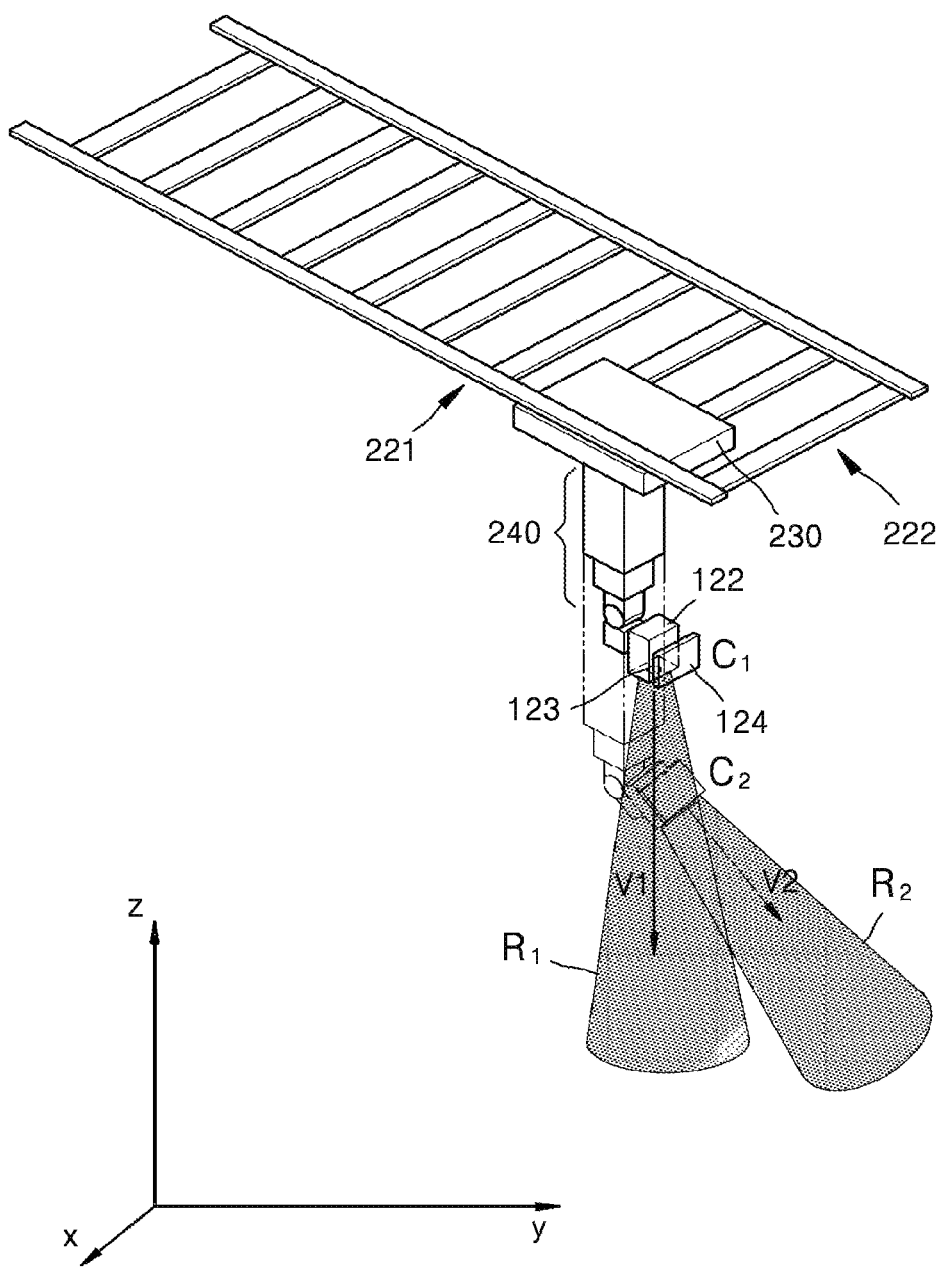
FIG. 15 illustrates an example in which the X-ray apparatus of FIG. 5 acquires directional information of the X-ray radiator included therein.

FIG. 15 illustrates an example in which the X-ray apparatus 500 of FIG. 5 acquires directional information of the X-ray radiator 510 included therein.

The directional information of the X-ray radiator 510 may be information related to an X-ray irradiation region.

As Illustrated in FIG. 15, the directional information of the X-ray radiator 510 may be volume vector groups $R_1$ and $R_2$ corresponding to respective X-ray irradiation regions at the positions $C_1$ and $C_2$.

The volume vector groups $R_1$ and $R_2$ may be formed with 3D shapes on the regions irradiated by X-rays respectively radiated by the X-ray radiator 510 at the positions $C_1$ and $C_2$.

For example, as illustrated in FIG. 15, the volume vector groups $R_1$ and $R_2$ may include the normal vectors $V_1$ and $V_2$ of one surface of the X-ray radiator 510 indicating directional orientation of the X-ray at the positions $C_1$ and $C_2$, respectively.

Figure 16:
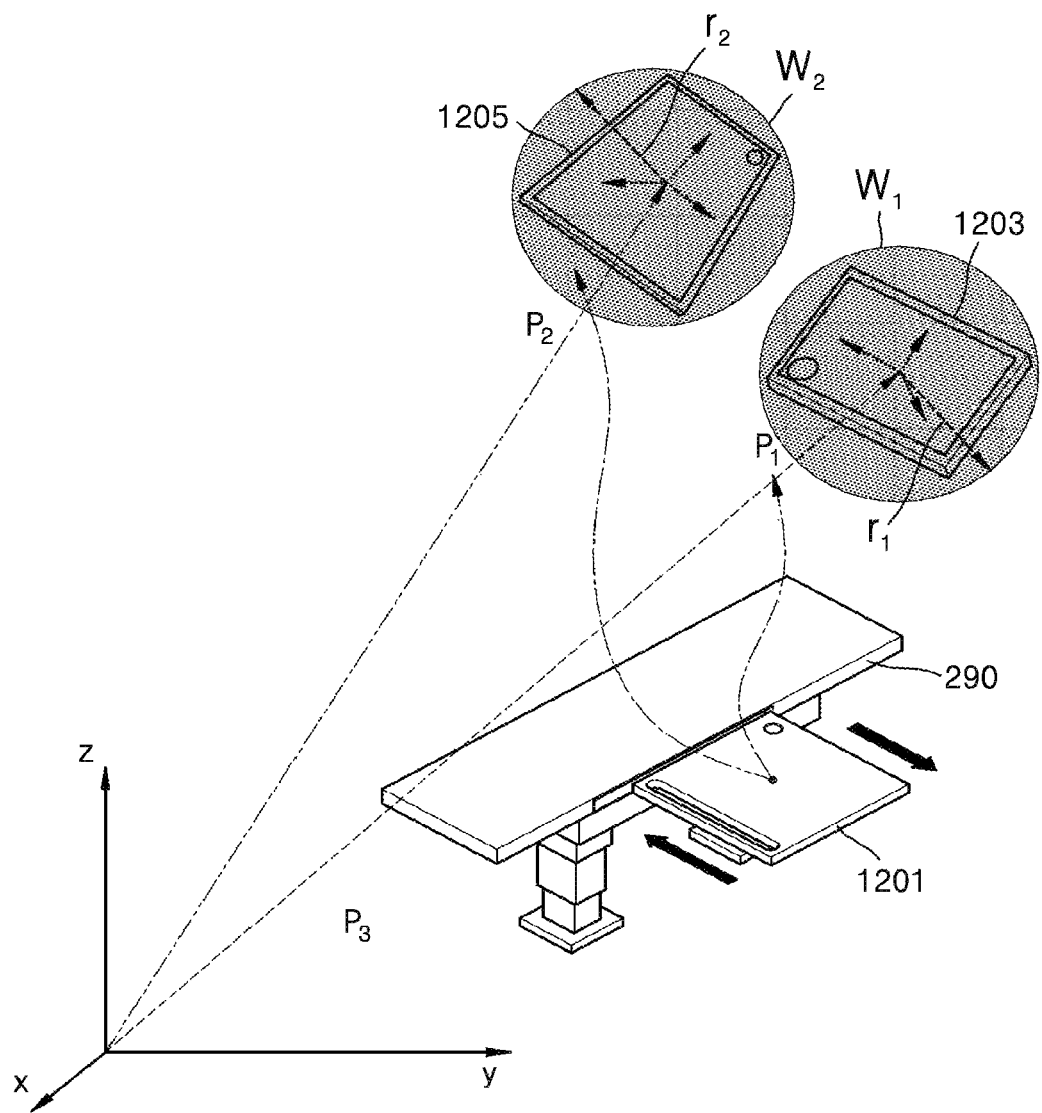
FIG. 16 illustrates an example in which the X-ray apparatus of FIG. 5 acquires position information of an X-ray detector.

FIG. 16 illustrates an example in which the X-ray apparatus 500 of FIG. 5 acquires position information of an X-ray detector.

As illustrated in FIG. 16, a plurality of X-ray detectors 1203 and 1205 may be freely dispersed within a single X-ray imaging space, and the X-ray apparatus 500 acquires respective position information of the X-ray detectors 1203 and 1205. For example, the position information of the X-ray detector includes a position vector of the X-ray detector or a volume vector group including a plurality of position vectors existing within a predetermined distance from the position vector of the X-ray detector.

As illustrated in FIG. 16, respective pieces of position information of the X-ray detectors 1203 and 1205 may be position vectors $P_1$ and $P_2$ of the X-ray detectors 1203 and 1205 in a global coordinate system that is expressed as an inertial frame in which an arbitrary location within an X-ray imaging space is the origin. Also, as illustrated in FIG. 16, the respective pieces of position information of the X-ray detectors 1203 and 1205 may be volume vector groups $W_1$ and $W_2$ including a plurality of position vectors existing within predetermined distances $r_1$ and $r_2$, respectively, from the position vectors $P_1$ and $P_2$ of the respective centers of the X-ray detectors 1203 and 1205.

The volume vector groups $W_1$ and $W_2$ may have predetermined 2D shapes having areas of about 125% to about 150%, in comparison with the respective areas of the X-ray detectors 1203 and 1205, respectively.

In addition, the volume vector groups $W_1$ and $W_2$ may have larger areas than respective regions of the X-ray detectors 1203 and 1205 from which X-rays are actually detected. For example, the predetermined 2D shape may be a circle, an oval, or a polygon (e.g., a square).

In this case, the shapes of the volume vector groups $W_1$ and $W_2$ may be spheres as illustrated in FIG. 16. Although not shown, the shape of each of the volume vector groups $W_1$ and $W_2$ may be a 2D geometric shape, such as a circle, an oval, or a polygon (e.g., a square), or a 3D geometric shape, such as a sphere, an ellipsoid, or a polyhedron.

Figure 17:
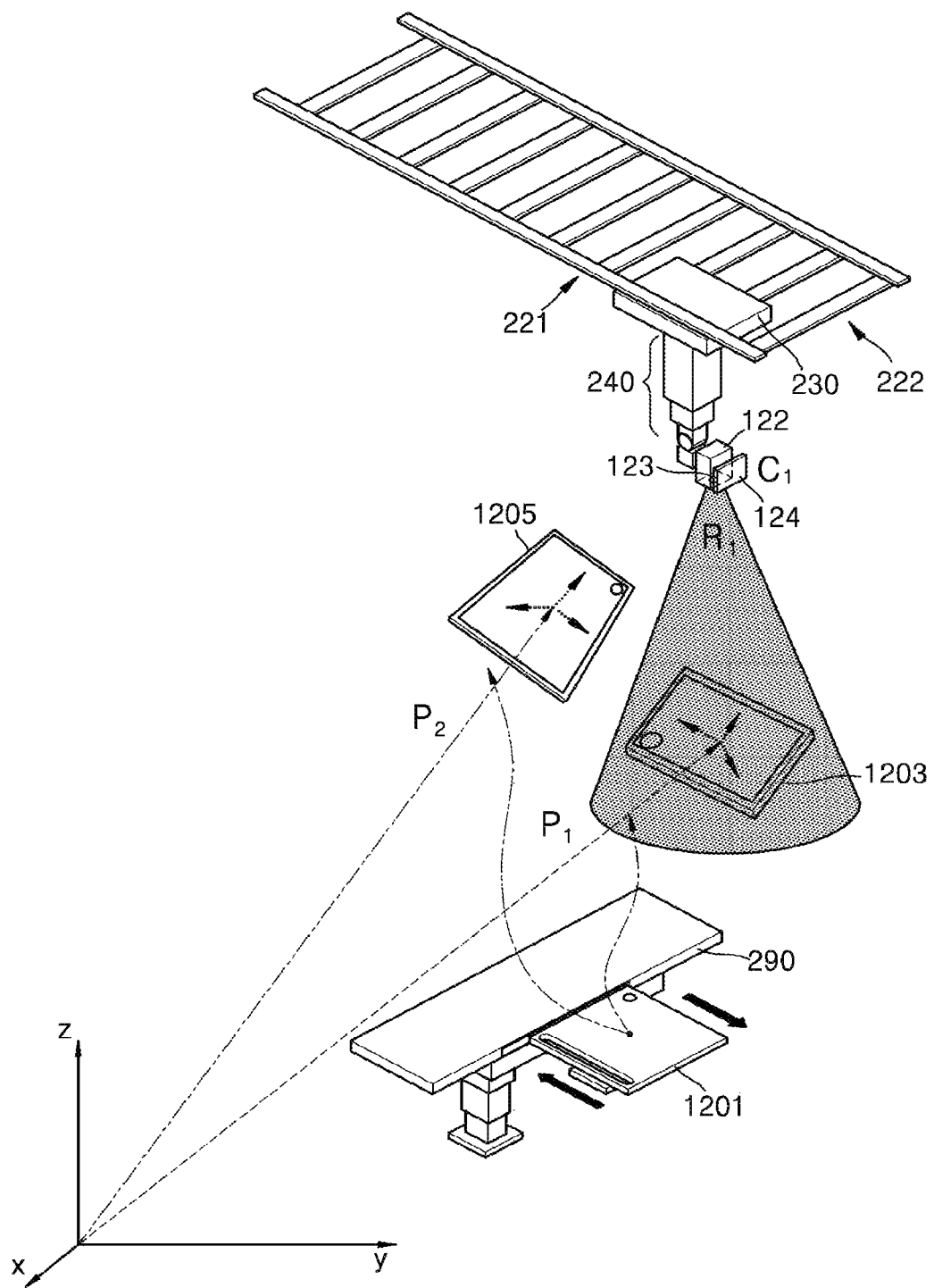
FIGS. 17 and 18 illustrate various examples in which the X-ray apparatus of FIG. 5 selects the X-ray detector based on directional information of the X-ray radiator included therein and position information of the X-ray detector.
Figure 18:
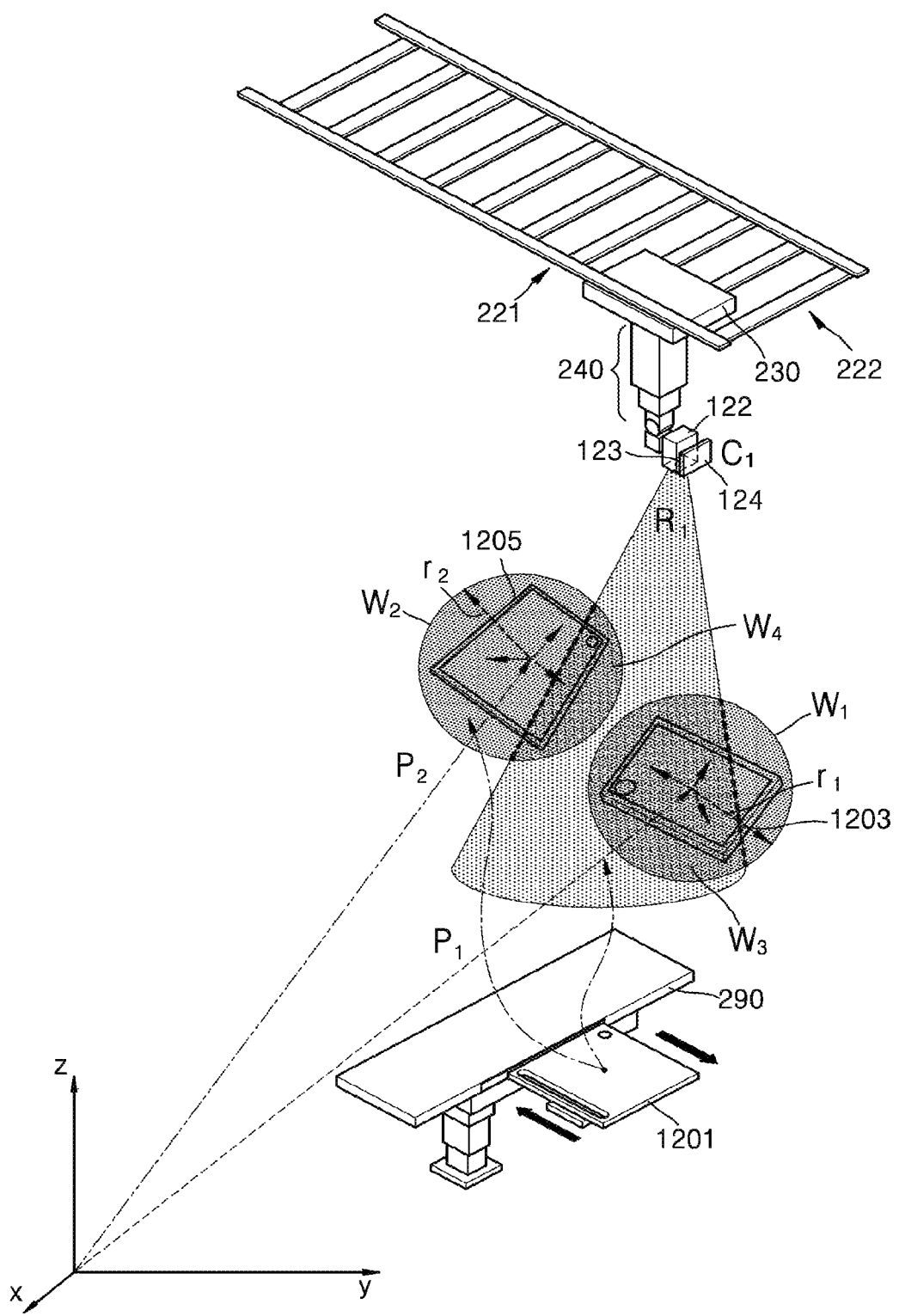

FIGS. 17 and 18 illustrate various examples in which the X-ray apparatus 500 of FIG. 5 selects the X-ray detector based on directional information of the X-ray radiator 510 included therein and position information of the X-ray detector.

The X-ray apparatus 500 may select the X-ray detector when the directional information of the X-ray radiator 510 corresponding to X-ray irradiation regions is adjacent to the position information of the X-ray detector. In this case, the main controller 520 of the X-ray apparatus 500 may determine a relationship between the directional information of the X-ray radiator 510 and the position information of the X-ray detector.

As illustrated in FIG. 17, when the X-ray radiator 510 is located at the position $C_1$ within the X-ray imaging space, the directional information of the X-ray radiator 510 may be the volume vector group $R_1$ corresponding to the X-ray irradiation region. The position information of the X-ray detectors 1203 and 1205 may be the position vector $P_1$ of the X-ray detector 1203 and the position vector $P_2$ of the X-ray detector 1205, respectively.

In this case, the X-ray apparatus 500 may select the X-ray detector based on the volume vector group of the X-ray radiator 510 and the position vectors of the X-ray detectors 1203 and 1205. In this case, the X-ray apparatus 500 may activate the X-ray detector based on the volume vector group of the X-ray radiator 510 and the position vectors of the X-ray detectors 1203 and 1205. The X-ray apparatus 500 may generate the signal for activating the X-ray detector based on the volume vector group of the X-ray radiator 510 and the position vectors of the X-ray detectors 1203 and 1205. For example, when the position vector of the X-ray detector is included in the volume vector group of the X-ray radiator 510, the X-ray detector corresponding to the position vector may be selected. When the position vector of the X-ray detector is included in the volume vector group of the X-ray radiator 510, the X-ray detector corresponding to the position vector may be activated. The signal for activating the X-ray detector corresponding to the position vector may be generated.

As illustrated in FIG. 17, since the second position vector $P_1$ is included in the volume vector group $R_1$, the X-ray detector 1203 corresponding to the second position vector $P_1$ may be selected. Alternatively, a signal for activating the X-ray detector 1203 may be generated.

On the other hand, since the second position vector $P_2$ is not included in the volume vector group $R_1$, the X-ray detector 1205 may not be selected.

As illustrated in FIG. 18, when the X-ray radiator 510 is located at the position $C_1$ within the X-ray imaging space, the directional information of the X-ray radiator 510 may be the volume vector group $R_1$ corresponding to the X-ray irradiation region. And the position information of the X-ray detectors 1203 and 1205 may be the volume vector groups $W_1$ and $W_2$ including a plurality of position vectors existing within the predetermined distances $r_1$ and $r_2$ from the position vectors $P_1$ and $P_2$ of the respective centers of the X-ray detectors 1203 and 1205, respectively.

In this case, the X-ray apparatus 500 may select the X-ray detector based on the first volume vector group of the X-ray radiator 510 corresponding to the directional information of the X-ray radiator 510 and the second volume vector groups of the X-ray detectors 1203 and 1205 corresponding to the position information of the X-ray detectors 1203 and 1205. In this case, the X-ray apparatus 500 may activate the X-ray detector based on the first volume vector group of the X-ray radiator 510 and the second volume vector groups of the X-ray detectors 1203 and 1205.

For example, when a ratio of the number of position vectors in the second volume vector group with respect to the number of a plurality of position vectors included in the first volume vector group is equal to or greater than a predetermined value ($0<k<1$, real number, i.e., $k=0.7$), the X-ray detector corresponding to the second volume vector group may be selected.

As illustrated in FIG. 18, since the size of the group $W_3$ of a plurality of position vectors existing within both the first volume vector group $R_1$ and the second volume vector group $W_1$ is at least 0.7 of the size of the second volume vector group $W_1$, the X-ray detector 1203 corresponding to the second volume vector group $W_1$ may be selected. Since the size of the group $W_3$ of a plurality of position vectors existing within both the first volume vector group $R_1$ and the second volume vector group $W_1$ is at least 0.7 of the size of the second volume vector group $W_1$, the signal for activating the X-ray detector 1203 may be generated.

On the other hand, since the size of a group $W_4$ of a plurality of position vectors existing within both the first volume vector group $R_1$ and the second volume vector group $W_2$ is less than 0.7 of the size of the second volume vector group $W_2$, the X-ray detector 1205 corresponding to the second volume vector group $W_2$ may not be selected.

Figure 19:
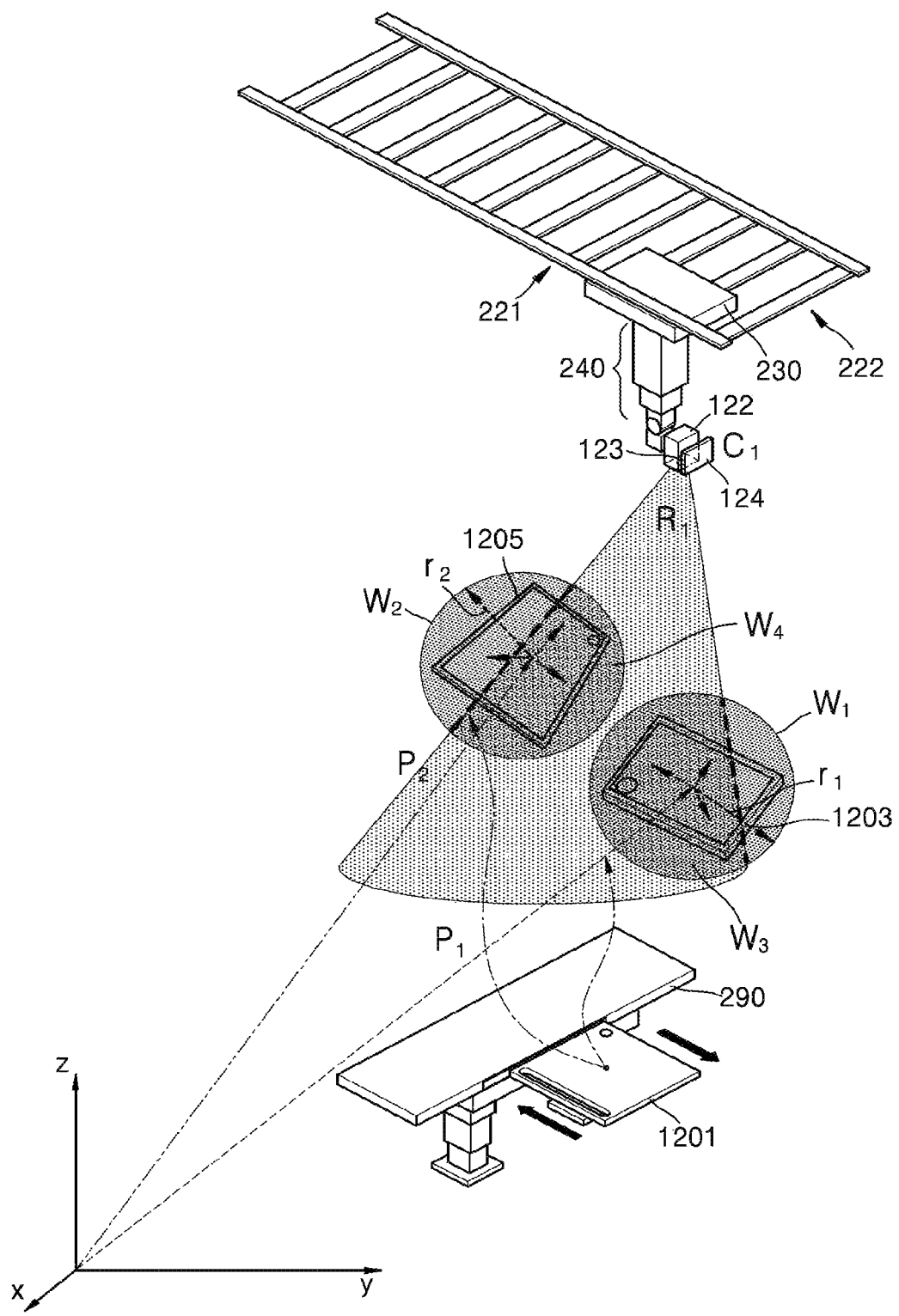
FIG. 19 illustrates an example in which the X-ray apparatus of FIG. 5 selects a plurality of X-ray detectors based on orientation information of the X-ray radiator included therein and orientation information of the X-ray detector.

FIG. 19 illustrates an example in which the X-ray apparatus 500 of FIG. 5 selects a plurality of X-ray detectors based on orientation information of the X-ray radiator 510 included therein and orientation information of the X-ray detector.

For example, the orientation information of the X-ray radiator 510 may include at least one selected from position information of the X-ray radiator 510 and directional information thereof, and the orientation information of the X-ray detector may include at least one selected from position information of the X-ray detector and directional information thereof.

For example, as illustrated in FIG. 18, the X-ray apparatus 500 may select the X-ray detector based on the directional information of the X-ray radiator 510 and the position information of the X-ray detector.

As illustrated in FIG. 19, the X-ray apparatus 500 may select the X-ray detector based on the first volume vector group $R_1$ of the X-ray radiator 510 corresponding to the directional information of the X-ray radiator 510 and the second volume vector groups $W_1$ and $W_2$ of the X-ray detectors 1203 and 1205 corresponding to the position information of the X-ray detectors.

For example, when a ratio of the number of position vectors in the second volume vector group with respect to the number of a plurality of position vectors included in the first volume vector group is equal to or greater than a predetermined value (0<k<1, real number, i.e., k=0.7), the X-ray detector corresponding to the second volume vector group may be selected.

As illustrated in FIG. 19, since the size of the group $W_3$ of a plurality of position vectors existing within both the first volume vector group $R_1$ and the second volume vector group $W_1$ is at least 0.7 of the size of the second volume vector group $W_1$, the X-ray detector 1203 corresponding to the second volume vector group $W_1$ may be selected. Since the size of the group $W_3$ of a plurality of position vectors existing within both the first volume vector group $R_1$ and the second volume vector group $W_1$ is at least 0.7 of the size of the second volume vector group $W_1$, the X-ray detector 1203 corresponding to the second volume vector group $W_1$ may be activated. Also, as illustrated in FIG. 19, since the size of a group $W_4$ of a plurality of position vectors existing within both the first volume vector group $R_1$ and the second volume vector group $W_2$ is at least 0.7 of the size of the second volume vector group $W_2$, the X-ray detector 1205 corresponding to the second volume vector group $W_2$ may be selected. Since the size of the group $W_4$ of a plurality of position vectors existing within both the first volume vector group $R_1$ and the second volume vector group $W_2$ is also at least 0.7 of the size of the second volume vector group $W_2$, the X-ray detector 1205 corresponding to the second volume vector group $W_2$ may be activated.

In this case, at least one X-ray detector to be used in imaging may be selected based on a user input from among a plurality of X-ray detectors, namely, the X-ray detectors 1203 and 1205, selected by the main controller 520 of the X-ray apparatus 500

Figure 20:
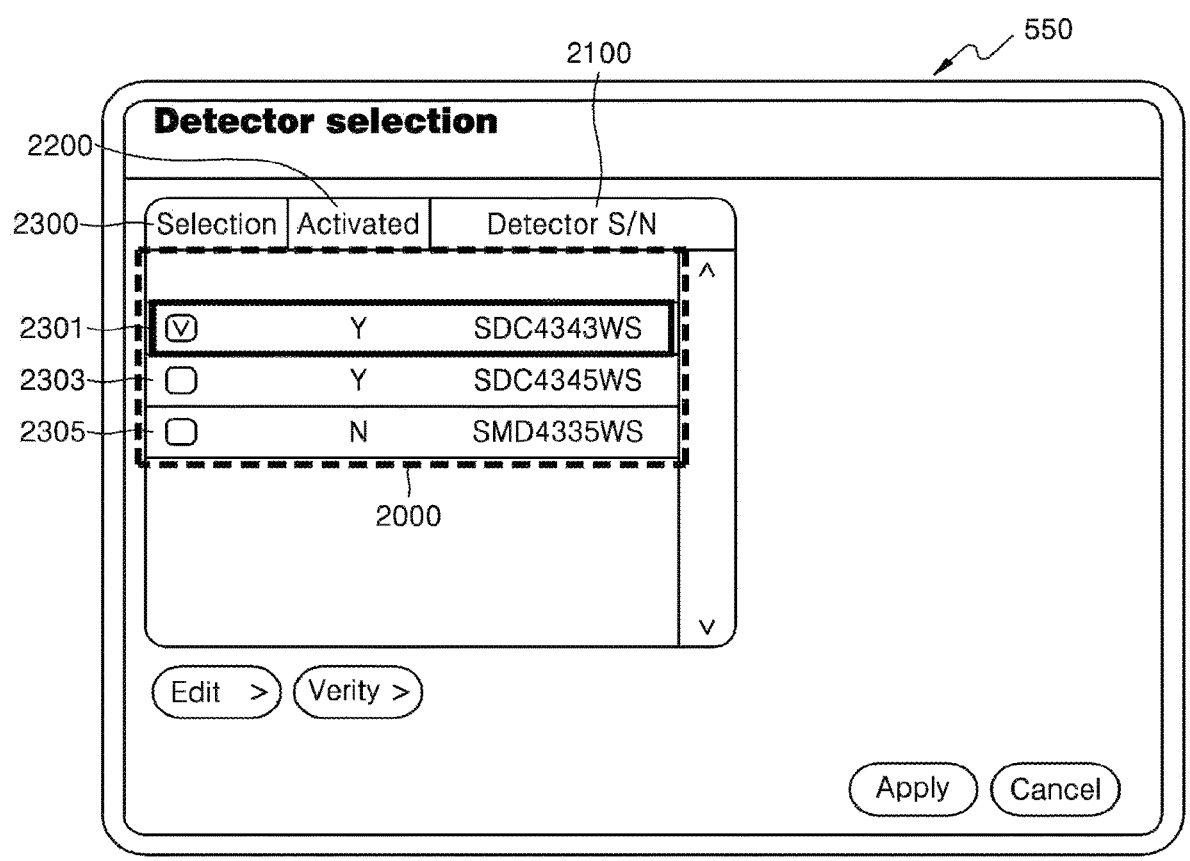
FIG. 20 illustrates an example in which the X-ray apparatus of FIG. 5 displays information about a plurality of X-ray detectors selectable by a user on an output unit included in the X-ray apparatus.

FIG. 20 illustrates an example in which the X-ray apparatus 500 displays information about a plurality of X-ray detectors selectable by a user on the output unit 550.

For example, as illustrated in FIG. 20, a UI 2000 for receiving a user's selection of at least one X-ray detector from among a plurality of X-ray detectors may be output.

The UI 2000 may include respective pieces of information about a plurality of X-ray detectors 2301, 2303, and 2305. The respective pieces of information about the X-ray detectors 2301, 2303, and 2305 may be arranged according to a predetermined arrangement criterion and then output.

For example, the information about each of the X-ray detectors 2301, 2303, and 2305 may include unique information 2100 of each of the X-ray detectors 2301, 2303, and 2305. In detail, the unique information 2100 may include at least one selected from a serial number (SN) of each of the X-ray detectors 2301, 2303, and 2305 and an Internet Protocol (IP) address thereof. In detail, the SN of each of the X-ray detectors 2301, 2303, and 2305 is a unique identifier given during the manufacture of each of the X-ray detectors 2301, 2303, and 2305. The IP address of each of the X-ray detectors 2301, 2303, and 2305 may include an IP address value that is to be used when each of the X-ray detectors 2301, 2303, and 2305 and an access point (AP) communicate with each other.

The information about each of the X-ray detectors 2301, 2303, and 2305 may include specification information of each of the X-ray detectors 2301, 2303, and 2305. In detail, the specification information may include at least one selected from the size of each of the X-ray detectors 2301, 2303, and 2305 and the type of a receptor with which each of the X-ray detectors 2301, 2303, and 2305 is combinable. Other types of specification information may also be used, such as information related to physical dimensions of the detectors, software of the detectors, weight of the detectors, etc. An X-ray detector adequate for X-ray imaging may have different sizes and shapes according to parts of an object to be imaged. Accordingly, the sizes of the X-ray detectors 2301, 2303, and 2305 may be a criterion on which a user selects an X-ray detector suitable for imaging. In addition, when a user wants to combine the X-ray detectors 2301, 2303, and 2305 to a predetermined receptor, the type of a receptor with which the X-ray detectors 2301, 2303, and 2305 are combinable may be a criterion on which a user selects an X-ray detector suitable for imaging.

The specification information of each of the X-ray detectors 2301, 2303, and 2305 is not limited to the sizes of the X-ray detectors 2301, 2303, and 2305 and the type of a receptor with which the X-ray detectors 2301, 2303, and 2305 are combinable.

For example, the predetermined arrangement criterion may be a distance proximity to the X-ray radiator 510, the sizes of the X-ray detectors 2301, 2303, and 2305, or the like. For example, an X-ray detector which is relatively closer to the X-ray radiator 510 than an X-ray detector disposed on the table type receptor 290 may have a higher priority than that of the X-ray detector disposed on the table type receptor 290 when pieces of information about a plurality of X-ray detectors are output to the output unit 550. In addition, an X-ray detector having a relatively large size may have a higher priority than an X-ray detector having a relatively small size. For example, an X-ray detector having a size of 17 inch×17 inch may have a higher priority than an X-ray detector having a size of 14 inch×17 inch when pieces of information about a plurality of X-ray detectors are output to the output unit 550.

The information about each of the X-ray detectors 2301, 2303, and 2305 may further include information 2200 indicating whether each of the X-ray detectors 2301, 2303, and 2305 has been activated.

In this case, an X-ray detector that is automatically activated based on the orientation information of the X-ray radiator 510 and the orientation information of the X-ray detector may have a high priority, e.g., a relatively higher priority as compared to other X-ray detectors, when pieces of information about a plurality of X-ray detectors are output to the output unit 550.

For example, as illustrated in FIG. 20, the X-ray detectors 2301 and 2303 which are automatically activated may be output in preference to the X-ray detector 2305 which has not been activated.

The UI 2000 may further include an icon 2300 for selecting an X-ray detector that is desired to be activated according to a user input.

As illustrated in FIG. 20, when a user selects the X-ray detector 2301 corresponding to an SN of SDC4343WS, the X-ray detector 2301 may be determined as the at least one X-ray detector that is to be used in imaging.

In this case, the X-ray detector 2303, which is not selected by the user's input to be used in X-ray imaging of an object, may be deactivated.

Alternatively, before a plurality of X-ray detectors 2301 and 2303 positioned in certain directions from the X-ray radiator 510 are automatically activated, only the X-ray detector 2301 selected by a user may be activated to be subsequently used in the X-ray imaging of an object.

Figure 21:
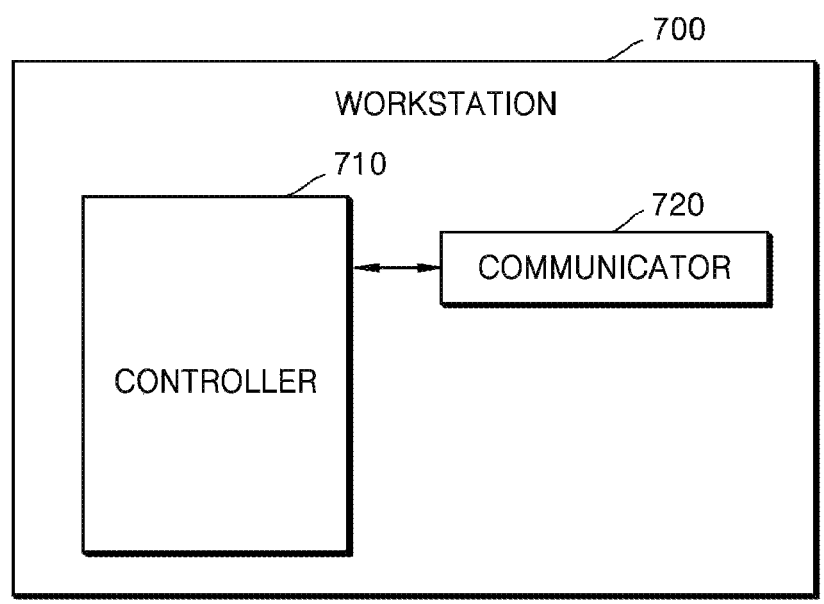
FIG. 21 is a block diagram of a workstation according to an exemplary embodiment.

FIG. 21 is a block diagram of a workstation 700 according to an exemplary embodiment.

The workstation 700 may include a controller 710 and a communicator 720. The workstation 700 may further include a receiver, an output unit, and an input unit.

When the workstation 700 of FIG. 21 is included in the X-ray system 1000 of FIG. 1, the workstation 700 of FIG. 21 may correspond to the workstation 110 of FIG. 1. In detail, the controller 710, the output unit, and the input unit of the workstation 700 of FIG. 21 may respectively correspond to the controller 113, the output unit 111, and the input unit 112 of the workstation 110 of FIG. 1. The communicator 720 of the workstation 700 of FIG. 21 may communicate with the X-ray apparatus 100 of FIG. 1 by wires or wirelessly and may also communicate with an external apparatus via the network 150 of FIG. 1. Thus, a repeated description thereof will be omitted.

The aforementioned components will now be described in detail.

The controller 710 may acquire orientation information of an X-ray radiator and orientation information of an X-ray detector.

For example, the orientation information of the X-ray radiator may include at least one selected from position information of the X-ray radiator and directional information thereof, and the orientation information of the X-ray detector may include at least one selected from position information of the X-ray detector and directional information thereof.

In this case, the orientation information of the X-ray radiator or the orientation information of the X-ray detector may be directly acquired by the controller 710 of the workstation 700 by using any of various sensors or apparatuses.

For example, the orientation information of the X-ray radiator or the orientation information of the X-ray detector may be acquired in real time by a camera or may be acquired using a wireless frequency.

In this case, since orientation information of an object within an X-ray imaging space may be acquired using any of various sensors or apparatuses according to various methods, such as common methods of using light, electromagnetic waves, sound waves, a magnetic field, and an electric field, a method of acquiring the orientation information of the X-ray radiator or the orientation information of the X-ray detector is not limited to a specific method.

Based on the orientation information of the X-ray radiator and the orientation information of the X-ray detector, the controller 710 may select the X-ray detector that is used in X-ray imaging.

In this case, the controller 710 may generate at least one selected from a signal for informing selection of the X-ray detector and a signal for activating the X-ray detector.

The communicator 720 may transmit the signal for informing selection of the X-ray detector or the signal for activating the X-ray detector to the X-ray detector selected to be used for imaging.

In this case, the X-ray detector may be activated based on the signal received from the workstation via a network.

The controller 710 may control orientation of the X-ray radiator, based on the orientation information of the selected X-ray detector.

An X-ray system according to an exemplary embodiment includes an X-ray detector, an X-ray apparatus including an X-ray radiator, and a workstation that controls the X-ray apparatus and the X-ray detector. The workstation includes a controller and a communicator. The controller acquires orientation information of the X-ray radiator and orientation information of the X-ray detector, and controls the workstation to select the X-ray detector or generate a signal for activating the selected X-ray detector based on the orientation information of the X-ray radiator and the orientation information of the X-ray detector. The communicator transmits the signal to the X-ray detector. The X-ray detector includes a communicator and a detector controller. The communicator of the X-ray detector receives the signal from the workstation, and the detector controller controls the X-ray detector to be activated based on the signal.

In the X-ray system, the controller of the workstation may also control the orientation of the X-ray radiator, based on the orientation information of the X-ray detector.

Figure 22:
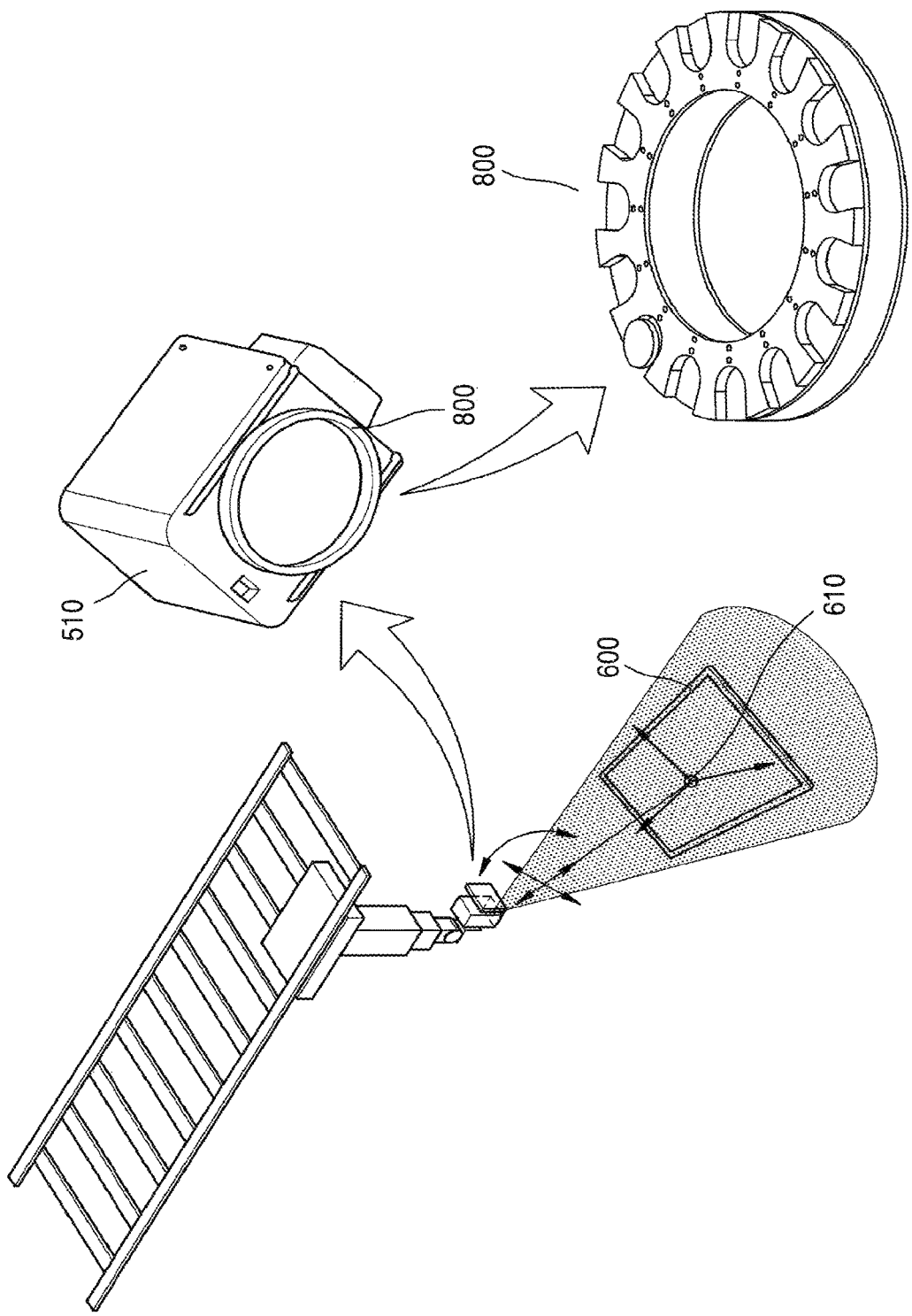
FIG. 22 illustrates an example in which the X-ray apparatus of FIG. 5 controls an orientation of the X-ray radiator included therein based on orientation information of the X-ray detector of FIG. 6.

FIG. 22 illustrates an example in which the X-ray apparatus 500 of FIG. 5 controls an orientation of the X-ray radiator 510 included therein based on orientation information of the X-ray detector 600 of FIG. 6.

As illustrated in FIG. 22, the X-ray radiator 510 may include a magnetic field source 800, and the magnetic field source 800 may be coupled to a lower end of a collimator and radiate a magnetic field.

The magnetic field source 800 may include a ring-shaped coil and a plurality of magnets. In this case, the magnetic field source 800 may emit a magnetic field including both a magnetic field generated by the magnets and a magnetic field generated by the ring-shaped coil.

The sensor unit 610 of the X-ray detector 600 may be a magnetometer. The magnetometer 610 may include three axes and sense the intensity of a magnetic field. For example, the magnetometer 610 of the X-ray detector 600 may sense the intensity of a magnetic field emitted by the magnetic field source 800 coupled to the X-ray radiator 510. At this time, the detector controller 620 of the X-ray detector 600 may acquire magnetic field information including information about the direction and size of the magnetic field sensed by the magnetometer 610.

In addition, the detector controller 620 of the X-ray detector 600 may determine a relationship between orientations of the X-ray radiator 510 and the X-ray detector 600, based on the acquired magnetic field information.

For example, when a magnetic field change rate of a tangential vector of the magnetic field information is 0, the detector controller 620 of the X-ray detector 600 may determine that the X-ray radiator 510 and the X-ray detector 600 face each other.

At this time, information about the relationship between the orientations of the X-ray radiator 510 and the X-ray detector 600 determined by the X-ray detector 600 may be transmitted to the X-ray apparatus 500.

Accordingly, a user may ascertain the relationship between the orientations of the X-ray radiator 510 and the X-ray detector 600. In this case, the user may adjust the orientation of the X-ray radiator 510 that is at least one selected from a position, a direction and an angle of the X-ray radiator 510, such that the X-ray radiator 510 and the X-ray detector 600 face each other.

Alternatively, the main controller 520 of the X-ray apparatus 500 may automatically adjust the orientation of the X-ray radiator 510 based on the orientation of the X-ray radiator 510 and the orientation of the X-ray detector 600, such that the X-ray radiator 510 and the X-ray detector 600 face each other. The main controller 520 of the X-ray apparatus 500 according to an exemplary embodiment may acquire orientation information of the X-ray radiator 510 and orientation information of the X-ray detector 600, and determine whether the X-ray radiator 510 and the X-ray detector 600 face each other, based on the orientation information of the X-ray radiator 510 and the orientation information of the X-ray detector 600.

In this case, if the X-ray radiator 510 and the X-ray detector 600 do not face each other, the main controller 520 of the X-ray apparatus 500 may control orientation of the X-ray radiator 510 or orientation of the X-ray detector 600 so that the X-ray radiator 510 and the X-ray detector 600 may face each other.

For example, the orientation information of the X-ray detector 600 includes at least one selected from position information of the X-ray detector 600 and directional information of the X-ray detector 600, and the orientation information of the X-ray radiator 510 includes at least one selected from position information of the X-ray radiator 510 and directional information of the X-ray radiator 510. The directional information of the X-ray radiator 510 may include at least one selected from an X-ray radiation direction and an X-ray radiation angle.

The main controller 520 of the X-ray apparatus 500 may control the position of the X-ray radiator 510 based on the position information of the X-ray detector 600.

For example, after the position of the X-ray detector 600 is determined, the X-ray radiator 510 may move to a position corresponding to the position of the X-ray detector 600 in order to perform X-ray imaging. For example, the X-ray radiator 510 may move to a position where a distance between the X-ray detector 600 and the X-ray radiator 510 is 100 cm or 180 cm.

The main controller 520 of the X-ray apparatus 500 may control the direction of the X-ray radiator 510 based on the directional information of the X-ray detector 600.

For example, after the direction of the X-ray detector 600, namely, a direction in which the X-ray detector 600 receives an X-ray, is determined, the main controller 520 of the X-ray apparatus 500 may control the direction of the X-ray radiator 510, namely, the X-ray radiation direction or the X-ray radiation angle, to be aligned with the direction of the X-ray detector 600.

The main controller 520 of the X-ray apparatus 500 may control the direction of the X-ray radiator 510 based on the position information of the X-ray detector 600.

The main controller 520 of the X-ray apparatus 500 may control the position of the X-ray radiator 510 based on the directional information of the X-ray detector 600.

The main controller 520 of the X-ray apparatus 500 may simultaneously or sequentially control the position and direction of the X-ray radiator 510, based on the position information and directional information of the X-ray detector 600.

Figure 23:
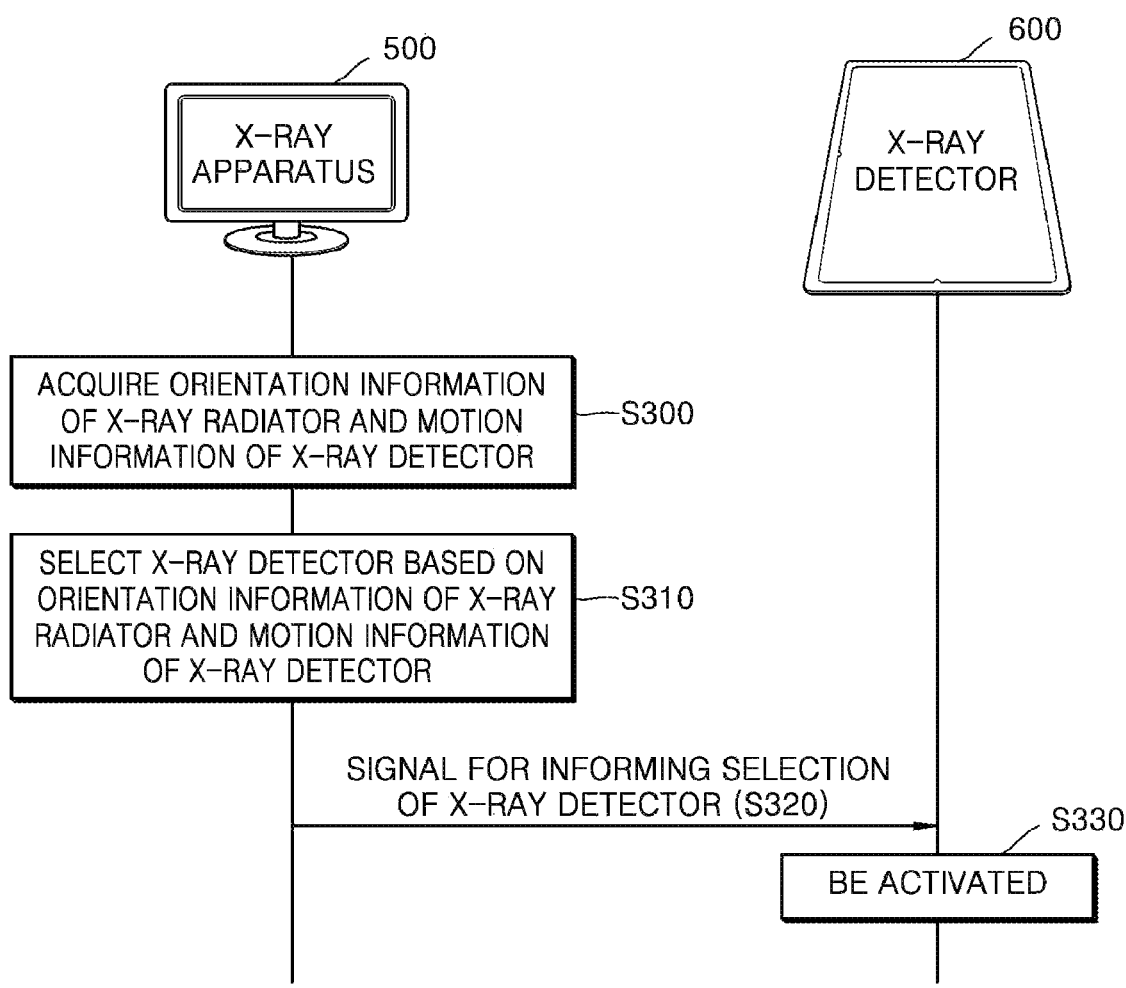
FIG. 23 is a flowchart of an operation of activating an X-ray detector selected by an X-ray apparatus according to an exemplary embodiment.

FIG. 23 is a flowchart of an operation of activating an X-ray detector selected by an X-ray apparatus, according to an exemplary embodiment.

In operation S300, the X-ray apparatus 500 acquires orientation information of the X-ray radiator 510 and motion information of the X-ray detector 600 by using any of various sensors or apparatuses.

For example, the orientation information of the X-ray radiator 510 or the motion information of the X-ray detector 600 may be directly acquired by the main controller 520 of the X-ray apparatus 500 by using any of various sensors or apparatuses.

The motion information of the X-ray detector 600 may be acquired in connection with a movement sensed by the sensor unit 610 of the X-ray detector 600 directly by the detector controller 620 of the X-ray detector 600, and may be received by the X-ray apparatus 500 via the communicator 530.

For example, the orientation information of the X-ray radiator 510 may include at least one selected from the position information of the X-ray radiator 510 and the direction information thereof, and the motion information of the X-ray detector 600 may include at least one selected from motion time information of the X-ray detector 600 and motion direction information thereof.

In operation S310, the X-ray apparatus 500 selects the X-ray detector 600 based on the orientation information of the X-ray radiator 510 and the motion information of the X-ray detector 600 acquired in operation S300.

For example, the X-ray detector 600 may be selected based on the orientation information of the X-ray radiator 510 and the motion time information corresponding to the time section during which the X-ray detector 600 moves.

Specifically, an X-ray detector that has moved last from among a plurality of X-ray detectors that have a predetermined relationship with the orientation of the X-ray radiator 510 may be selected.

The X-ray detector 600 may also be selected based on the orientation information of the X-ray radiator 510 and the motion directional information corresponding to a direction in which the X-ray detector moves.

Specifically, if it is determined that at least one selected from a starting point and an ending point of a movement trajectory corresponding to a movement of the X-ray detector 600 is adjacent to a location of the X-ray radiator 510, the X-ray detector 600 may be selected as an X-ray detector that is used in X-ray imaging.

The determination that at least one selected from a starting point and an ending point of a movement trajectory corresponding to a movement of the X-ray detector 600 is adjacent to a location of the X-ray radiator 510 may correspond to the determination that the X-ray radiator 510 and the X-ray detector 600 are adjacent to each other as described above with reference to FIG. 11.

Also, if it is determined that the movement trajectory of the X-ray detector 600 is included in an X-ray irradiation region irradiated by the X-ray radiator 510, the X-ray detector 600 may be selected as the X-ray detector that is used in X-ray imaging.

The determination that the movement trajectory corresponding to a movement of the X-ray detector 600 is included in the X-ray irradiation region irradiated by the X-ray radiator 510 may correspond to the determination that the location of the X-ray detector 600 is included in the X-ray irradiation region irradiated by the X-ray radiator 510 as described above with reference to FIGS. 17-19.

In operation S320, the X-ray apparatus 500 transmits, to the X-ray detector 600 selected in operation S310, a signal for indicating that the X-ray detector 600 has been selected.

In operation S320, the X-ray apparatus 500 also transmits, to the X-ray detector 600 selected in operation S310, a signal for activating the X-ray detector 600.

In operation S330, the X-ray detector 600 is activated based on the signals received from the X-ray apparatus 500 in operation S320.

Figure 24:
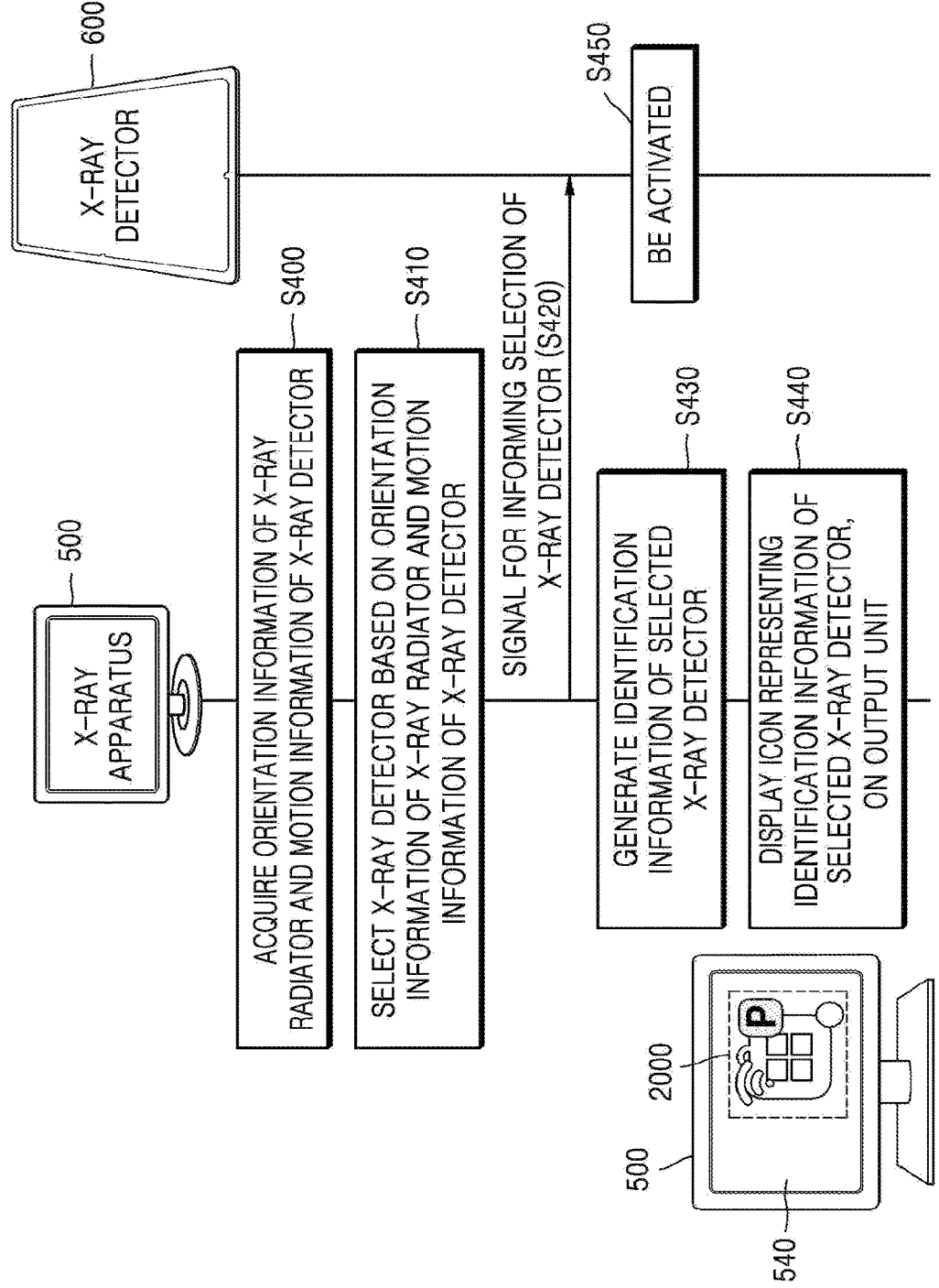
FIG. 24 is a flowchart of displaying identification information of an X-ray detector selected by an X-ray apparatus according to an exemplary embodiment.

FIG. 24 is a flowchart of displaying identification information of an X-ray detector selected by an X-ray apparatus, according to an exemplary embodiment.

Operations S400, S410, S420 and S450 of FIG. 24 correspond to operations S300, S310, S320 and S330 of FIG. 23, and thus detailed descriptions thereof will be omitted here.

In operation S430, the X-ray apparatus 500 generates identification information of the X-ray detector 600 selected in operation S410.

For example, the identification information of the X-ray detector 600 selected based on the orientation information of the X-ray radiator 510 and the motion information of the X-ray detector 600 may be generated.

In this case, the identification information of the selected X-ray detector 600 may be generated based on the motion information of the selected X-ray detector 600, for example, based on motion direction information corresponding to a movement direction of the selected X-ray detector 600.

For example, the identification information of the X-ray detector 600 may include mounting position information of the X-ray detector 600. In this case, the mounting position information of the X-ray detector 600 may include at least one selected from information indicating that the X-ray detector 600 has been combined with a stand type receptor, information indicating that the X-ray detector 600 has been combined with a table type receptor, and information indicating that the X-ray detector 600 is combined with no receptors.

For example, when the movement direction of the X-ray detector 600 is a vertical direction of a certain trajectory, the identification information of the X-ray detector 600 may include the information indicating that the X-ray detector 600 has been combined with a stand type receptor.

On the other hand, when the movement direction of the X-ray detector 600 is a horizontal direction of a certain trajectory, the identification information of the X-ray detector 600 may include the information indicating that the X-ray detector 600 has been combined with a table type receptor.

On the other hand, when the movement direction of the X-ray detector 600 is neither a vertical direction nor a horizontal direction of a certain trajectory, the identification information of the X-ray detector 600 may include the information indicating that the X-ray detector 600 is combined with no receptors.

In operation S440, the X-ray apparatus 500 displays an icon representing the identification information generated in operation S430, on the output unit 540.

Accordingly, the X-ray apparatus 500 generates the identification information of the X-ray detector selected based on the orientation information of the X-ray radiator 510 and the motion information of the X-ray detector 600, and displays an icon 2000 representing the identification information on the output unit 540. Accordingly, a user easily recognizes the X-ray detector 600, which is to be used for imaging, even without spending much time and effort.

Figure 25:
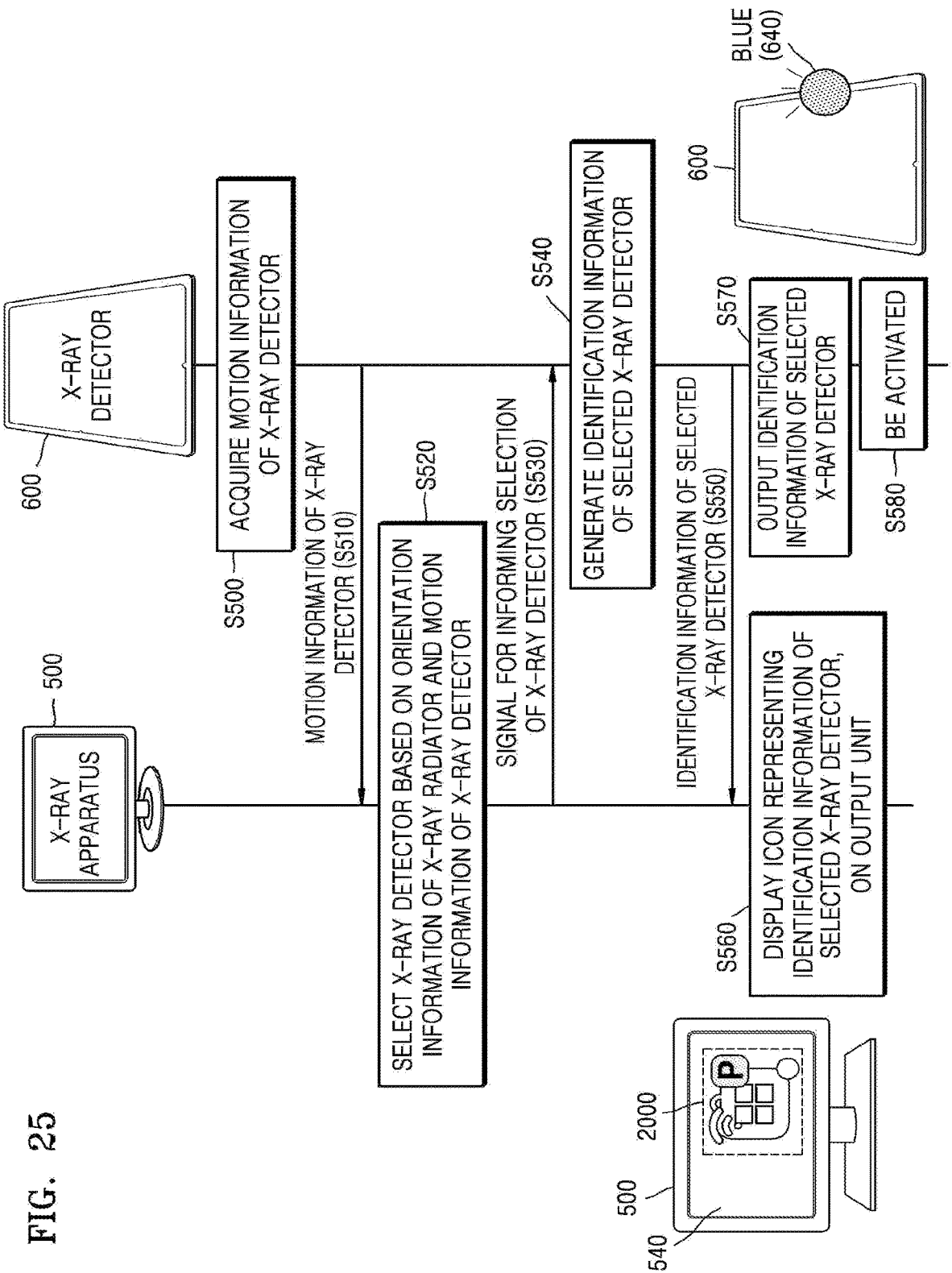
FIG. 25 is a flowchart of a method in which an X-ray detector selected by an X-ray apparatus according to an exemplary embodiment displays identification information of the selected X-ray detector.

FIG. 25 is a flowchart of a method in which an X-ray detector selected by an X-ray apparatus displays identification information of the selected X-ray detector, according to an exemplary embodiment.

In operation S500, the X-ray detector 600 senses (acquires) a movement of the X-ray detector 600 via the sensor unit 610, and the detector controller 620 acquires motion information related to the movement of the X-ray detector 600, based on the movement of the X-ray detector 600 sensed by the sensor unit 610. The sensor unit 610 may sense the movement of the X-ray detector 600, and a sensor controller included in the sensor unit 610 may acquire the motion information related to the movement of the X-ray detector 600.

For example, the motion information of the X-ray detector 600 may include at least one selected from motion time information corresponding to a time section during which the X-ray detector 600 moves, and motion direction information corresponding to a movement direction of the X-ray detector 600.

In operation S510, the X-ray apparatus 500 receives the motion information of the X-ray detector 600 from the X-ray detector 600.

In operation S520, the X-ray apparatus 500 selects the X-ray detector 600 based on the motion information of the X-ray detector 600 acquired in operation S500 and orientation information of the X-ray radiator 510.

In operation S530, the X-ray apparatus 500 transmits, to the X-ray detector 600 selected in operation S520, a signal for informing that the X-ray detector 600 has been selected.

In operation S540, the X-ray detector 600 generates identification information of the X-ray detector 600, based on the signal received in operation S530.

For example, the identification information of the X-ray detector 600 may include mounting position information of the X-ray detector 600. In this case, the mounting position information of the X-ray detector 600 may include at least one selected from information indicating that the X-ray detector 600 has been combined with a stand type receptor, information indicating that the X-ray detector 600 has been combined with a table type receptor, and information indicating that the X-ray detector 600 is combined with no receptors.

In this case, the mounting motion information of the X-ray detector 600 may be generated based on the motion information related to the movement sensed by the sensor unit 610 of the X-ray detector 600.

In operation S550, the X-ray apparatus 500 receives the identification information of the X-ray detector 600 from the X-ray detector 600.

In operation S560, the X-ray apparatus 500 displays an icon 2000 representing the identification information received in operation S550, on the output unit 540.

In operation S570, the X-ray detector 600 may control the identification information generated in operation S540 to be output to the output unit 640.

For example, the identification information of the X-ray detector 600 may include the mounting position information of the X-ray detector 600. In this case, the mounting position information of the X-ray detector 600 may include at least one selected from information indicating that the X-ray detector 600 has been combined with a stand type receptor, information indicating that the X-ray detector 600 has been combined with a table type receptor, and information indicating that the X-ray detector 600 is combined with no receptors.

In this case, the output unit 640 (e.g., an LED or a speaker) of the X-ray detector 600 may output different indicators according to the mounting position information of the X-ray detector 600.

For example, the output unit 640 of the X-ray detector 600 may emit a yellow light in order to output the information indicating that the X-ray detector 600 has been combined with a stand type receptor. It is understood that light other than a yellow light may be emitted to output the information.

The output unit 640 of the X-ray detector 600 may emit a red light in order to output the information indicating that the X-ray detector 600 has been combined with a table type receptor. It is understood that a light other than a red light may be emitted to output the information.

The output unit 640 of the X-ray detector 600 may emit a blue light in order to output the information indicating that the X-ray detector 600 is combined with no receptors. It is understood that a light other than a blue light may be emitted to output the information.

Accordingly, the X-ray detector 600 outputs different indicators to the output unit 640 according to the identification information, and thus a user easily recognizes the X-ray detector 600, which is to be used for imaging, even without spending much time and effort.

As illustrated in FIG. 25, since the output unit 640 of the X-ray detector 600 emits a blue light, the user may easily recognize that the X-ray detector 600 selected in operation S520 is a portable type X-ray detector, which is combined with no receptors.

In operation S580, the X-ray detector 600 is activated based on the signal received from the X-ray apparatus 500 in operation S530.

Figure 26:
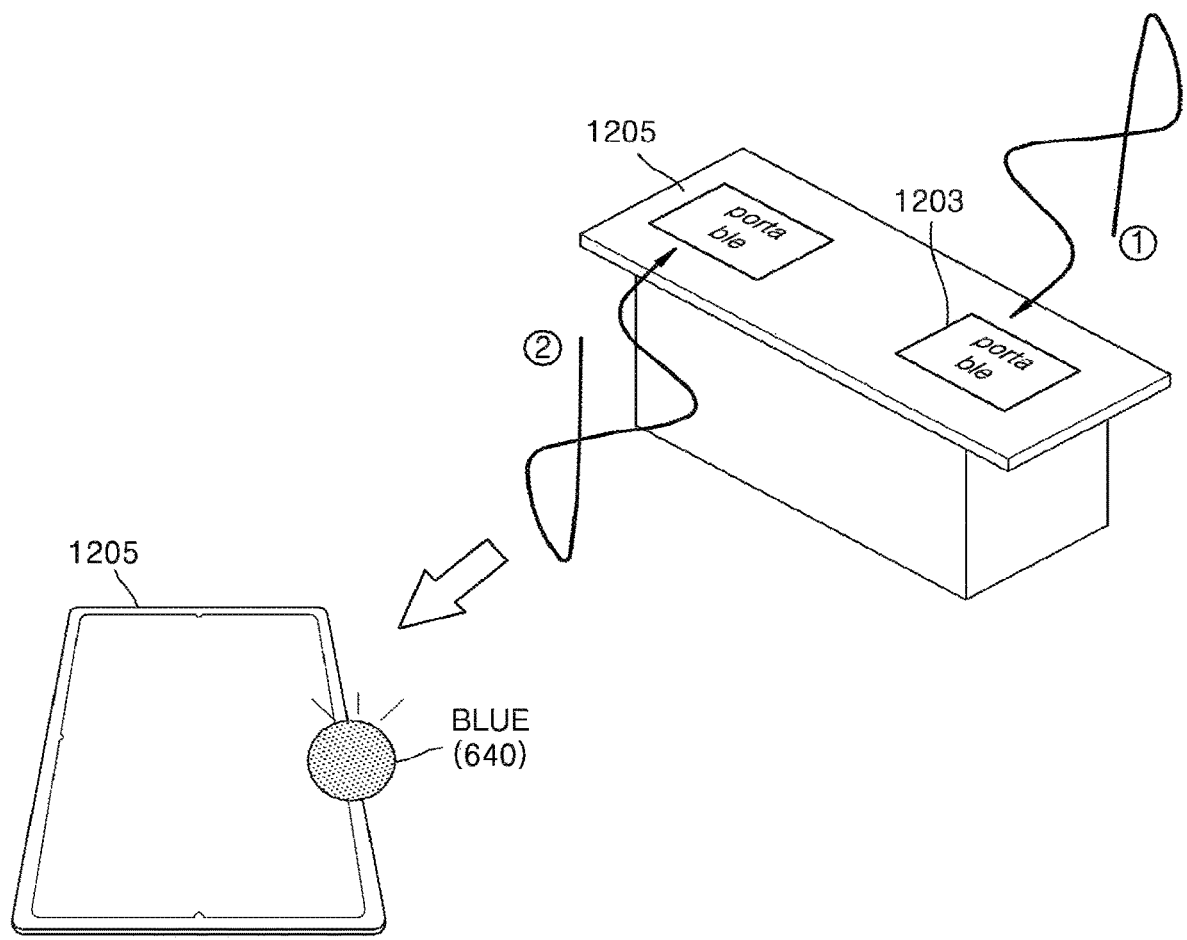
FIG. 26 illustrates an example in which an X-ray apparatus according to an exemplary embodiment selects an X-ray detector from a plurality of X-ray detectors based on motion time information of an X-ray detector.

FIG. 26 illustrates an example in which the X-ray apparatus 500 of FIG. 5 selects an X-ray detector from a plurality of X-ray detectors based on motion information of an X-ray detector.

For example, the X-ray apparatus 500 of FIG. 5 may select the X-ray detector based on orientation information of the X-ray radiator 510 and motion time information corresponding to a time section during which the X-ray detector moves.

For example, as shown in FIG. 26, an X-ray detector 1205 that has moved last from among a plurality of X-ray detectors 1203 and 1205 that have a predetermined relationship with the orientation of the X-ray radiator 510 may be selected.

For example, the motion time information corresponding to the time section during which the X-ray detector moves may include information about a first time at which a movement of the X-ray detector has been sensed and information about a second time at which consecutive movements are no longer sensed.

In this case, as shown in FIG. 26, when the X-ray detector 1203 has first moved (corresponding to a movement having a movement trajectory ①) and then the X-ray detector 1205 has moved (corresponding to a movement having a movement trajectory ②), the X-ray detector 1205 with respect to which the second time when consecutive movements are no longer sensed is most recent may be selected from the X-ray detectors 1203 and 1205.

Since the movement direction of the selected X-ray detector 1205 is neither a vertical direction of a certain trajectory nor a horizontal direction thereof, information (e.g., a portable type X-ray detector) indicating that the selected X-ray detector 1205 is combined with no receptors may be generated as identification information of the selected X-ray detector 1205. Accordingly, an output unit 640 of the X-ray detector 1205 may emit a blue light.

The output unit 540 of the X-ray apparatus 500 may display an icon of the X-ray detector 1205 that represents identification information of the X-ray detector 1205.

FIGS. 27, 28, 29, 30 and 31 illustrate various examples in which the X-ray apparatus 500 of FIG. 5 determines identification information of the X-ray detector 600 based on motion information of the X-ray detector 600.

The X-ray apparatus 500 may generate identification information of the X-ray detector 600 selected based on orientation information of the X-ray radiator 510 and the motion information of the X-ray detector 600. Alternatively, the X-ray apparatus 500 may receive identification information of the X-ray detector 600 generated by the X-ray detector 600.

For example, the identification information of the selected X-ray detector 600 may be generated based on motion directional information corresponding to a direction in which the selected X-ray detector 600 moves.

In this case, the identification information of the X-ray detector 600 may include mounting position information of the X-ray detector 600. In this case, the mounting position information of the X-ray detector 600 may include at least one selected from information indicating that the X-ray detector 600 has been combined with a stand type receptor, information indicating that the X-ray detector 600 has been combined with a table type receptor, and information indicating that the X-ray detector 600 is combined with no receptors.

Figure 27:
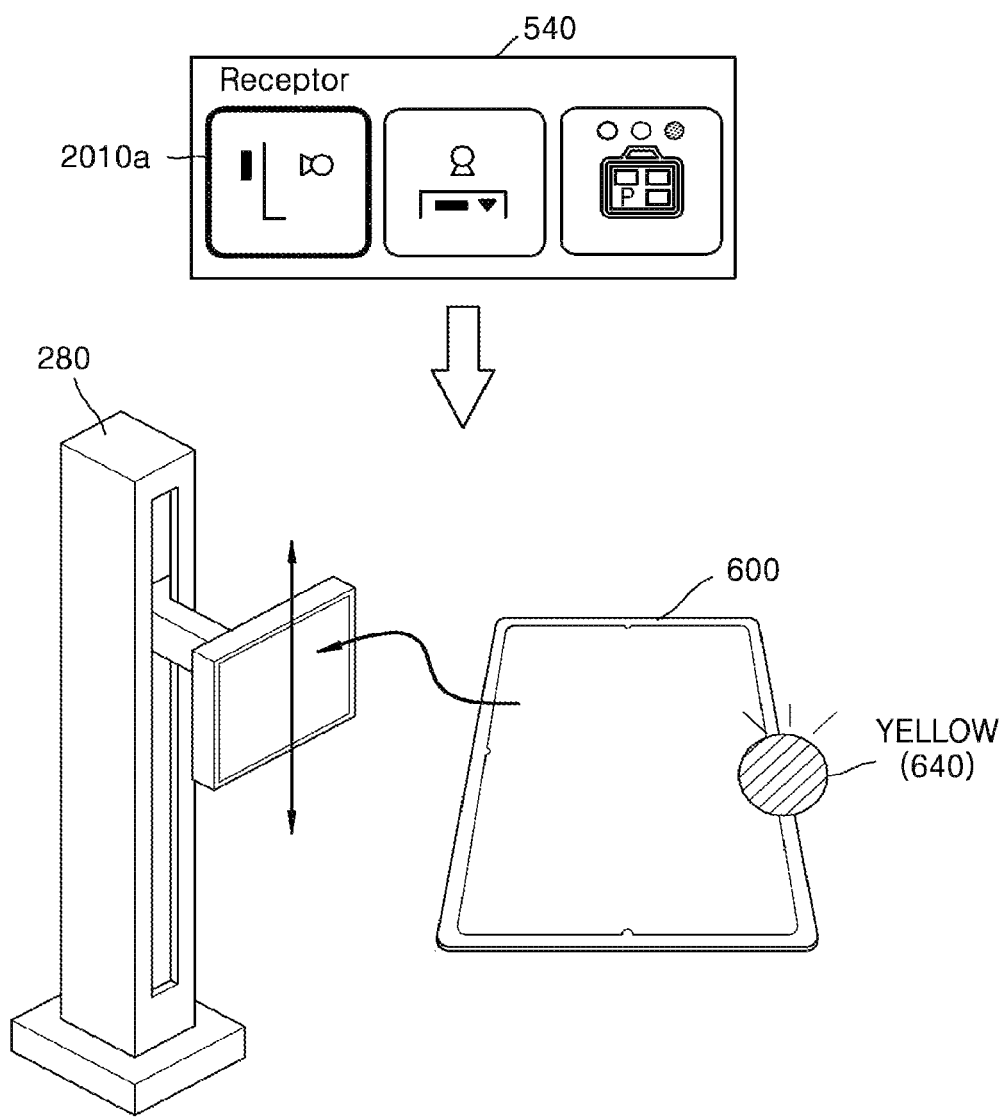
FIGS. 27, 28, 29, 30 and 31 illustrate various examples in which an X-ray apparatus according to an exemplary embodiment determines identification information of an X-ray detector based on motion directional information of the X-ray detector.

As shown in FIG. 27, when the movement direction of the X-ray detector 600 is a vertical direction of a certain trajectory, the identification information of the X-ray detector 600 may include the information indicating that the X-ray detector 600 has been combined with a stand type receptor.

In this case, the output unit 540 of the X-ray apparatus 500 may display an icon 2010*a* representing that the X-ray detector 600 has been combined with a stand type receptor 280.

The output unit 640 of the X-ray detector 600 may output a yellow indicator corresponding to information indicating that the X-ray detector 600 has been combined with the stand type receptor 280.

Figure 28:
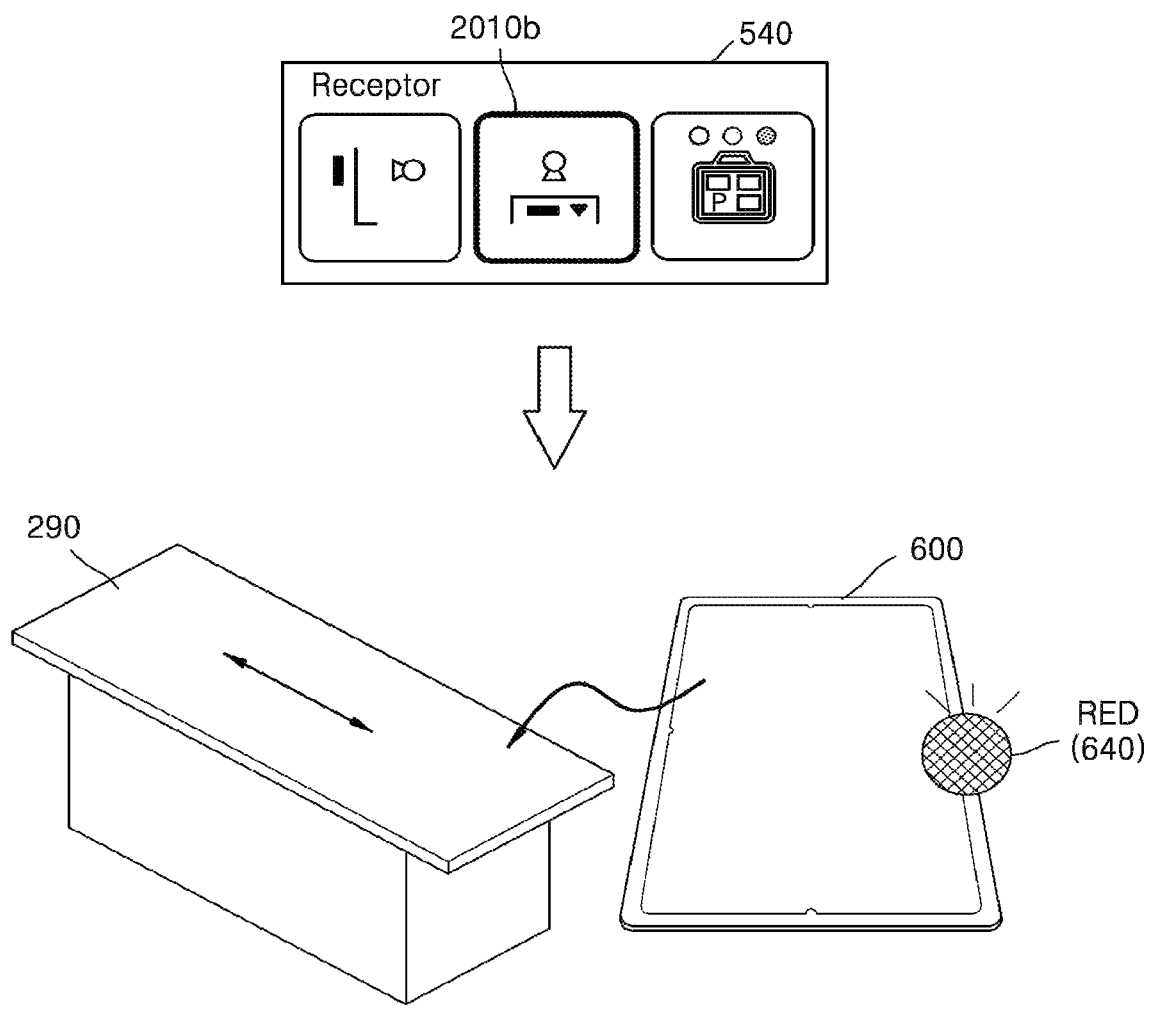

As shown in FIG. 28, when the movement direction of the X-ray detector 600 is a horizontal direction of a certain trajectory, the identification information of the X-ray detector 600 may include the information indicating that the X-ray detector 600 has been combined with a table type receptor.

In this case, the output unit 540 of the X-ray apparatus 500 may display an icon 2010*b* representing that the X-ray detector 600 has been combined with a table type receptor 290.

The output unit 640 of the X-ray detector 600 may output a red indicator corresponding to information indicating that the X-ray detector 600 has been combined with the table type receptor 290.

Figure 29:
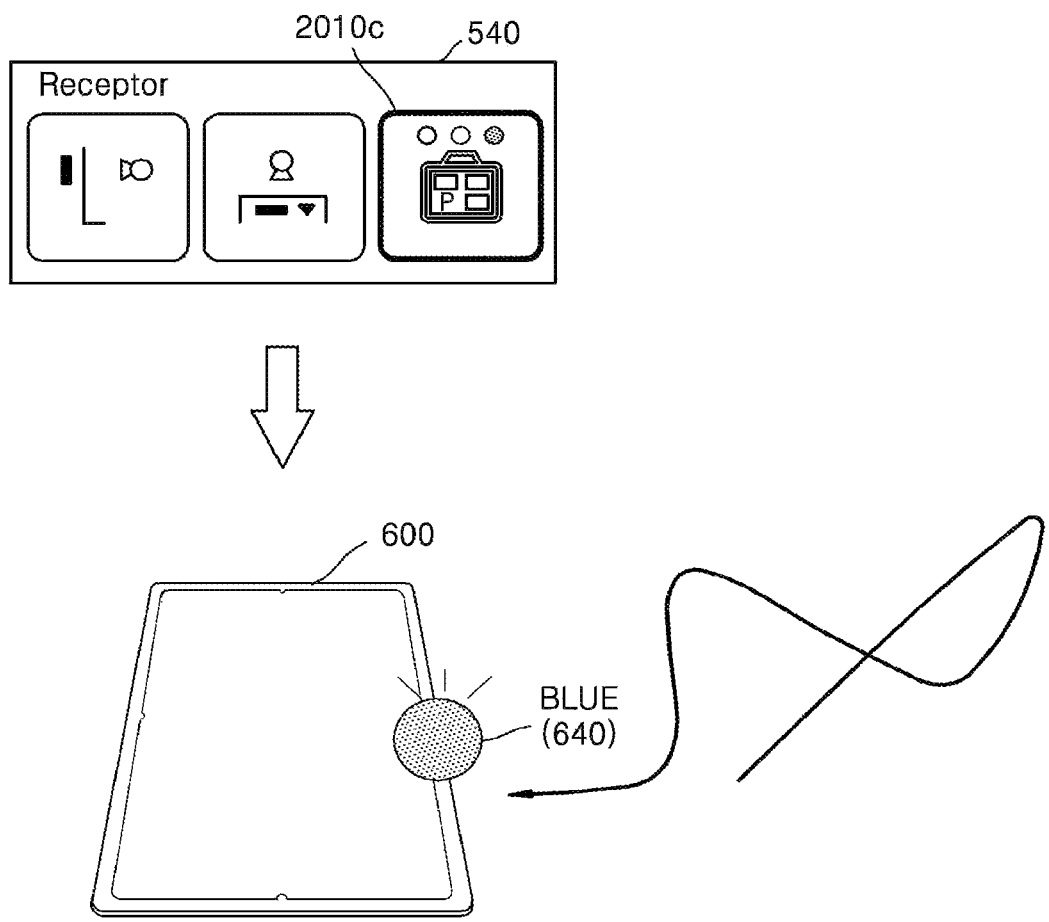

As shown in FIG. 29, when the movement direction of the X-ray detector 600 is neither a vertical direction nor a horizontal direction of a certain trajectory, the identification information of the X-ray detector 600 may include the information indicating that the X-ray detector 600 is combined with no receptors.

Figure 30:
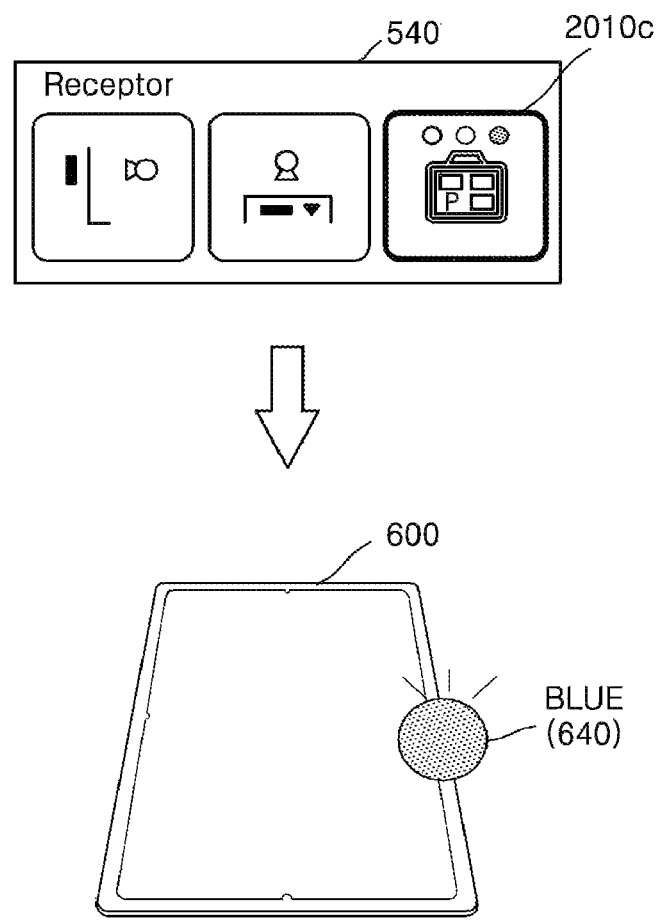

As shown in FIG. 30, even when no movements of the X-ray detector 600 are sensed, the identification information of the X-ray detector 600 may include the information indicating that the X-ray detector 600 is combined with no receptors.

In this case, the output unit 540 of the X-ray apparatus 500 may display an icon 2010c representing that the X-ray detector 600 is a portable type X-ray detector.

The output unit 640 of the X-ray detector 600 may output a blue indicator corresponding to information indicating that the X-ray detector 600 is combined with no receptors.

Accordingly, an X-ray apparatus according to another exemplary embodiment generates identification information of an X-ray detector selected based on orientation information of an X-ray radiator included in the X-ray radiator and motion information of the X-ray detector, and displays an icon representing the identification information on a display of the X-ray apparatus or a display of the X-ray detector. Accordingly, a user easily recognizes an X-ray detector that is used for imaging, even without spending much time and effort. It is understood that the icons are not limited to the exemplary icons shown in FIGS. 27-30, and many different types of icons, as well as sound effects and other types of stimuli (e.g., vibrations), may instead be used.

During a time section in which an X-ray detector moves, the X-ray detector may move in a plurality of series of trajectories.

Figure 31:
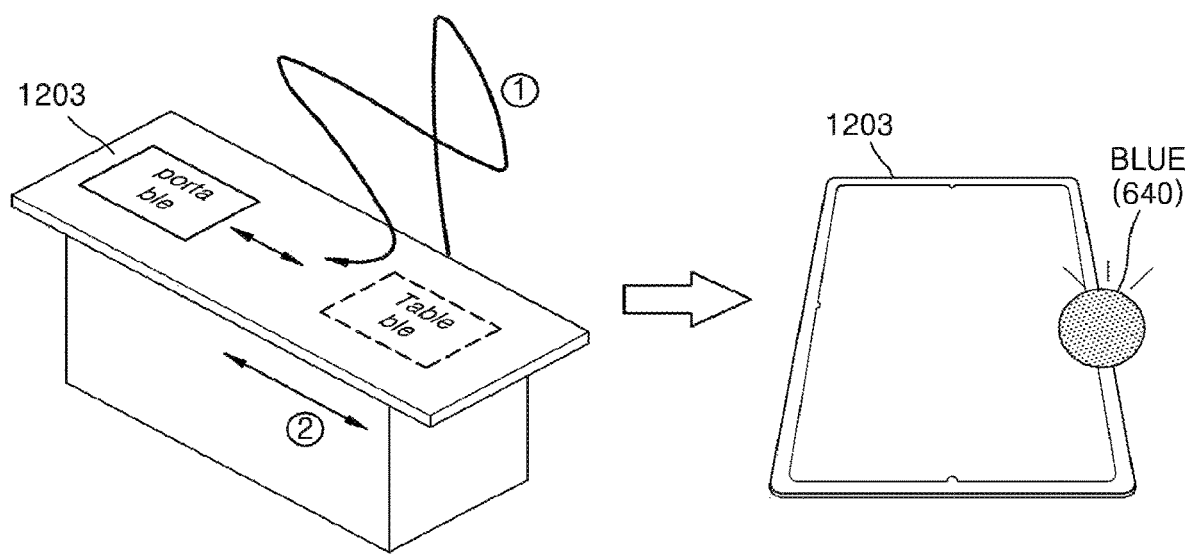

As shown in FIG. 31, the X-ray detector 1203 may make a second movement (corresponding to a movement having a movement trajectory ②) after making a first movement (corresponding to a movement having a movement trajectory ①).

In this case, the direction of the movement trajectory of the first movement is neither a vertical direction of a certain trajectory nor a horizontal direction thereof, and the direction of the movement trajectory of the second movement is the horizontal direction of the certain trajectory.

As described above, generated identification information of the X-ray detector 1203 may include information indicating that the X-ray detector 1203 is combined with no receptors, based on motion direction information corresponding to the direction of the first movement.

On the other hand, based on motion direction information corresponding to the direction of the second movement, generated identification information of the X-ray detector 1203 may include information indicating that the X-ray detector 1203 has been combined with a table type receptor.

In this case, when a movement trajectory corresponding to a last movement of the X-ray detector 1203 has a vertical or horizontal direction of a certain trajectory, the identification information of the X-ray detector 1203 may be acquired based on a movement trajectory corresponding to a movement that is previous to the last movement.

As shown in FIG. 31, the identification information of the X-ray detector 1203 may be acquired based on a movement direction corresponding to the first movement.

Accordingly, since the movement direction of the first movement of the X-ray detector 1203 is neither a vertical direction nor a horizontal direction of a certain trajectory, the identification information of the X-ray detector 1203 may include the information indicating that the X-ray detector 1203 is combined with no receptors.

In this case, the output unit 640 of the X-ray detector 1203 may output a blue indicator corresponding to information indicating that the X-ray detector 1203 is combined with no receptors.

The output unit 540 of the X-ray apparatus 500 may display an icon representing that the X-ray detector 1203 is a portable type X-ray detector.

Figure 32:
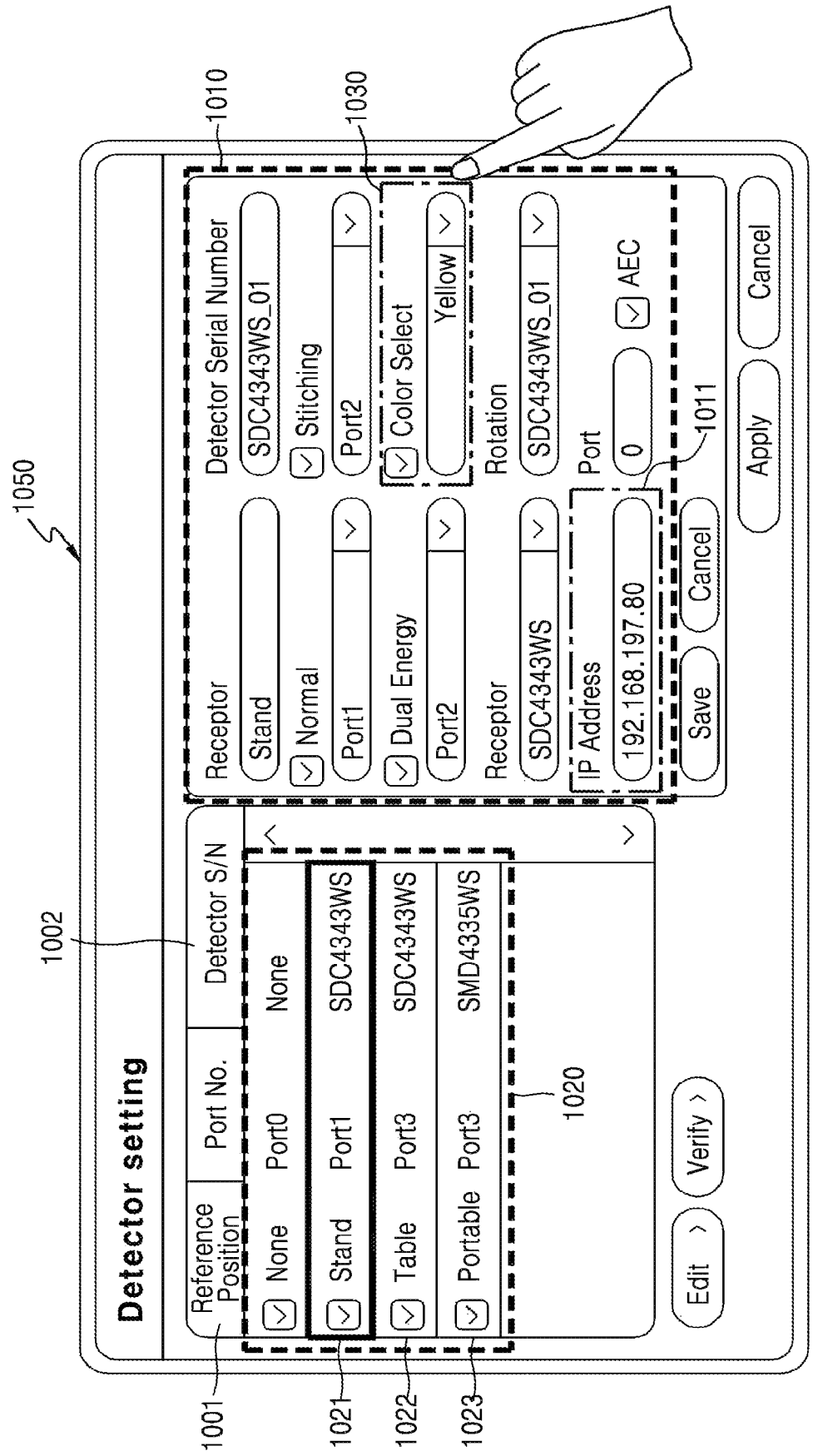
FIG. 32 illustrates an example of displaying, on an output unit, identification information of an X-ray detector selected by an X-ray apparatus according to an exemplary embodiment.

FIG. 32 illustrates an example in which an X-ray apparatus according to an exemplary embodiment displays identification information of an X-ray detector selected by the X-ray apparatus, on an output unit of the X-ray apparatus.

An X-ray apparatus according to another exemplary embodiment may sense movements of a plurality of X-ray detectors within a imaging space, automatically select an X-ray detector that is to be used for imaging from the plurality of X-ray detectors, and identify the selected X-ray detector. However, since the movements of the plurality of X-ray detectors are sensed, a user should check if a correct X-ray detector has been selected as the X-ray detector that is to be used for imaging.

To this end, the X-ray apparatus may output, on an output unit included therein, a UI 1050 enabling the user to check information about the X-ray detector that is to be used for imaging.

When a plurality of X-ray detectors may sense respective movements thereof, a movement of an X-ray detector that is to be used for imaging may be sensed, and movements of X-ray detectors other than the X-ray detector that is to be used for imaging may be sensed.

In this case, the X-ray apparatus may select the X-ray detector that is to be used for imaging, based on orientation information of an X-ray radiator included in the X-ray apparatus and motion information of the X-ray detector. As described above, an X-ray detector which has moved last may be selected from the plurality of detectors.

For example, when a first X-ray detector has first moved in a horizontal direction of a certain trajectory and then a second X-ray detector has moved in a vertical direction of the certain trajectory, the second X-ray detector that has moved last may be selected as the X-ray detector that is to be used for imaging. Identification information of the second X-ray detector may include information indicating that the second X-ray detector has been combined with a stand type receptor.

In this connection, the UI 1050 may provide information about the selected second X-ray detector and may display 'Yellow' corresponding to the identification information of the second X-ray detector that has moved last, on Color Select 1030.

If 'RED' is displayed on the Color Select 1030 of the UI 1050, this indicates that an X-ray detector has been combined with a table type receptor, and thus it may be seen that the first X-ray detector that has moved in the horizontal direction of the certain trajectory has been selected. In this case, since the X-ray apparatus does not select the second X-ray detector that has moved last but selects the first X-ray detector that has first moved, it may be determined that the X-ray apparatus has made an erroneous selection.

Accordingly, the X-ray apparatus provides a UI capable of displaying an indicator of the selected X-ray detector, and thus a user may recognize that an X-ray detector conforming to an intention of the user has been selected.

In addition, the X-ray apparatus may set sensing of only movements of X-ray detectors that are present within an X-ray imaging space designated by a user. In this case, the X-ray apparatus may not sense movements of X-ray detectors that are outside the designated X-ray imaging space.

When a plurality of X-ray detectors are selected based on motion information of the X-ray detectors, the X-ray apparatus may select at least one X-ray detector that is to be used for imaging, based on additional information other than the motion information of the X-ray detectors.

For example, an X-ray detector may be selected based on, for example, variation information of a temperature or touch information, which is sensed by a sensor unit of the X-ray detector.

The exemplary embodiments can be written as computer programs and can be implemented in general-use digital computers that execute the programs using a non-transitory computer readable recording medium.

Examples of the non-transitory computer readable recording medium include magnetic storage media (e.g., ROM, floppy disks, hard disks, etc.), optical recording media (e.g., CD-ROMs, or DVDs), etc.

The exemplary embodiments should be considered in a descriptive sense only and not for purposes of limitation. Descriptions of features or aspects within each exemplary embodiment should typically be considered as available for other similar features or aspects in other exemplary embodiments.

While the exemplary embodiments have been particularly shown and described with reference to certain exemplary embodiments thereof, it will be understood by those of ordinary skill in the art that various changes in form and details may be made therein without departing from the spirit and scope of the exemplary embodiments as defined by the following claims.

What is claimed is:

1. An X-ray apparatus comprising:
a display;
an X-ray radiator configured to radiate X-rays to an object;
a plurality of X-ray detectors configured to detect the X-rays radiated by the X-ray radiator and provide motion information regarding each of the plurality of X-ray detectors;
a communicator configured to communicate with the plurality of X-ray detectors wirelessly; and
a controller configured to:
control the communicator to receive the motion information regarding each of the plurality of X-ray detectors from the plurality of X-ray detectors,
select at least one X-ray detector, from among the plurality of X-ray detectors, based on orientation information indicating an orientation of the X-ray radiator and the motion information,
control the communicator to receive an identification information of the selected at least one X-ray detector, and
control the display to display at least one icon representing the received identification information.

2. The X-ray apparatus of claim 1, wherein the controller is further configured to control the communicator to transmit an informing signal to the selected at least one X-ray detector for informing selection of X-ray detector.

3. The X-ray apparatus of claim 1, wherein the controller is further configured to control the communicator to transmit an activation signal to the selected at least one X-ray detector and activate the selected at least one X-ray detector for X-ray imaging.

4. The X-ray apparatus of claim 1, wherein the motion information comprises motion time information corresponding to time periods during which the corresponding plurality of X-ray detectors move, and the controller is further configured to select the at least one X-ray detector from among the plurality of X-ray detectors, based on the orientation information of the X-ray radiator and the motion time information.

5. The X-ray apparatus of claim 4, wherein the controller is further configured to select an X-ray detector that has moved most recently from among the plurality of X-ray detectors based on the motion time information.

6. The X-ray apparatus of claim 5, the controller is further configured to control the display to display an user interface (UI) comprising at least one color corresponding to the identification information of the selected X-ray detector that has moved most recently.

7. The X-ray apparatus of claim 1, wherein the motion information comprises motion direction information indicating a movement direction of the selected at least one X-ray detector, and
the identification information identifying the selected at least one X-ray detector is generated based on motion direction information by the selected X-ray detector.

8. The X-ray apparatus of claim 7, wherein the identification information identifying the selected at least one X-ray detector comprises at least one selected from information indicating that the selected at least one X-ray detector is combined with a stand type receptor, information indicating that the selected at least one X-ray detector is combined with a table type receptor, and information indicating that the selected at least one X-ray detector is not combined with any receptors.

9. The X-ray apparatus of claim 8, wherein, when the motion direction information indicates that the movement direction of the selected at least one X-ray detector is a first direction having a first trajectory, the controller is further configured to generate information indicating that the selected at least one X-ray detector is combined with the table type receptor.

10. The X-ray apparatus of claim 8, wherein, when the motion direction information indicates that the movement direction of the selected at least one X-ray detector is a second direction having a second trajectory, the controller is further configured to generate information indicating that the selected at least one X-ray detector is combined with the stand type receptor.

11. The X-ray apparatus of claim 8, wherein, when the motion direction information indicates that the movement direction of the selected at least one X-ray detector is neither a vertical direction nor a horizontal direction of a certain trajectory, the controller is further configured to generate the information indicating that the selected at least one X-ray detector is not combined with any receptors.

12. An X-ray detector comprising:
an outputter comprising a color indicator;
a sensor configured to acquire motion information of the X-ray detector indicating a movement of the X-ray detector;
a communicator configured to transmit motion information to an X-ray apparatus to permit the X-ray apparatus to select the X-ray detector to be used for imaging based on the motion information; and
a detector controller configured to:
control the communicator to transmit the motion information to the X-ray apparatus and receive a control signal generated based on the motion information from the X-ray apparatus,
generate identification information identifying the X-ray detector based on the received control signal, control the outputter to emit a light of color corresponding to the generated identification information, and
control an operation of the X-ray detector based on the received control signal.

13. The X-ray detector of claim 12, wherein the detector controller is further configured to acquire the motion information based on a direction of the movement of the X-ray detector.

14. The X-ray detector of claim 12, wherein the detector controller is further configured to acquire the motion information based on a time period during which the movement of the X-ray detector occurs.

15. The X-ray detector of claim 12, wherein the detector controller is further configured to control the communicator to transmit the motion information to the X-ray apparatus at a predetermined time before receiving the control signal from the X-ray apparatus.

16. The X-ray detector of claim 12, wherein the identification information comprises a mounting position information indicating a position of the X-ray detector combined with a plurality of receptor, and
the detector controller is further configured to control the outputter to emit different color of light based on the mounting position information of the X-ray detector.

17. The X-ray detector of claim 12, wherein the detector controller is configured to control the X-ray detector to prepare to receive radiated X-rays from the X-ray apparatus, based on the received control signal.

* * * * *